United States Patent
Tanabe et al.

(10) Patent No.: US 9,424,999 B2
(45) Date of Patent: Aug. 23, 2016

(54) DYE FOR PHOTOELECTRIC CONVERSION DEVICE AND PHOTOELECTRIC CONVERSION DEVICE

(71) Applicants: Junji Tanabe, Tokyo (JP); Atsushi Monden, Tokyo (JP); Masahiro Shinkai, Tokyo (JP); Mitsuhiro Okada, Tokyo (JP); Toru Yano, Tokyo (JP); Yohei Aoyama, Tokyo (JP); Yusuke Kubota, Tokyo (JP)

(72) Inventors: Junji Tanabe, Tokyo (JP); Atsushi Monden, Tokyo (JP); Masahiro Shinkai, Tokyo (JP); Mitsuhiro Okada, Tokyo (JP); Toru Yano, Tokyo (JP); Yohei Aoyama, Tokyo (JP); Yusuke Kubota, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 43 days.

(21) Appl. No.: 14/489,911

(22) Filed: Sep. 18, 2014

(65) Prior Publication Data

US 2015/0027542 A1    Jan. 29, 2015

Related U.S. Application Data

(62) Division of application No. 13/062,136, filed as application No. PCT/JP2009/065713 on Sep. 9, 2009, now Pat. No. 8,884,029.

(30) Foreign Application Priority Data

Sep. 30, 2008 (JP) .................................. 2008-254670

(51) Int. Cl.
*H01G 9/20* (2006.01)
*C07D 403/06* (2006.01)

(Continued)

(52) U.S. Cl.
CPC ............ *H01G 9/2059* (2013.01); *C07D 403/06* (2013.01); *C07D 413/06* (2013.01); *C07D 417/06* (2013.01); *C07D 421/06* (2013.01); *C09B 23/0058* (2013.01); *C09B 23/0066* (2013.01); *C09B 23/02* (2013.01); *C09B 23/083* (2013.01); *H01L 51/0064* (2013.01); *H01M 14/005* (2013.01); *H01G 9/2013* (2013.01); *H01G 9/2031* (2013.01); *Y02E 10/542* (2013.01)

(58) Field of Classification Search
None
See application file for complete search history.

(56) References Cited

U.S. PATENT DOCUMENTS 2,471,488 A   5/1949   Kendall et al.
2,542,401 A   2/1951   Doyle et al.
(Continued)

FOREIGN PATENT DOCUMENTS

GB    640127    7/1950
JP    A-61-275745    12/1986
(Continued)

OTHER PUBLICATIONS

International Search Report in International Application No. PCT/JP2009/065713 dated Dec. 8, 2009 (with English translation).

*Primary Examiner* — Ling Choi
*Assistant Examiner* — Catherine S Branch
(74) *Attorney, Agent, or Firm* — Oliff PLC

(57) ABSTRACT

A photoelectric conversion device that includes a work electrode, an opposed electrode, and an electrolyte-containing layer. In the work electrode, a metal oxide semiconductor layer supporting a dye is provided. The dye contains a cyanine compound that has a methine chain, an indolenine skeleton bonded with both ends of the methine chain, and anchor groups introduced to a nitrogen atom included in the indolenine skeleton. Electron injection efficiency to the metal oxide semiconductor layer is improved, and the dye is hardly exfoliated from the metal oxide semiconductor layer.

6 Claims, 2 Drawing Sheets

(51) Int. Cl.

| | |
|---|---|
| *C07D 421/06* | (2006.01) |
| *C07D 413/06* | (2006.01) |
| *C07D 417/06* | (2006.01) |
| *C09B 23/01* | (2006.01) |
| *C09B 23/02* | (2006.01) |
| *C09B 23/08* | (2006.01) |
| *H01L 51/00* | (2006.01) |
| *H01M 14/00* | (2006.01) |

(56) References Cited

U.S. PATENT DOCUMENTS

| | | |
|---|---|---|
| 3,090,782 A | 5/1963 | Weissel et al. |
| 3,846,137 A | 11/1974 | Riester et al. |
| 3,970,461 A | 7/1976 | Shiba et al. |
| 8,912,344 B2 * | 12/2014 | Tanabe .............. C09B 23/0008 548/426 |
| 2004/0166515 A1 | 8/2004 | Terpetschnig et al. |
| 2004/0186278 A1 | 9/2004 | Chen et al. |
| 2008/0207918 A1 * | 8/2008 | Aoyama ............. C09B 23/0058 548/455 |
| 2008/0236663 A1 * | 10/2008 | Tanabe .............. C09B 23/0066 136/256 |
| 2011/0253218 A1 | 10/2011 | Tanabe et al. |
| 2013/0186468 A1 | 7/2013 | Tanabe et al. |

FOREIGN PATENT DOCUMENTS

| | | |
|---|---|---|
| JP | A-2002-264504 | 9/2002 |
| JP | A-2007-220412 | 8/2007 |
| JP | A-2008-101064 | 5/2008 |
| JP | A-2008-166119 | 7/2008 |
| WO | WO 2009/014513 A1 | 1/2009 |

* cited by examiner

DYE FOR PHOTOELECTRIC CONVERSION DEVICE AND PHOTOELECTRIC CONVERSION DEVICE

This is a divisional of application Ser. No. 13/062,136 filed Mar. 3, 2011, which is a National Stage Application of PCT/W2009/065713 filed Sep. 9, 2009, and claims the benefit of Japanese Application No. 2008-254670 filed Sep. 30, 2008. The entire disclosures of the prior applications are hereby incorporated by reference in their entirety.

BACKGROUND

The present invention relates to a photoelectric conversion device using a dye and a dye suitably used for the photoelectric conversion device.

In the past, in various technology fields, dyes have been widely used. To take an example, in the photoelectric conversion device field such as a solar cell, dyes are used for a dye-sensitized photoelectric conversion device for sensitizing by making an oxide semiconductor electrode support a dye. In the dye-sensitized photoelectric conversion device, high efficiency is able to be expected theoretically. In addition, the dye-sensitized photoelectric conversion device is regarded as a device that is significantly advantageous on the cost front more than an existing photoelectric conversion device using silicon semiconductor.

In the dye-sensitized photoelectric conversion device, the dye supported by the oxide semiconductor electrode absorbs light and excited, and electrons are injected into the oxide semiconductor. Thereby, photoelectron conversion is made. As the dye used for the dye-sensitized photoelectric conversion device, a ruthenium complex dye and an organic dye are known. In particular, the organic dye is comparatively stable and is able to be easily synthesized, and thus various studies have been made for the organic dye. Specifically, the technology using a cyanine dye having an anchor group for being absorbed to the oxide semiconductor electrode together with a structure in which an indolenine skeleton is bonded with both ends of a methine chain skeleton for the purpose of improving conversion efficiency or the like has been known (for example, refer to Patent Document 1).

Patent Document 1: Japanese Unexamined Patent Application Publication No. 2007-220412

SUMMARY

However, in the existing dye used for the photoelectric conversion device, there are problems in fixation characteristics to a base substance containing an oxide semiconductor material or the like and electron mobility from dye molecules to the base substance. Specifically, in the existing dye, for example, even if the dye is absorbed to the base substance containing the oxide semiconductor material or the like, when the dye is soaked in water or an organic solvent, the dye is easily exfoliated. In addition, even if the dye absorbs light and is excited, electron mobility for effectively injecting electrons into the base substance is not sufficient. Thus, in the photoelectric conversion device using the dye, in the case where the dye supported by the oxide semiconductor electrode is contacted with an electrolyte containing an organic solvent, the dye is easily exfoliated and electron injection efficiency to the oxide semiconductor electrode is low, and thus high conversion efficiency has been hardly obtained.

In view of the foregoing problems, it is a first object of the present invention to provide a photoelectric conversion device capable of improving conversion efficiency. Further, it is a second object of the present invention to provide a dye for a photoelectric conversion device that has high electron injection efficiency to a base substance containing, for example, a metal oxide semiconductor material or the like and that has high fixation characteristics.

A photoelectric conversion device of the present invention is a photoelectric conversion device comprising an electrode having a dye and a support body that supports the dye. The dye contains a cyanine compound expressed by Chemical formula (1).

[Formula 1]

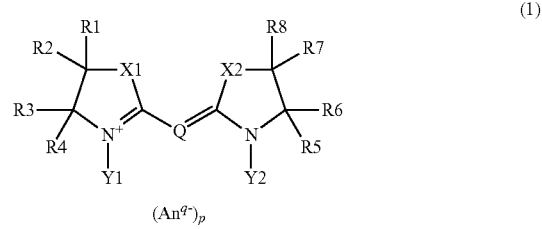

(R1 to R8 are respectively and independently a hydrogen atom, a hydroxyl group, an alkyl group, an alkoxy group, an alkyl group having one or more substituent groups, an alkoxy group having one or more substituent groups, or the group expressed by Chemical formula (2). At least one of R1 and R2 and at least one of R3 and R4; and at least one of R5 and R6 and at least one of R7 and R8 may be respectively detached to form an unsaturated bond, or may be respectively linked with each other to form a ring structure. Y1 and Y2 are an anchor group. Q is a linkage group that has a methine chain with carbon atomicity from 1 to 7 both inclusive as a skeleton and that has one or more cyano groups. X1 is a group expressed by —C(R9)(R10)— or —N(R11)—, a sulfur atom, an oxygen atom, a selenium atom, or a tellurium atom. X2 is a group expressed by —C(R12)(R13)— or —N(R14)—, a sulfur atom, an oxygen atom, a selenium atom, or a tellurium atom. R9 to R14 are respectively and independently a hydrogen atom, a hydroxyl group, an alkyl group, an alkoxy group, an alkyl group having one or more substituent groups, an alkoxy group having one or more substituent groups, or the group expressed by Chemical formula (2). $An^{q-}$ is an anion with q valency. q is 1 or 2, and p is a coefficient to maintain neutral electric charge.)

[Formula 2]

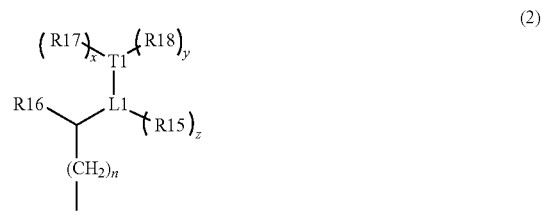

(Bond between L1 and T1 is double bond or triple bond. L1 represents a carbon atom. T1 represents a carbon atom, an oxygen atom, or a nitrogen atom. x, y, and z are respectively and independently 0 or 1 (x and y are 0 where T1 is an oxygen atom, and (y+z) is 0 or 1 where T1 is a nitrogen atom). R15 to R17 are respectively and independently a hydrogen atom, a hydroxyl group, a nitro group, a cyano group, a halogen atom, an alkyl group with carbon atomicity from 1 to 4 both inclusive, or an alkyl group with carbon atomicity from 1 to 4 both inclusive substituted by one or more halogen atoms. R18 is a hydrogen atom, a hydroxyl group, a nitro group, a cyano group, a halogen atom, an alkyl group with carbon atomicity from 1 to 4 both inclusive, an alkoxy group with carbon atomicity from 1 to 4 both inclusive, an alkyl group with carbon atomicity from 1 to 4 both inclusive substituted by one or more halogen atoms, or an alkoxy group with carbon atomicity from 1 to 4 both inclusive substituted by one or more halogen atoms. R15 and R18/R16 and R17 may be respectively linked with each other to form a ring structure. n is an integer number out of 0 to 4.)

"may be detached to form an unsaturated bond" explained in Chemical formula (1) means that it is possible that one of R1 and R2 and one of R3 and R4 are detached, and bond between a carbon atom to which R1 and R2 are introduced and a carbon atom to which R3 and R4 are introduced is double bond. The same is applied to bond between a carbon atom to which R5 and R6 in Chemical formula (1) are introduced and a carbon atom to which R7 and R8 in Chemical formula (1) are introduced, or bond between a carbon atom to which R5 and R6 in Chemical formula (3) described later are introduced and a carbon atom to which R7 and R8 in Chemical formula (3) are introduced. Further, "anchor group" means a group having chemical or electrostatic affinity and binding ability in relation to a support body.

In the photoelectric conversion device of the present invention, the dye contains the cyanine compound expressed by Chemical formula (1). Thereby, electron injection from the dye to the support body becomes effective, and the dye is hardly exfoliated from the support body. Specifically, the cyanine compound shown in Chemical formula (1) has the anchor groups introduced to the nitrogen atom in the heterocyclic skeleton bonded with both ends of the methine chain skeleton and the cyano group introduced to the carbon atom structuring the methine chain skeleton. Thereby, physical distance between the cyano group and the support body becomes close, and interaction is generated between an unshared electron pair of the cyano group introduced to the methine chain and the support body. In result, resistance at the time of electron injection from the cyanine compound to the support body is decreased. Thereby, in the case where the dye absorbs and is excited, electrons are effectively injected into the support body. In addition, for example, if the dye is contacted with an organic solvent contained in an electrolyte or the like or moisture intruding in the device in a state that the dye is supported by the support body, the dye is not easily exfoliated. Thus, electron injection amount ratio to the support body in relation to light absorption amount is increased as the entire dye, and exfoliation from the support body is inhibited, and therefore photoelectric conversion is favorably made.

In the photoelectric conversion device of the present invention, the cyanine compound shown in Chemical formula (1) may be a compound expressed by Chemical formula (3). In this case, at least one of R9 and R10 shown in Chemical formula (3) is preferably an alkyl group with carbon atomicity from 6 to 25 both inclusive. In general, in the case where the cyanine structure (structure in which a heterocyclic skeleton is bonded with both ends of a methine chain skeleton) includes an indolenine skeleton as a heterocyclic skeleton, a structure in which carbon atoms (and a hetero atom (nitrogen atom)) included in the methine chain skeleton and the indolenine skeleton are arrayed in the same plane (structure with high planarity) exists. In result, each molecule gets together to easily form an association body such as a dimer. However, in the case where the sterically bulky alkyl group with carbon atomicity from 6 to 25 both inclusive is introduced as at least one of R9 and R10 in Chemical formula (3), the steric ally bulky group is introduced to occupy at least one space out of the upper face side and the lower face side in relation to the plane including the methine chain skeleton and the indolenine skeleton. Thereby, the steric size of the entire molecule becomes large, which hardly forms an association body. Thereby, the ratio of the association body that hardly contributes to photoelectric conversion in the entire dye is decreased on the surface of the support body. Thus, the dye effectively absorbs light, and photoelectric conversion is more favorably made.

[Formula 3]

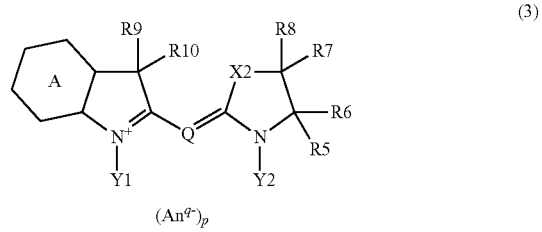

(3)

(R5 to R10 are respectively and independently a hydrogen atom, a hydroxyl group, an alkyl group, an alkoxy group, an alkyl group having one or more substituent groups, an alkoxy group having one or more substituent groups, or the group shown in the foregoing Chemical formula (2). At least one of R5 and R6 and at least one of R7 and R8 may be respectively detached to form an unsaturated bond, or may be respectively linked with each other to form a ring structure. Y1 and Y2 are an anchor group. Q is a linkage group that has a methine chain with carbon atomicity from 1 to 7 both inclusive as a skeleton and that has one or more cyano groups. X2 is a group expressed by —C(R12)(R13)— or —N(R14)—, a sulfur atom, an oxygen atom, a selenium atom, or a tellurium atom. R12 to R14 are respectively and independently a hydrogen atom, a hydroxyl group, an alkyl group, an alkoxy group, an alkyl group having one or more substituent groups, an alkoxy group having one or more substituent groups, or the group shown in the foregoing Chemical formula (2). The ring A is a benzene ring, a naphthalene ring, a benzene ring having one or more substituent groups, or a naphthalene ring having one or more substituent groups. $An^{q-}$ is an anion with q valency. q is 1 or 2, and p is a coefficient to maintain neutral electric charge.)

In the photoelectric conversion device of the present invention, the cyanine compound shown in Chemical formula (1) may be a compound expressed by Chemical formula (4). In this case, the ring A and the ring B shown in Chemical formula (4) are preferably a benzene ring having a methoxy group. Thereby, since the methoxy group introduced to the ring A and the ring B is an electron releasing group, electron injection efficiency to the support body becomes more effective, and photoelectric conversion is more favorably made. Further, in this case, at least one of R9, R10, R12, and R13 shown in Chemical formula (4) is preferably an alkyl group with carbon atomicity from 6 to 25 both inclusive. Specially, all of R9, R10, R12, and R13 are preferably the alkyl group with carbon atomicity from 6 to 25 both inclusive. Thereby, since the sterically bulky alkyl group with carbon atomicity from 6 to 25 both inclusive is introduced to occupy both spaces of the upper face side and the lower face side in relation to the plane including the methine chain skeleton and the indolenine skeleton. Thereby, the steric size of the entire molecule becomes large, which hardly forms an association body. Thereby, the ratio of the association body that hardly contributes to photoelectric conversion in the dye is decreased on the surface of the support body. Thus, photoelectric conversion is more favorably made.

[Formula 4]

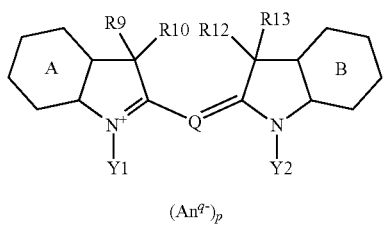

(4)

(R9, R10, R12, and R13 are respectively and independently a hydrogen atom, a hydroxyl group, an alkyl group, an alkoxy group, an alkyl group having one or more substituent groups, an alkoxy group having one or more substituent groups, or the group expressed by the foregoing Chemical formula (2). Y1 and Y2 are an anchor group. Q is a linkage group that has a methine chain with carbon atomicity from 1 to 7 both inclusive as a skeleton and that has one or more cyano groups. The ring A and the ring B are respectively and independently a benzene ring, a naphthalene ring, a benzene ring having one or more substituent groups, or a naphthalene ring having one or more substituent groups. $An^{q-}$ is an anion with q valency. q is 1 or 2, and p is a coefficient to maintain neutral electric charge.)

In the photoelectric conversion device of the present invention, Q shown in Chemical formula (1), Chemical formula (3), or Chemical formula (4) may be a linkage group in which a methine chain with carbon atomicity of 5 is a skeleton and a cyano group is introduced to a carbon atom as a center of the methine chain. The foregoing anchor group may be a group expressed by —$CH_2$—$CH_2$—C(=O)—OH or a group expressed by —$CH_2$—$CH_2$—C(=O)—$O^-$.

Further, in the photoelectric conversion device of the present invention, it is preferable that the support body is formed by electrolytic precipitation method and contains zinc oxide (ZnO). Thereby, photoelectric conversion is more favorably made.

A dye for a photoelectric conversion device of the present invention has the cyanine structure shown in the foregoing Chemical formula (1).

In the dye for a photoelectric conversion device of the present invention, the cyanine structure shown in Chemical formula (1) has the anchor groups introduced to the nitrogen atom in the heterocyclic skeleton and the cyano group introduced to the carbon atom structuring the methine chain skeleton. Thereby, for example, in the case where the dye is supported by a base substance containing a metal oxide semiconductor material included in the photoelectric conversion device, if the dye absorbs light and is excited, electrons are immediately injected into the base substance. Further in this case, if the dye is contacted with an organic solvent or moisture, the dye is not easily exfoliated from the base substance.

In the dye for a photoelectric conversion device of the present invention, the cyanine structure shown in the foregoing Chemical formula (1) may be a structure expressed by Chemical formula (3). In this case, at least one of R9 and R10 shown in Chemical formula (3) is preferably an alkyl group with carbon atomicity from 6 to 25 both inclusive. Thereby, the sterically bulky alkyl group with carbon atomicity from 6 to 25 both inclusive is introduced to occupy at least one space out of the upper face side and the lower face side in relation to the plane including the methine chain skeleton and the indolenine skeleton. Thereby, the steric size of the entire molecule becomes large, which hardly forms an association body. Thereby, the ratio of the association body that hardly contributes to electron injection to the base substance is decreased in the case where the dye is supported by the base substance. Thus, the ratio of electron injection amount to the base substance in relation to light absorption amount is increased.

Further, in the dye for a photoelectric conversion device of the present invention, the cyanine structure shown in Chemical formula (1) may be a structure expressed by Chemical formula (4). In this case, the ring A and the ring B shown in Chemical formula (4) are preferably a benzene ring having a methoxy group. Thereby, in the case where the dye is supported by the base substance, electrons are more immediately injected into the base substance. Further, in this case, at least one of R9, R10, R12, and R13 shown in Chemical formula (4) is preferably an alkyl group with carbon atomicity from 6 to 25 both inclusive. Specially, all of R9, R10, R12, and R13 are preferably the alkyl group with carbon atomicity from 6 to 25 both inclusive. Thereby, in the case where the dye is supported by the base substance, the ratio of the association body that hardly contributes to electron injection to the base substance is decreased. Thus, the ratio of electron injection amount to the base substance in relation to light absorption amount is increased.

Further, in the dye for a photoelectric conversion device of the present invention, Q shown in Chemical formula (1), Chemical formula (3), or Chemical formula (4) may be a linkage group in which a methine chain with carbon atomicity of 5 is a skeleton and a cyano group is introduced to a carbon atom as a center of the methine chain. The foregoing anchor group may be a group expressed by —$CH_2$—$CH_2$—C(=O)—OH or a group expressed by —$CH_2$—$CH_2$—C(=O)—$O^-$.

According to the photoelectric conversion device of the present invention, the electrode having the dye and the support body that supports the dye is included. The dye contains the cyanine compound shown in Chemical formula (1). Thus, compared to a case that the dye contains, for example, a compound not including the structure shown in Chemical formula (1) (for example, the cyanine compound in which the cyano group is not bonded with the methine chain skeleton), conversion efficiency is able to be improved.

Further, in this case, in the case where the cyanine structure shown in Chemical formula (1) is the compound shown in Chemical formula (4), and the ring A and the ring B in Chemical formula (4) are a benzene ring having a methoxy group, dye fixation characteristics and electron injection efficiency are more improved, and thus higher conversion efficiency is able to be obtained. In this case, in the case where at least one of R9, R10, R12, and R13 is an alkyl group with carbon atomicity from 6 to 25 both inclusive, specially, all of R9, R10, R12, and R13 are the alkyl group with carbon atomicity from 6 to 25 both inclusive, high dye fixation characteristics and higher electron injection efficiency are able to be obtained, and thus conversion efficiency is able to be more improved.

In particular, in the case where the support body is formed by electrolytic precipitation method and contains zinc oxide, conversion efficiency is able to be more improved.

According to the dye for a photoelectric conversion device of the present invention, the cyanine structure shown in Chemical formula (1) is included. Thus, for example, electron injection efficiency to the base substance containing the metal oxide semiconductor material or the like included in the photoelectric conversion device and fixation characteristics are able to be improved.

DETAILED DESCRIPTION OF EMBODIMENTS

Figure 1:
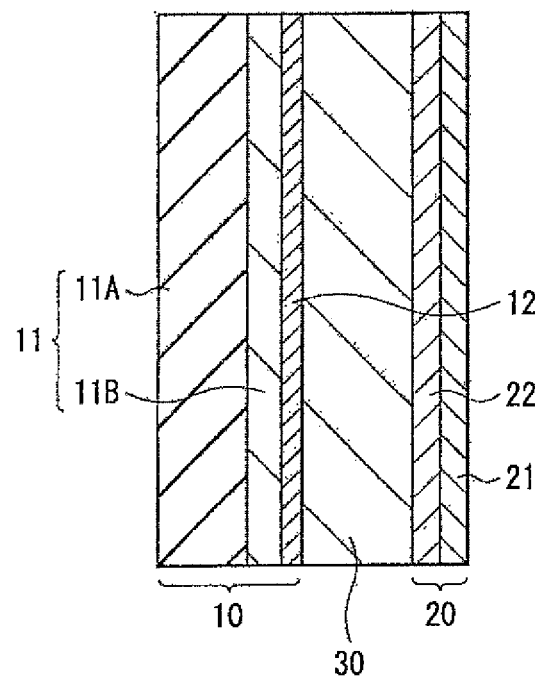
FIG. 1 is a cross sectional view illustrating a structure of a photoelectric conversion device using a dye according to an embodiment of the present invention.

An embodiment of the present invention (hereinafter simply referred to as embodiment) will be hereinafter described in detail with reference to the drawings.

A dye according to the embodiment of the invention is, for example, a compound having absorptive property (associativity) to a base substance containing a metal oxide semiconductor material or the like, which has the cyanine structure shown in Chemical formula (1) (hereinafter referred to as cyanine compound shown in Chemical formula (1)).

The cyanine compound shown in Chemical formula (1) has a methine chain skeleton, a heterocyclic skeleton bonded with both ends of the methine chain skeleton, and anchor groups (Y1 and Y2) introduced to a nitrogen atom structuring the heterocyclic skeleton. The cyanine compound shown in Chemical formula (1) has the anchor groups and a cyano group introduced to the methine chain skeleton. Thereby, in the case where the dye is supported by the base substance, physical distance between the cyano group and the base substance becomes close, and interaction is generated between an unshared electron pair of the cyano group introduced to the methine chain and the base substance. In result, resistance at the time of electron injection from the cyanine compound to the support body is decreased. Accordingly, electron injection efficiency to the base substance containing, for example, the metal oxide semiconductor material is increased. In addition, fixation characteristics to the base substance are improved. Thus, in the case where the cyanine compound shown in Chemical formula (1) is used as a dye of a dye-sensitized photoelectric conversion device, the cyanine compound shown in Chemical formula (1) contributes to improving conversion efficiency. Even if a mirror image isomer or a diastereomer of the cyanine compound shown in Chemical formula (1) is used, similar effect is able to be obtained as long as the mirror image isomer thereof or the diastereomer thereof has the structure shown in Chemical formula (1).

[Formula 5]

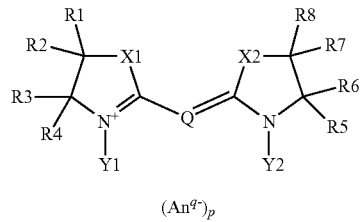

(1)

(An$^{q-}$)$_p$ (R1 to R8 are respectively and independently a hydrogen atom, a hydroxyl group, an alkyl group, an alkoxy group, an alkyl group having one or more substituent groups, an alkoxy group having one or more substituent groups, or the group expressed by Chemical formula (2). At least one of R1 and R2 and at least one of R3 and R4; and at least one of R5 and R6 and at least one of R7 and R8 may be respectively detached to form an unsaturated bond, or may be respectively linked with each other to form a ring structure. Y1 and Y2 are an anchor group. Q is a linkage group that has a methine chain with carbon atomicity from 1 to 7 both inclusive as a skeleton and that has one or more cyano groups. X1 is a group expressed by —C(R9)(R10)— or —N(R11)—, a sulfur atom, an oxygen atom, a selenium atom, or a tellurium atom. X2 is a group expressed by —C(R12)(R13)— or —N(R14)—, a sulfur atom, an oxygen atom, a selenium atom, or a tellurium atom. R9 to R14 are respectively and independently a hydrogen atom, a hydroxyl group, an alkyl group, an alkoxy group, an alkyl group having one or more substituent groups, an alkoxy group having one or more substituent groups, or the group expressed by Chemical formula (2). An$^{q-}$ is an anion with q valency. q is 1 or 2, and p is a coefficient to maintain neutral electric charge.)

[Formula 6]

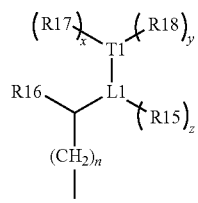

(2)

(Bond between L1 and T1 is double bond or triple bond. L1 represents a carbon atom. T1 represents a carbon atom, an oxygen atom, or a nitrogen atom. x, y, and z are respectively and independently 0 or 1 (x and y are 0 where T1 is an oxygen atom, and (y+z) is 0 or 1 where T1 is a nitrogen atom). R15 to R17 are respectively and independently a hydrogen atom, a hydroxyl group, a nitro group, a cyano group, a halogen atom, an alkyl group with carbon atomicity from 1 to 4 both inclusive, or an alkyl group with carbon atomicity from 1 to 4 both inclusive substituted by one or more halogen atoms. R18 is a hydrogen atom, a hydroxyl group, a nitro group, a cyano group, a halogen atom, an alkyl group with carbon atomicity from 1 to 4 both inclusive, an alkoxy group with carbon atomicity from 1 to 4 both inclusive, an alkyl group with carbon atomicity from 1 to 4 both inclusive substituted by one or more halogen atoms, or an alkoxy group with carbon atomicity from 1 to 4 both inclusive substituted by one or more halogen atoms. R15 and R18/R16 and R17 may be respectively linked with each other to form ring structure. n is an integer number out of 0 to 4.)

For R1 to R8 explained in Chemical formula (1), the structure thereof may be voluntary and thus may be a straight chain structure, may have a branch structure, or may include a ring structure as long as R1 to R8 are one of a hydrogen atom, a hydroxyl group, an alkyl group, an alkoxy group, an alkyl group having one or more given substituent groups, an alkoxy group having one or more given substituent groups, and the group expressed by Chemical formula (2). Further, in the case where R1 to R8 are an alkyl group, an alkoxy group, an alkyl group having one or more substituent groups, or an alkoxy group having one or more substituent groups, the carbon atomicity that structures the skeleton thereof is voluntary. As an alkyl group or an alkyl group having one or more substituent group that is introduced as R1 to R8, an alkyl group with carbon atomicity from 1 to 25 both inclusive or a group obtained by introducing one or more substituent groups to the alkyl group with carbon atomicity from 1 to 25 both inclusive is preferable. Specific examples thereof include a methyl group, an ethyl group, a propyl group, an isopropyl group, a butyl group, a secondary butyl group, a tertiary butyl group, an isobutyl group, an amyl group, an isoamyl group, a hexyl group, a cyclohexyl group, a cyclohexyl methyl group, a cyclohexyl ethyl group, a heptyl group, an isoheptyl group, a tertiary heptyl group, an n-octyl group, an isooctyl group, a tertiary octyl group, a 2-ethyhexyl group, a nonyl group, an isononyl group, a decyl group, and a group obtained by substituting part or all of hydrogen atoms included in the foregoing groups by one or more halogen atoms. As an alkoxy group or an alkoxy group having one or more substituent groups that is introduced as R1 to R8, an alkoxy group with carbon atomicity from 1 to 20 both inclusive or a group obtained by introducing one or more substituent groups to the alkoxy group with carbon atomicity from 1 to 20 both inclusive is preferable. Specific examples thereof include a methoxy group, an ethoxy group, a propyloxy group, an isopropyloxy group, a butyloxy group, a secondary butyloxy group, a tertiary butyloxy group, an isobutyloxy group, an amyloxy group, an isoamyloxy group, a tertiary amyloxy group, a hexyloxy group, a cyclohexyloxy group, a cyclohexylmethyloxy group, a cyclohexylethyloxy group, a heptyloxy group, an isoheptyloxy group, a tertiary heptyloxy group, an n-octyloxy group, an isooctyloxy group, a tertiary octyloxy group, a 2-ethyhexyloxy group, a nonyloxy group, an isononyloxy group, a decyloxy group, and a group obtained by substituting part or all of hydrogen atoms included in the foregoing groups by one or more halogen atoms.

Further, the group expressed by Chemical formula (2) introduced as R1 to R8 in Chemical formula (1) is voluntary as long as the group has the structure shown in the foregoing Chemical formula (2). Examples of the halogen atom explained in Chemical formula (2) include a fluorine atom, a chlorine atom, a bromine atom, and an iodine atom. Examples of the group shown in Chemical formula (2) include an unsaturated chain carbon hydride group such as a vinyl group (—CH=CH$_2$), an aryl group (—CH$_2$—CH=CH$_2$), a 1-propenyl group (—CH=CH—CH$_3$), an isopropenyl group (—C(CH$_3$)=CH$_2$), a 1-butenyl group (—CH=CH—CH$_2$—CH$_3$), a 2-butenyl group (—CH$_2$—CH=CH—CH$_3$), a 2-methylaryl group (—CH$_2$—C(CH$_3$)=CH$_2$), a 2-pentenyl group (—CH$_2$—CH=CH—CH$_2$—CH$_3$), an ethynyl group (—C≡CH), a 2-propynyl group (—CH$_2$—C≡CH), a 1-propynyl group (—C≡C—CH$_3$), a 2-butynyl group (—CH$_2$—C≡C—CH$_3$), and a 3-butynyl group (—CH$_2$—CH$_2$—C≡CH); an acyl group such as a formyl group, an acetyl group, a propionyl group, a butyryl group, a valeryl group, an isovaleryl group, a pivaloyl group, and a hexanoyl group, or a group having the foregoing acyl group at an end of an alkyl chain with carbon atomicity from 1 to 4 both inclusive; a group having a carboxylate ester bond (—C(=O)—O—); a group having a C=N bond; and a cyano group or a group having a cyano group at an end of an alkyl chain with carbon atomicity from 1 to 4 both inclusive. Further, in the case where R15 and R18/R16 and R17 are linked with each other to form a ring structure, examples of the group shown in Chemical formula (2) include a cyclohexenyl group or a phenethyl group; the benzyl group shown in Chemical formula (2-1), the tolylmethyl group (methylbenzyl group) shown in Chemical formula (2-2); and the groups shown in Chemical formula (2-3) to Chemical formula (2-6). Part or all of hydrogen atoms included in the foregoing groups may be substituted by one or more halogen atoms.

[Formula 7]

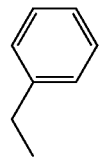

(2-1)

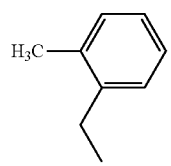

(2-2)

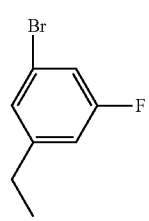

(2-3)

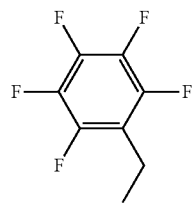

(2-4)

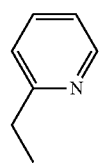

(2-5)

-continued

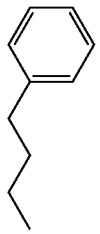
(2-6)

Further, as described above, in Chemical formula (1), at least one of R1 and R2 and at least one of R3 and R4 may be detached to form an unsaturated bond, or may be respectively linked with each other to form a ring structure. The same thing is applied to at least one of R5 and R6 and at least one of R7 and R8. Examples of the ring structure formed by linkage in R1 to R8 include a benzene ring, a naphthalene ring, a cyclohexane ring, a cyclobutane ring, a cyclopentane ring, a cyclohexane ring, a cycloheptane ring, a piperidine ring, a piperazine ring, a pyrrolidine ring, a morpholine ring, a thiomorpholine ring, a pyridine ring, a pyradine ring, a pyrimidine ring, a pyridazine ring, a triazine ring, a quinoline ring, an isoquinoline ring, an imidazole ring, an oxazole ring, and an imidazolidine ring. In addition, the ring structure may be a more condensed ring structure, or may have one or more substituent groups. Specially, as the ring structure formed by linkage in R1 to R8, a benzene ring, a naphthalene ring, a benzene ring having one or more substituent groups, or a naphthalene ring having one or more substituent groups is preferable.

Y1 and Y2 explained in Chemical formula (1) are voluntary as long as Y1 and Y2 are an anchor group that gives a compound chemical or electrostatic affinity and binding ability in relation to the base substance. Examples of Y1 and Y2 include the group expressed by Chemical formula (5). For R19 expressed in Chemical formula (5), the structure thereof and the carbon atomicity thereof may be voluntary as long as R19 is an alkylene group. Further, Z1 is a functional group to bond with the base substance. Examples of Z1 include a carboxylic acid group, a sulfonic acid group, a phosphoric group, a carboxylic acid ion group, a sulfonic acid ion group, and a phosphoric ion group. Specially, it is preferable that the carbon atomicity of R19 in Chemical formula (5) is from 1 to 4 both inclusive and Z1 is the carboxylic acid group or the carboxylic acid ion group. In particular, it is preferable that the carbon atomicity of R19 in Chemical formula (5) is 2, and Z1 is the carboxylic acid group or the carboxylic acid ion group, that is, a group expressed by —$CH_2$—$CH_2$—C(=O)—OH or a group expressed by —$CH_2$—$CH_2$—C(=O)—$O^-$. The carboxylic acid group and the carboxylic acid ion group are a functional group that has high binding ability in relation to the base substance and has high electron withdrawing characteristics. Thus, by combining the carboxylic acid group or the carboxylic acid ion group with R19 with the foregoing carbon atomicity, electron injection efficiency and fixation characteristics are more improved.

[Formula 8]

—R19—Z1  (5)

(R19 is an alkylene group, and Z1 is an acid group or a group obtained by ionizing the acid group.)

X1 and X2 explained in Chemical formula (1) are voluntary as long as X1 and X2 are one of the foregoing bivalent groups. In the case where X1 and X2 are a carbon atom having a hydrogen atom or a substituent group (—C(R9)(R10)—, —C(R12)(R13)—), or a nitrogen atom having a hydrogen atom or a substituent group (—N(R11)—, —N(R14)—), specific examples of R9 to R14 include groups similar to those of the foregoing R1 to R8. Specially, R9 to R14 are preferably a sterically bulky group so that the steric size of the entire molecule becomes large. Thereby, molecules hardly form an association body. In addition, in the case where the dye is supported by the base substance, the ratio of the association body that hardly contributes to electron injection into the base substance is decreased. Thus, the ratio of electron injection amount to the base substance in relation to light absorption amount is increased, and fixation characteristics and electron injection efficiency are more improved. Accordingly, in the case where the cyanine compound is used as a dye for a dye-sensitized photoelectric conversion device, the compound decreases the ratio of the association body that hardly contributes to photoelectric conversion in the dye, and thus the compound further contributes to improving conversion efficiency. Specifically, out of the groups shown in Chemical formula (2), the groups having a branch structure or having a ring structure and an alkyl group with carbon atomicity from 6 to 25 both inclusive are preferable, since thereby formation of the association body is more inhibited.

Q explained in Chemical formula (1) is voluntary as long as Q is a linkage group that has a methine chain (from monomethine to heptamethine) with carbon atomicity from 1 to 7 both inclusive as a skeleton and that has one or more cyano groups. Q may further have substituent groups, or the substituent groups may be bonded with each other to form a ring structure. The carbon atomicity of the methine chain is from 1 to 7 both inclusive for the following reason. That is, light absorption in a wide range from ultraviolet light to visible light is thereby favorably available. Examples of Q include the linkage group expressed by Chemical formula (6).

[Formula 9]

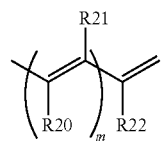
(6)

(R20 to R22 are respectively and independently a hydrogen atom or a substituent group. At least one of R20 to R22 is a cyano group. m is an integer number out of 0 to 2.)

The linkage group expressed by Chemical formula (6) represents a group in which the carbon atomicity structuring the methine chain skeleton is an odd number out of 1 to 7. In the case where the methine chain in which the carbon atomicity is an odd number is a skeleton in Q as above, the cyano group bonded with the methine chain is preferably introduced to the carbon atom as a center of the methine chain skeleton. Thereby, distance between two nitrogen atoms to which the anchor group is introduced and the carbon atom to which the cyano group is introduced becomes almost identical, and electric charge bias balance as an entire molecule becomes favorable. Thus, fixation characteristics and electron injection efficiency to the base substance are more improved. Examples of the linkage group expressed by Chemical formula (6) include the linkage groups expressed by Chemical formula (6-1) to Chemical formula (6-10).

[Formula 10]

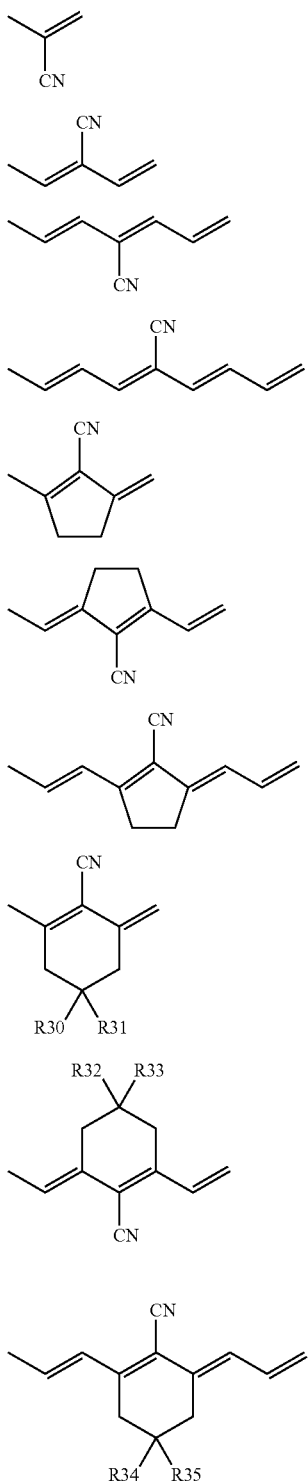

(6-1)
(6-2)
(6-3)
(6-4)
(6-5)
(6-6)
(6-7)
(6-8)
(6-9)
(6-10)

(R30 to R35 are respectively and independently a hydrogen atom, a hydroxyl group, a halogen atom, a cyano group, an aryl group with carbon atomicity from 6 to 30 both inclusive, a diphenyl amino group, an alkyl group with carbon atomicity from 1 to 8 both inclusive, or an alkoxyl group with carbon atomicity from 1 to 8 both inclusive.)

$An^{q-}$ explained in Chemical formula (1) is voluntary as long as $An^{q-}$ is a counter anion to maintain neutral electric charge of the entire cyanine compound and $An^{q-}$ is a monovalent or bivalent anion. In the case where q is 1, examples of anion (monovalent anion: $An^-$) include a halide ion such as a fluoride ion ($F^-$), a chloride ion ($Cl^-$), a bromide ion ($Br^-$), and an iodide ion ($I^-$); an inorganic anion such as a hexafluorophosphate ion ($PF_6^-$), a hexafluoroantimonate ion ($SbF_6^-$), a perchlorate ion ($ClO_4^-$), a tetrafluoroborate ion ($BF_4^-$), a chlorate ion, and a thiocyanate ion; an organic sulfonate anion such as a benzene sulfonate ion, a toluene sulfonate ion, a trifluoromethene sulfonate ion, a diphenylamine-4-sulfonate ion, a 2-amino-4-methyl-5-chlorobenzene sulfonate ion, a 2-amino-5-nitrobenzene sulfonate ion, an N-alkyldiphenylamine-4-sulfonate ion, and an N-aryldiphenylamine-4-sulfonate ion; an organic phosphate anion such as an octyl phosphate ion, a dodecyl phosphate ion, an octadecyl phosphate ion, a phenylphosphate ion, a nonylphenyl phosphate ion, and a 2,2'-methylene bis(4,6-di-t-buthyphenyl)phosphonate ion; a bistrifluoromethylsulfonylimide ion; a bisperfluorobutanesulfonylimide ion; a perfluoro-4-ethylcyclohexane sulfonate ion; a tetrakis(pentafluorophenyl) borate ion; and a tris(fluoroalkylsulfonyl)carbo anion. In the case where q is 2, examples of anion (bivalent anion: $An^{2-}$) include a sulfate ion ($SO_4^{2-}$), a benzenedisulfonate ion, and a naphthalene disulfonate ion. Further, p explained in Chemical formula (1) is a coefficient to maintain neutral electric charge as the entire cyanine compound shown in Chemical formula (1), and may be 0. In the case where p is 0, for example, one of Y1 and Y2 in Chemical formula (1) has a monovalent ion group, a salt is formed in a molecule which is to be so-called internal salt. Further, in the case where p is 1, $An^{q-}$ becomes An as a monovalent anion, and salt is formed to maintain neutral electric charge as the entire compound. Further, in the case where $An^{q-}$ is $An^{2-}$ as a bivalent anion, p is ½. That is, p is 0 or 1/q.

The cyanine compound shown in Chemical formula (1) preferably has the structure shown in the foregoing Chemical formula (3), since thereby the foregoing effect is demonstrated more than in the case of using a compound not having the structure shown in Chemical formula (3) (for example, a compound in which both tetrocyclic skeletons bonded with both ends of a methine chain include an oxazole skeleton, a thiazole skeleton, an imidazole skeleton, tellurazole skeleton, a selenazole skeleton or the like). The compound having the structure shown in the foregoing Chemical formula (3) (hereinafter referred to as the compound shown in Chemical formula (3)) is a compound in which in Chemical formula (1), R1 to R4 are linked with each other to form a ring structure (ring A) and X1 is a bivalent group expressed by —C(R9)(R10)—. That is, the structure shown in Chemical formula (3) represents the cyanine compound shown in Chemical formula (1) in the case where at least one of tetrocyclic skeletons bonded with both ends of the methine chain is an indolenine skeleton. Thus, descriptions for R5 to R10, X2, R12 to R14, Y1, Y2, and $(An^{q-})_p$ explained in Chemical formula (1) are similarly applied for R5 to R10, X2, R12 to R14, Y1, Y2, and $(An^{q-})_p$ explained in Chemical formula (3).

[Formula 11]

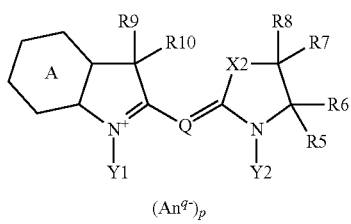

(3)

$(An^{q-})_p$ (R5 to R10 are respectively and independently a hydrogen atom, a hydroxyl group, an alkyl group, an alkoxy group, an alkyl group having one or more substituent groups, an alkoxy group having one or more substituent groups, or the group expressed by the foregoing Chemical formula (2). At least one of R5 and R6 and at least one of R7 and R8 may be respectively detached to form an unsaturated bond, or may be respectively linked with each other to form a ring structure. Y1 and Y2 are an anchor group. Q is a linkage group that has a methine chain with carbon atomicity from 1 to 7 both inclusive as a skeleton and that has one or more cyano groups. X2 is a group expressed by —C(R12)(R13)— or —N(R14)—, a sulfur atom, an oxygen atom, a selenium atom, or a tellurium atom. R12 to R14 are respectively and independently a hydrogen atom, a hydroxyl group, an alkyl group, an alkoxy group, an alkyl group having one or more substituent groups, an alkoxy group having one or more substituent groups, or the group shown in the foregoing Chemical formula (2). The ring A is a benzene ring, a naphthalene ring, a benzene ring having one or more substituent groups, or a naphthalene ring having one or more substituent groups. $An^{q-}$ is an anion with q valency. q is 1 or 2, and p is a coefficient to maintain neutral electric charge.)

The ring A explained in Chemical formula (3) is voluntary as long as a benzene ring/naphthalene ring skeleton is included. The ring A may have one or more substituent groups. The substituent group introduced to the ring A is voluntary. Examples of the substituent group include an alkyl group such as a methyl group, an ethyl group, and a butyl group; an alkoxy group such as a methoxy group and a ethoxy group; an aryl group such as a phenyl group; a group obtained by substituting part or all of hydrogen atoms included in the foregoing groups by one or more halogen atoms. Other examples of the substituent group included in the ring A include a nitro group, a cyano group, a halogen atom, an acetyl group, and a carboxylic group.

In the compound shown in Chemical formula (3), at least one of R9 and R10 is preferably a sterically bulky group, since thereby electron injection efficiency in relation to the base substance is more improved for the following reason. That is, in the case where the indolenine skeleton is included as a heterocyclic skeleton included in the cyanine structure is included as in the structure shown in Chemical formula (3), in general, a structure in which carbon atoms (and a hetero atom) structuring the methine chain skeleton and the indolenine skeleton are arrayed in the same plane, that is, a so-called structure with high planarity is included. Thus, such a cyanine structure has characteristics that each molecule is overlapped with each other to easily form an association body such as a dimer. However, in the case where the sterically bulky group is introduced as R9 or R10 as described above, the sterically bulky group exists to occupy at least one space out of the upper face side and the lower face side in relation to the plane including the methine chain skeleton and the indolenine skeleton. Thereby, the steric size of the structure with high planarity becomes large, which hardly forms an association body as the entire molecule. In the case where the dye is supported by the base substance, the ratio of the association body that hardly contributes to electron injection into the base substance is decreased. Thus, light absorption efficiency (light absorption amount per compound fixed to the base substance) is increased, and electron injection efficiency to the base substance is more improved. Accordingly, for example, in the case where the cyanine compound is used as a dye of a dye-sensitized photoelectric conversion device, the cyanine compound decreases the ratio of the association body that hardly contributes to photoelectric conversion in the dye, and thus the conversion efficiency is more improved. Specially, as the sterically bulky group, an alkyl group with carbon atomicity from 6 to 25 both inclusive is preferable, and an alkyl group with carbon atomicity from 11 to 25 both inclusive is particularly preferable, since thereby formation of the association body is more inhibited. In addition, the alkyl group with carbon atomicity from 11 to 25 both inclusive is able to be easily synthesized. Further, in the case where the alkyl group with carbon atomicity from 11 to 25 both inclusive is used as a dye of a photoelectric conversion device, productivity of the device is improved. More specifically, in the case where the carbon atomicity of the alkyl group is 6 or more, association inhibition effect becomes higher than in the case that the carbon atomicity of the alkyl group is 5 or less. In the case where the carbon atomicity of the alkyl group is 11 or more, dissolution characteristics to an organic solvent such as ethanol becomes higher than in the case that the carbon atomicity of the alkyl group is 10 or less, and a high density dye solution is able to be prepared. Meanwhile, in the case where the carbon atomicity of the alkyl group is 25 or less, synthesis becomes easier than in the case that the carbon atomicity of the alkyl group is 26 or more. If the high density dye solution is able to be prepared, in forming the photoelectric conversion device, time necessary for making a support body support a dye (absorption time) is able to be reduced, and thus productivity of the device is improved.

Specially, the compound shown in Chemical formula (3) preferably has the structure shown in the foregoing Chemical formula (4), since thereby higher effect is easily able to be obtained. The compound having the structure shown in the Chemical formula (4) (hereinafter referred to as the compound shown in Chemical formula (4)) is a compound in which in Chemical formula (3), R5 to R8 are linked with each other to form a ring structure (ring B) and X2 is a bivalent group expressed by —C(R12)(R13)—. That is, the compound shown in Chemical formula (4) represents the cyanine compound shown in Chemical formula (1) in the case where both heterocyclic skeletons bonded with both ends of a methine chain are an indolenine skeleton. Thus, descriptions for R9, R10, R12, R13, Y1, Y2, and $(An^{q-})_p$ in Chemical formula (1) are similarly applied for R9, R10, R12, R13, Y1, Y2, and $(An^{q-})_p$ explained in Chemical formula (4).

[Formula 12]

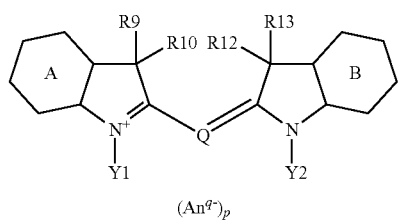

(4)

$(An^{q-})_p$ (R9, R10, R12, and R13 are respectively and independently a hydrogen atom, a hydroxyl group, an alkyl group, an alkoxy group, an alkyl group having one or more substituent groups, an alkoxy group having one or more substituent groups, or the group shown in the foregoing Chemical formula (2). Y1 and Y2 are an anchor group. Q is a linkage group that has a methine chain with carbon atomicity from 1 to 7 both inclusive as a skeleton and that has one or more cyano groups. The ring A and the ring B are respectively and independently a benzene ring, a naphthalene ring, a benzene ring having one or more substituent groups, or a naphthalene ring having one or more substituent groups. $An^{q-}$ is an anion with q valency. q is 1 or 2, and p is a coefficient to maintain neutral electric charge.)

The ring A and the ring B explained in Chemical formula (4) are similar to the ring A in Chemical formula (3). The ring A and the ring B in Chemical formula (4) are preferably a benzene ring having an electron-releasing substituent group. Thereby, in the case where the dye is supported by the base substance, if the cyanine compound absorbs light to become in excitation state, the electron-releasing substituent group pushes out an electron so that the electron is easily moved to the base substance and thus higher electron injection efficiency is able to be obtained. The anchor groups (Y1 and Y2) in this case preferably have an electron withdrawing functional group such as a carboxylic group and a carboxylic ion group. Thereby, the electron-releasing substituent group pushes out the electron and the anchor group pulls the electron, and thus electron injection efficiency in relation to the base substance bonded by the anchor group is particularly increased. As the electron-releasing substituent group introduced to the ring A and the ring B, a methoxy group is preferable.

In the compound shown in Chemical formula (4), at least one of R9, R10, R12, and R13 in Chemical formula (4) is preferably a sterically bulky group for the same reason as the reason why at least one of R9 and R10 in the foregoing Chemical formula (3) is preferably a sterically bulky group. As the sterically bulky group, an alkyl group with carbon atomicity from 6 to 25 both inclusive is preferable, and an alkyl group with carbon atomicity from 11 to 25 both inclusive is particularly preferable for the same reason as the reason explained in Chemical formula (3). In particular, R9, R10, R12, and R13 are preferably an alkyl group with carbon atomicity from 6 to 25 both inclusive. Thereby, the sterically bulky alkyl group with carbon atomicity from 6 to 25 both inclusive is introduced to occupy both spaces on the upper face side and the lower face side in relation to the plane including the methine chain skeleton and the indolenine skeleton. In result, as the entire molecule, the steric size of the structure becomes large, which hardly forms an association body. Thus, in the case where the dye is supported by the base substance, the ratio of the association body that hardly contributes to electron injection into the base substance is decreased. Thus, the ratio of electron injection amount to the base substance in relation to light absorption amount is increased, and electron injection efficiency and fixation characteristics are more improved.

Examples of the cyanine compound shown in Chemical formula (1) include the compounds expressed by Chemical formula (7) to Chemical formula (161). It is needless to say that the cyanine compound shown in Chemical formula (1) is not limited to the compounds shown in Chemical formula (7) to Chemical formula (161), but any compound is adopted as long as the compound has the cyanine structure shown in Chemical formula (1). The same is applied to Chemical formula (3) and Chemical formula (4). Further, in the compounds shown in Chemical formula (7) to Chemical formula (161), the compound in which $An^{q-}$ is $Br^-$ or $I^-$ is exemplified. However, for example, the foregoing monovalent or bivalent anions are able to be voluntarily adopted, and the same is applied to other anions.

[Formula 13]

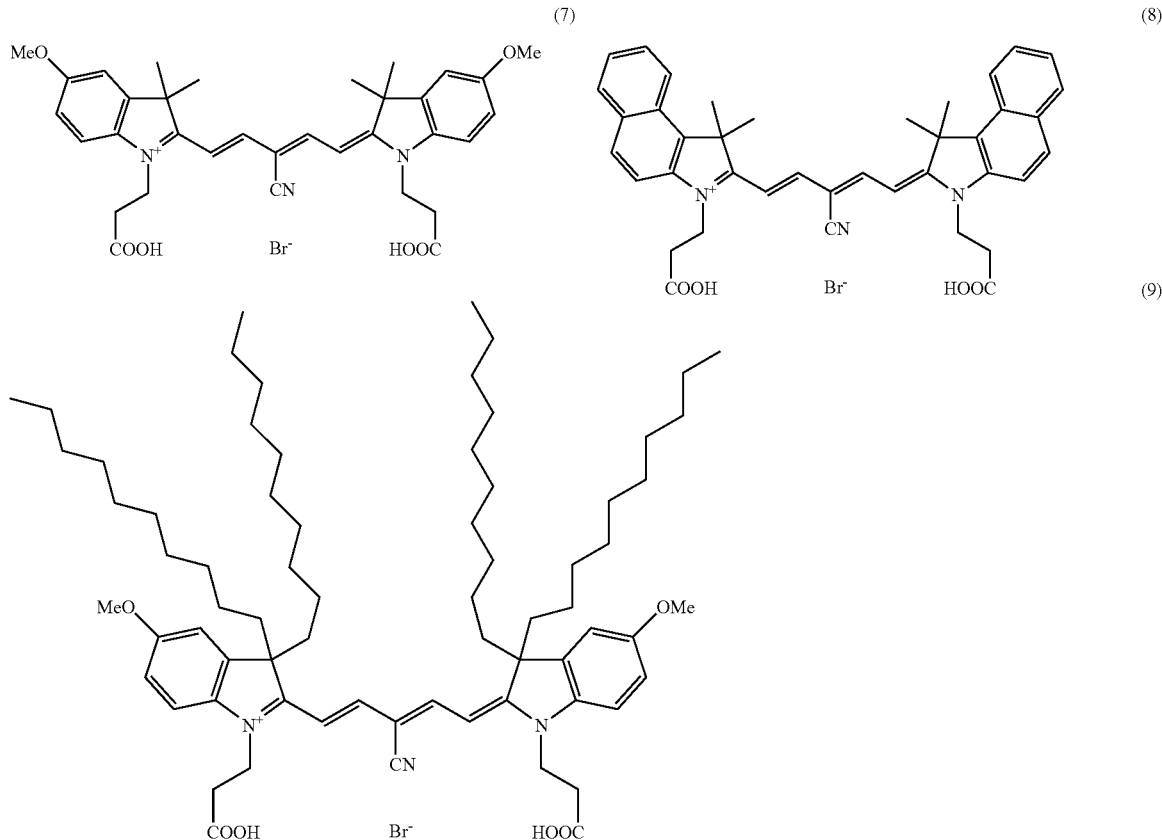

-continued
(10)
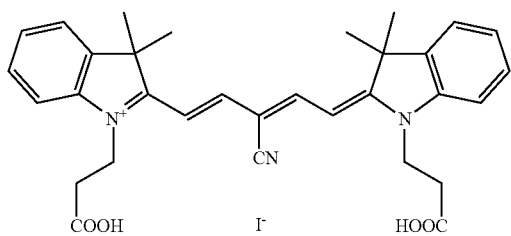
(11)
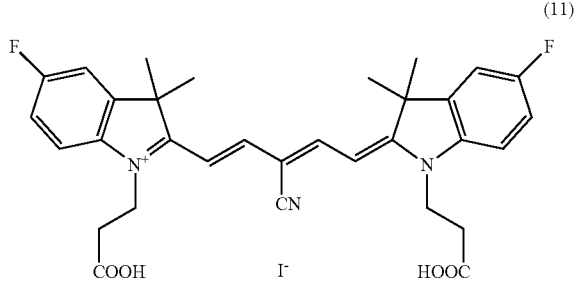
(12)
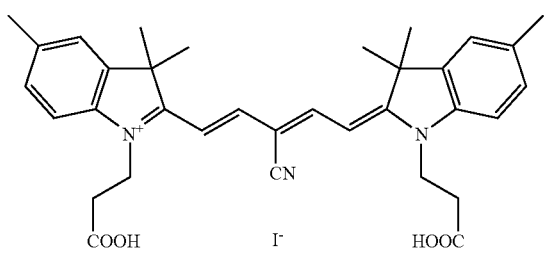
[Formula 14]
(13)
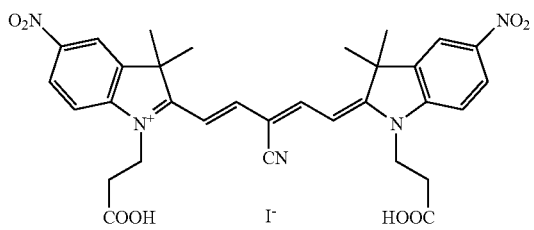
(14)
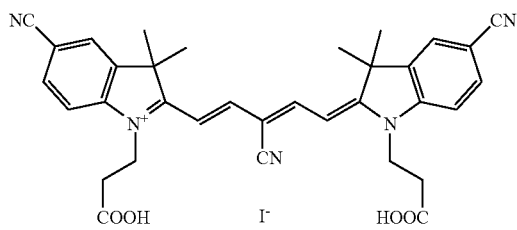
(15)
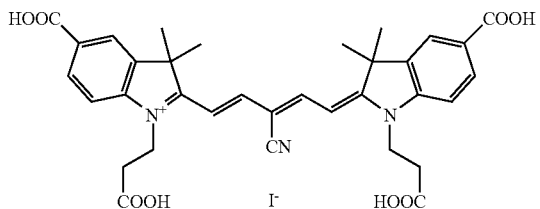
(16)
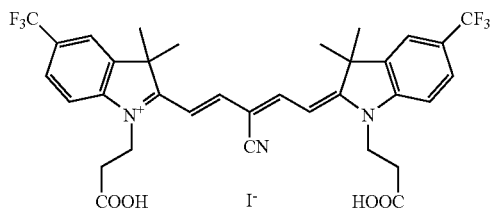
(17)
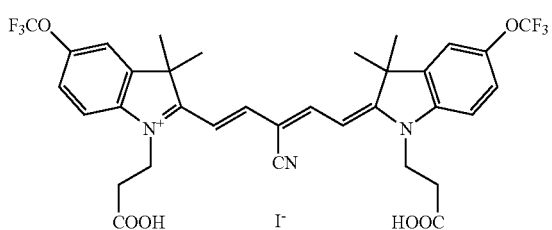
(18)
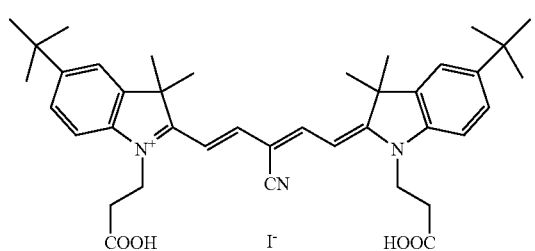
[Formula 15]
(19)
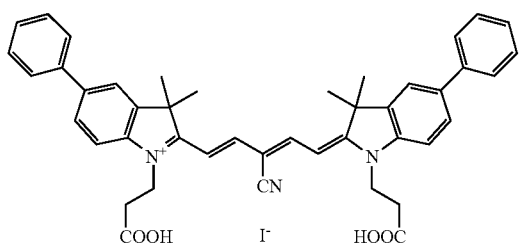
(20)
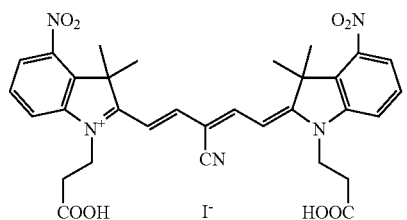

-continued
(21)
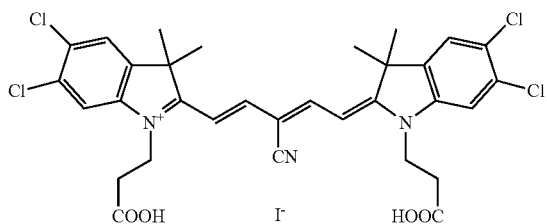
(22)
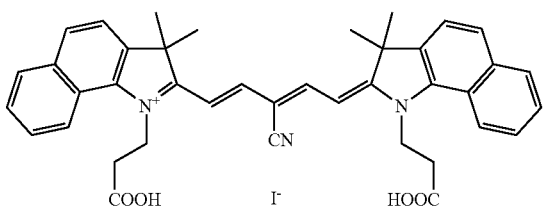
(23)
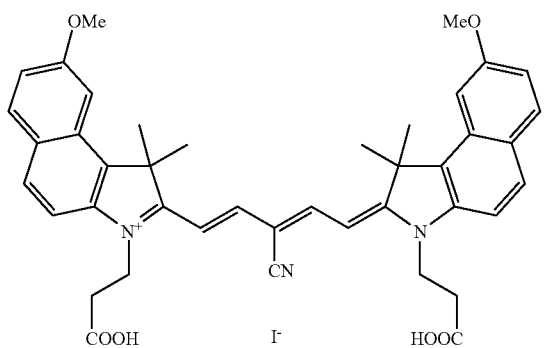
(24)
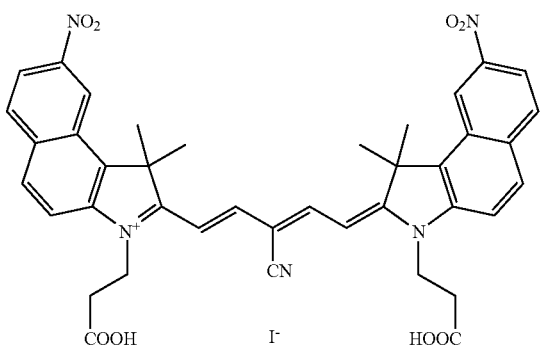
[Formula 16]
(25)
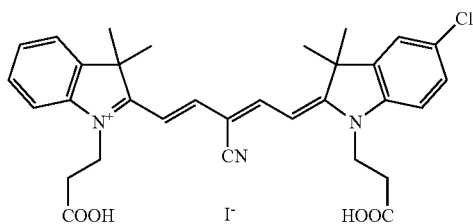
(26)
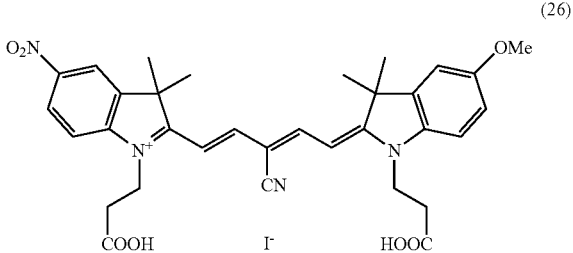
(27)
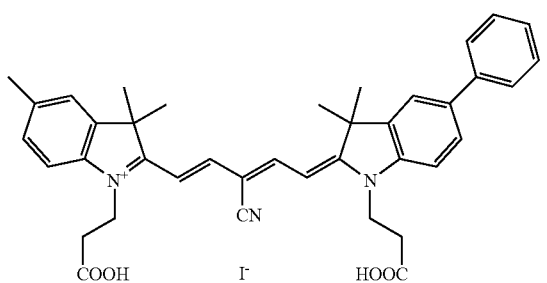
(28)
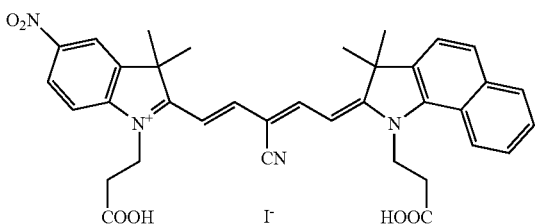
(29)
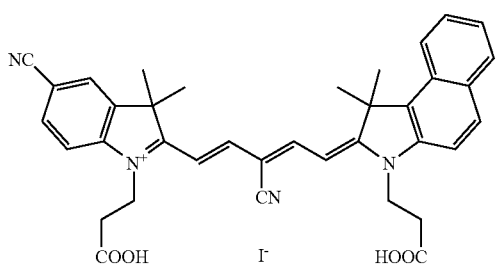
(30)
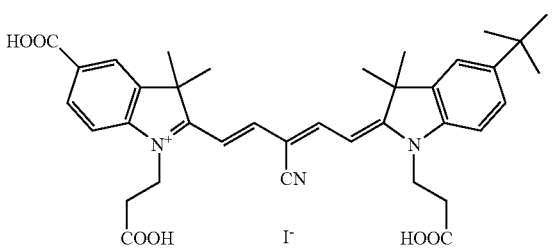

-continued
[Formula 17]
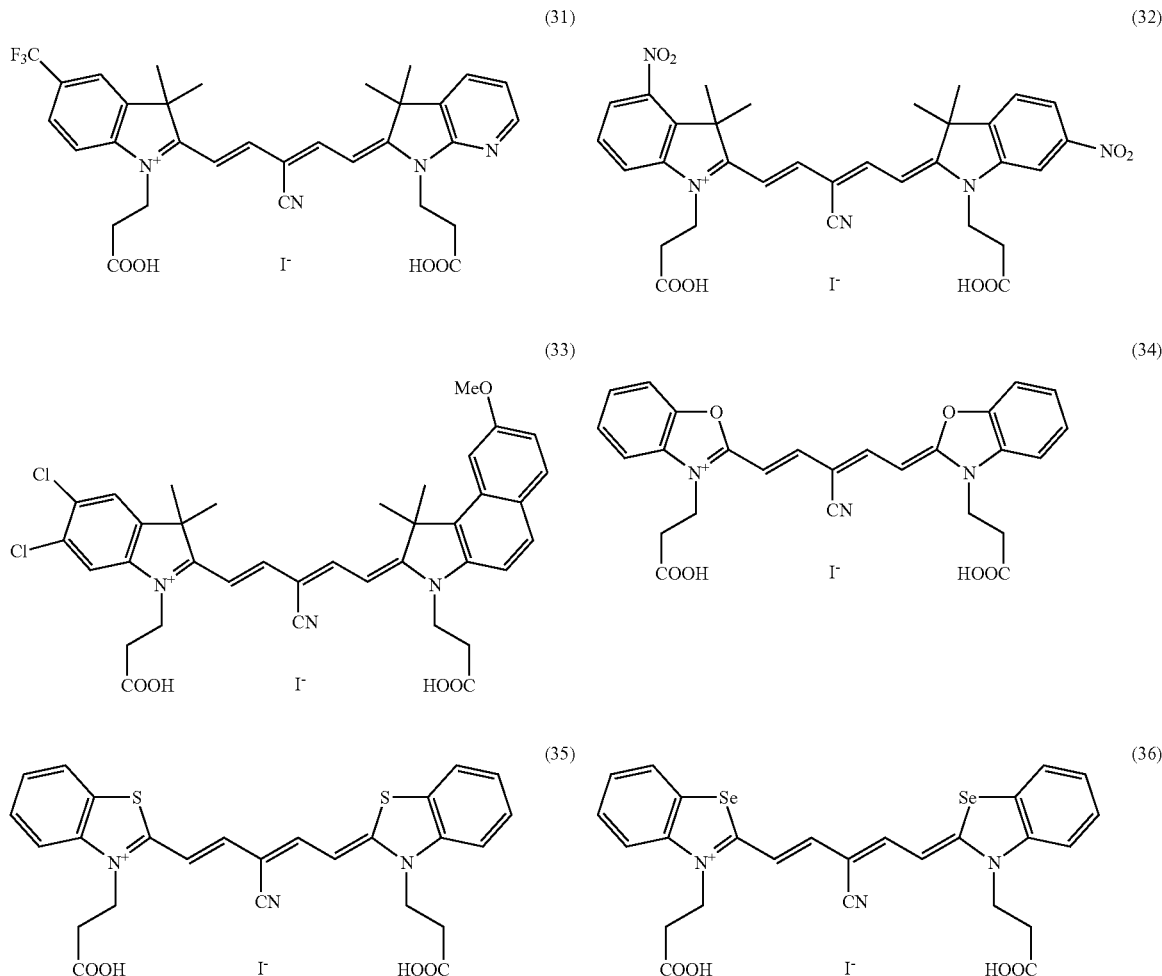
[Formula 18]
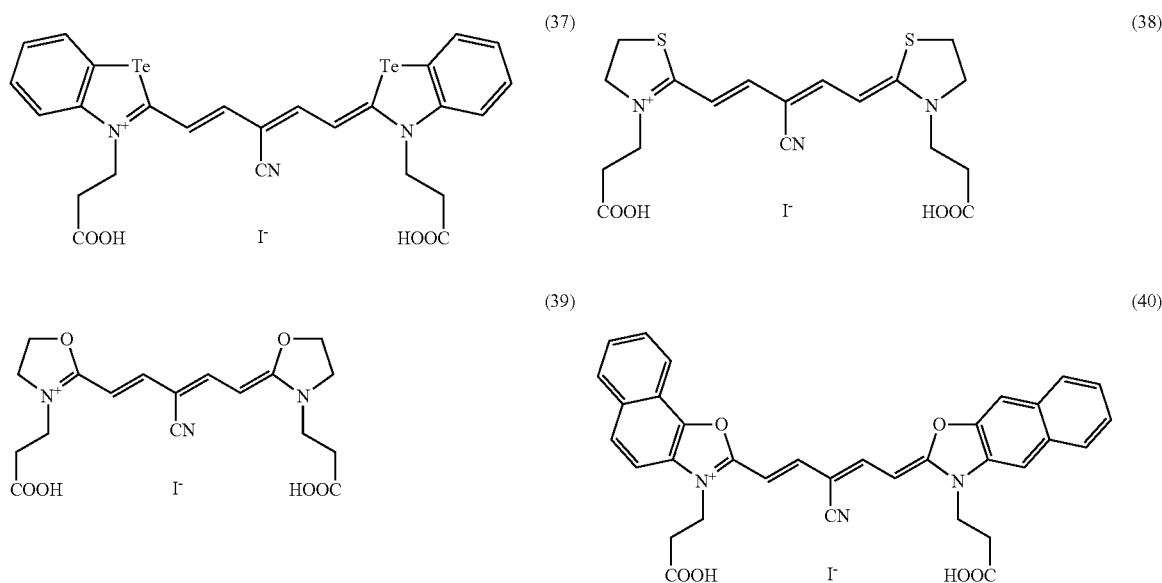

-continued
(41)
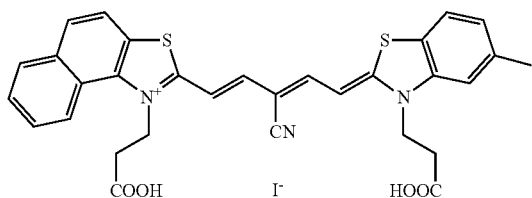
(42)
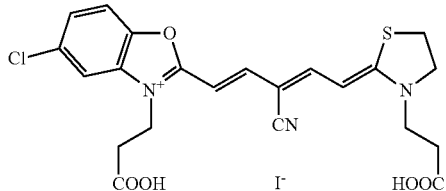
[Formula 19]
(43)
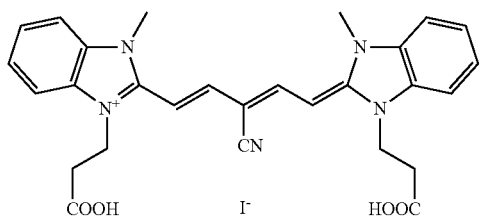
(44)
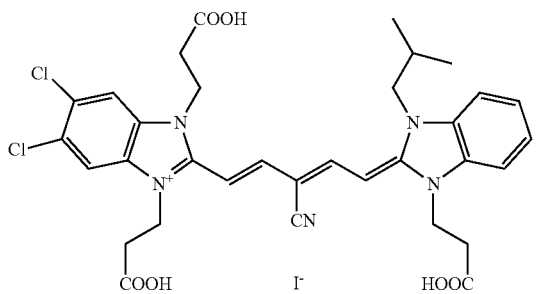
(45)
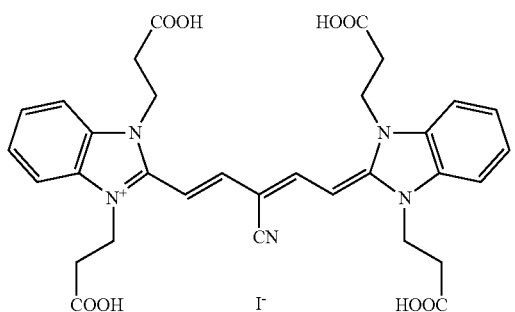
(46)
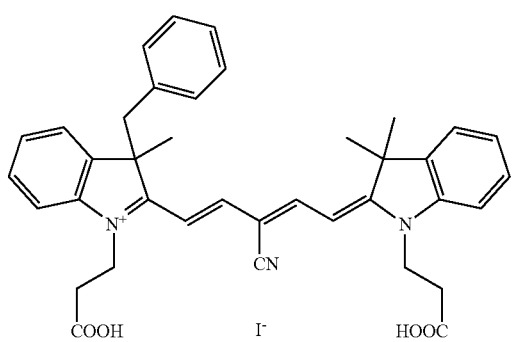
(47)
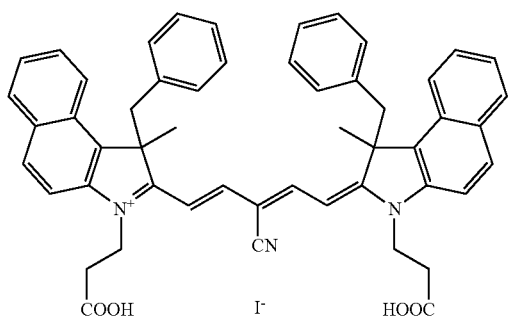
(48)
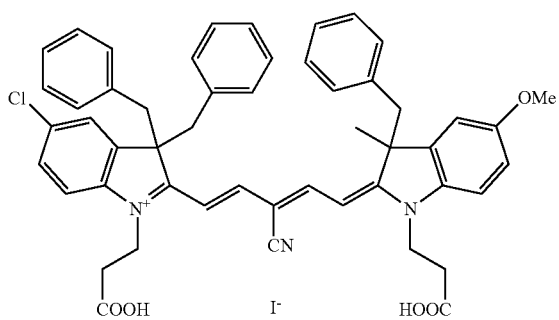
[Formula 20]
(49)
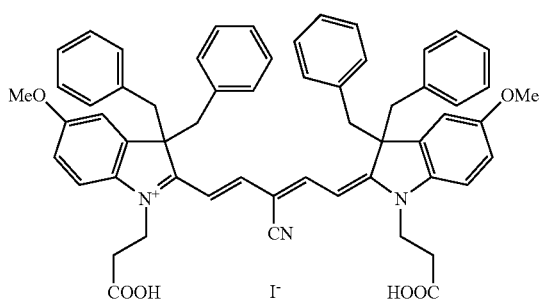
(50)
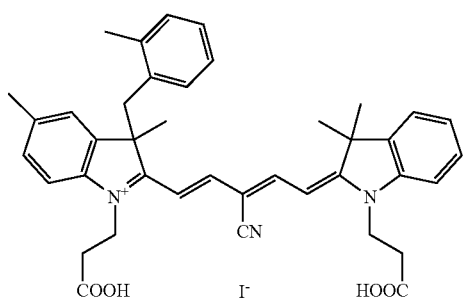

-continued
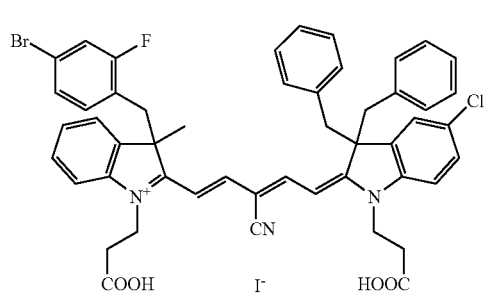
(51)
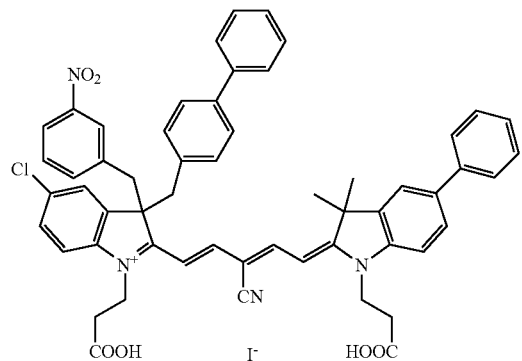
(52)
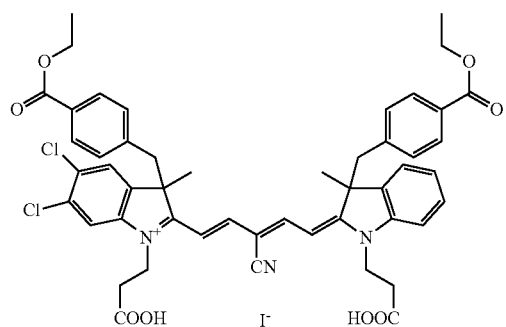
(53)
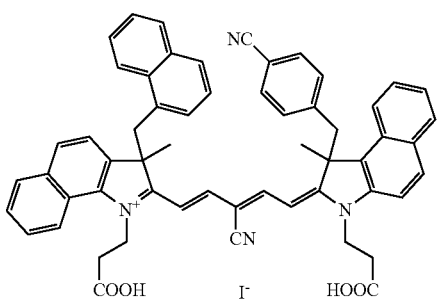
(54)
[Formula 21]
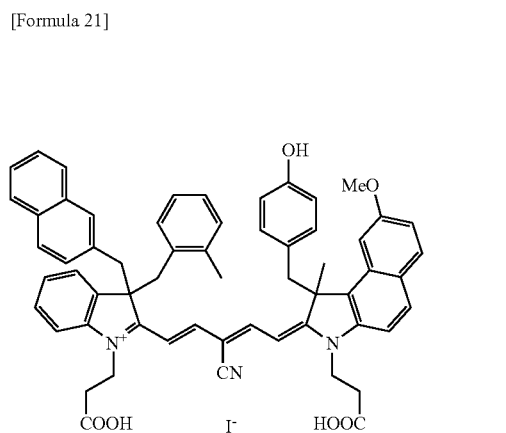
(55)
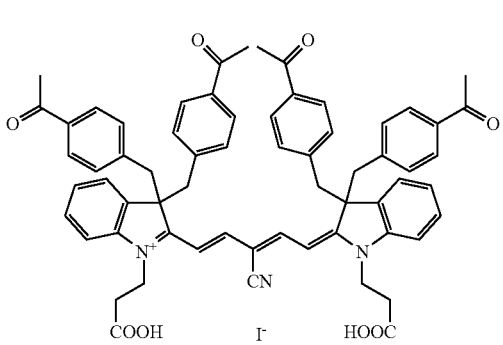
(56)
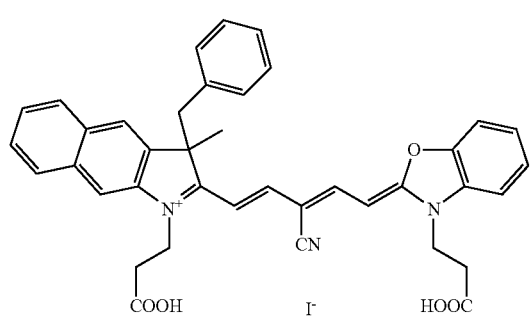
(57)
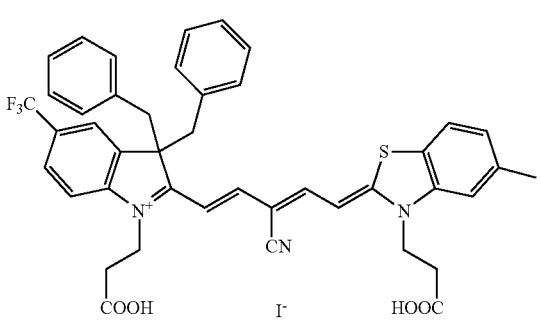
(58)

-continued
(59)
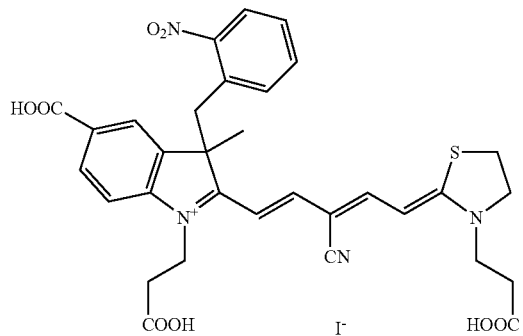
[Formula 22]
(60)
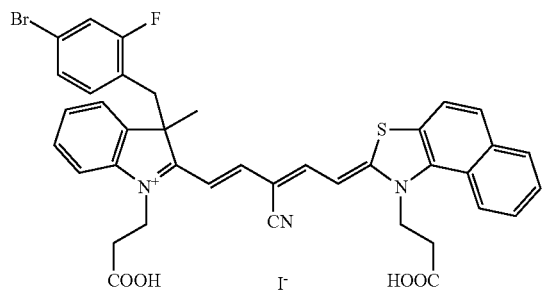
(61)
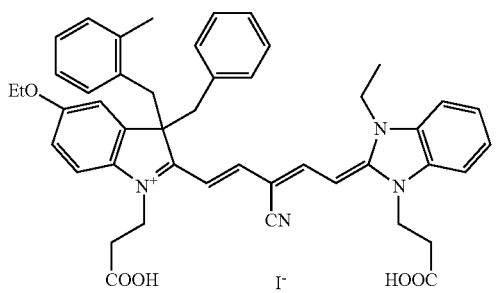
(62)
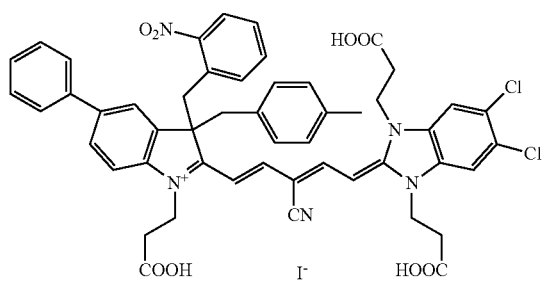
(63)
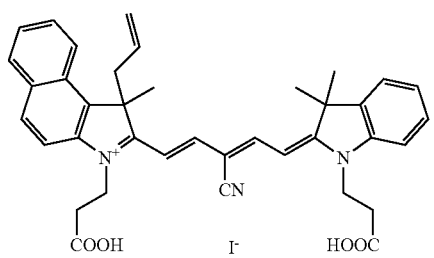
(64)
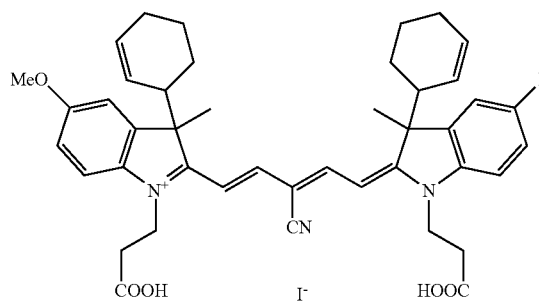
(65)
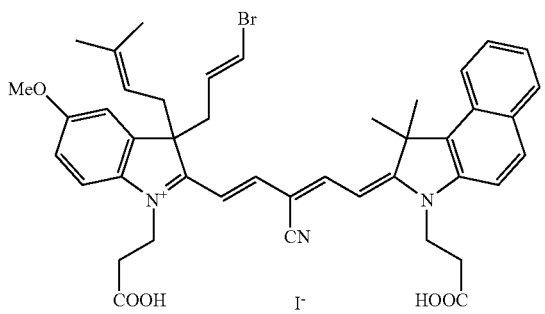

[Formula 23]
(66)
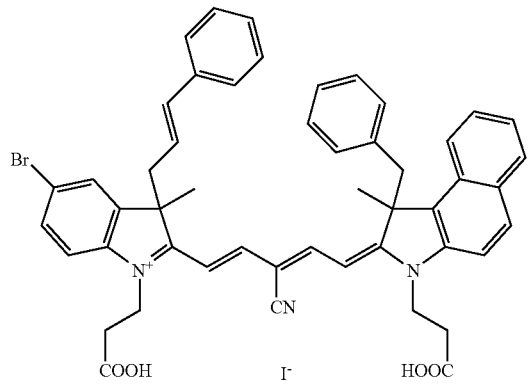
(67)
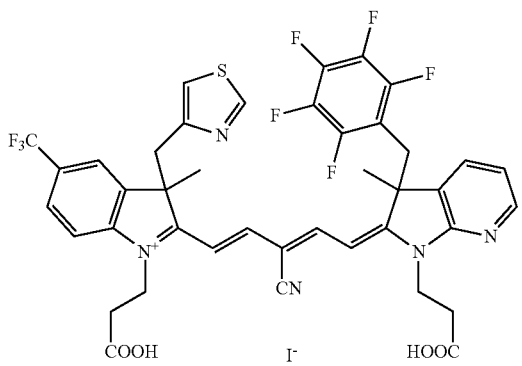
(68)
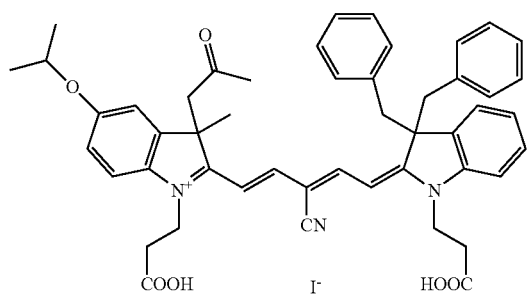
(69)
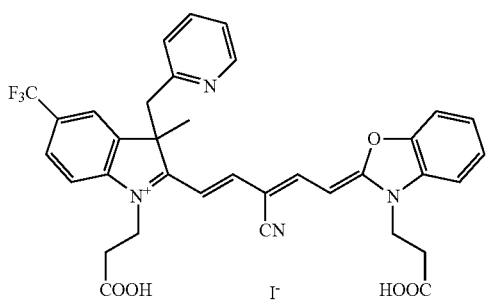
(70)
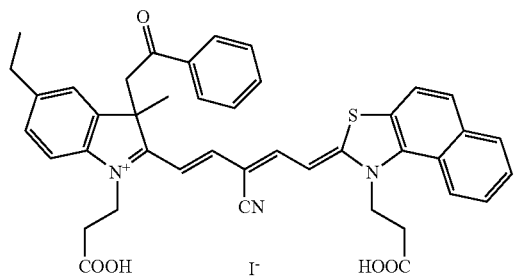
(71)
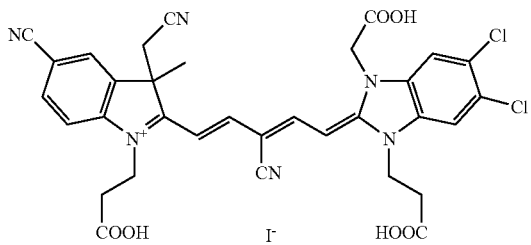
[Formula 24]
(72)
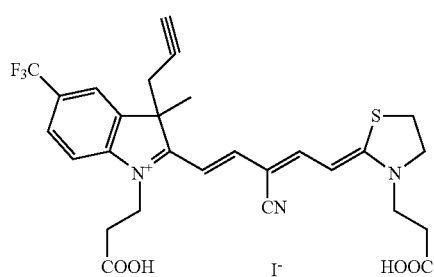
(73)
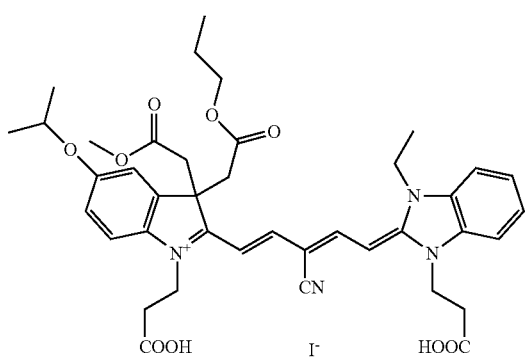

-continued
(74)
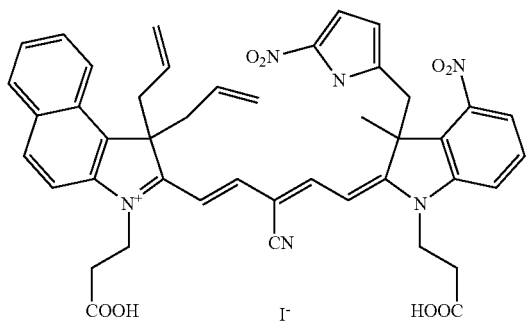
(75)
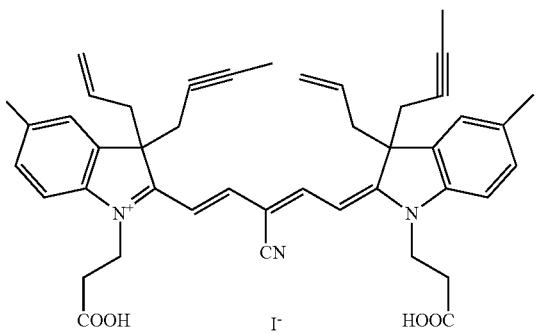
[Formula 25]
(76)
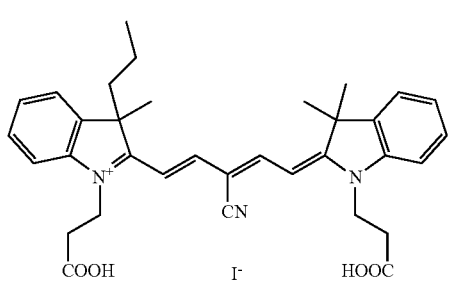
(77)
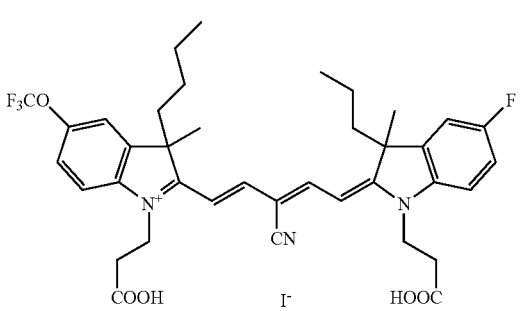
(78)
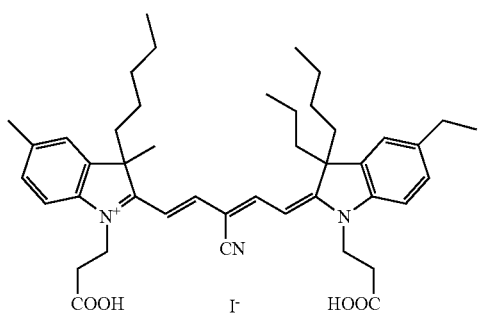
(79)
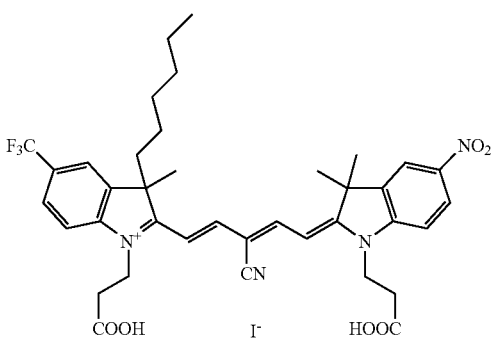
(80)
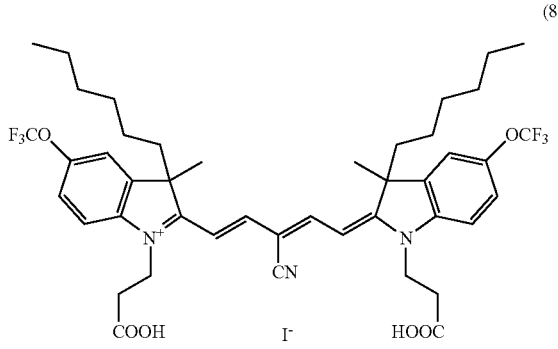
(81)
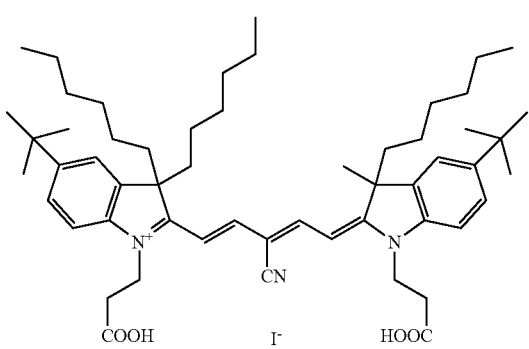

-continued
[Formula 26]
(82)
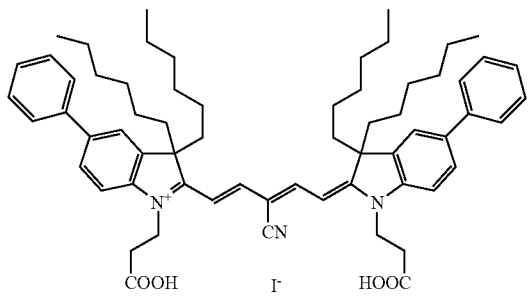
(83)
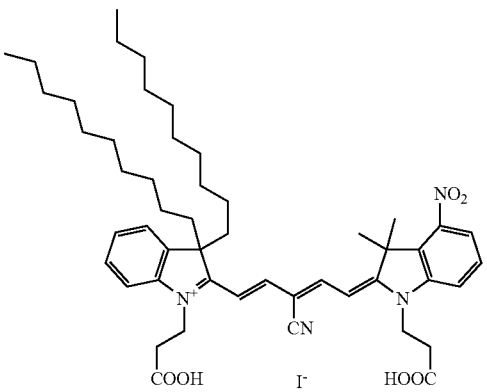
(84)
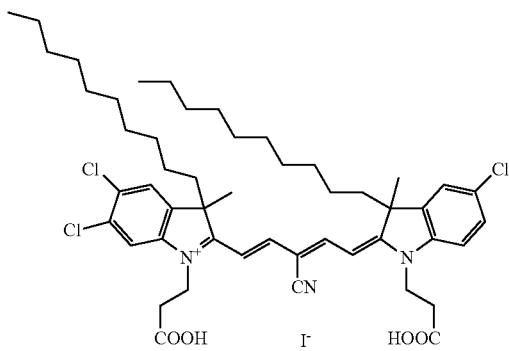
(85)
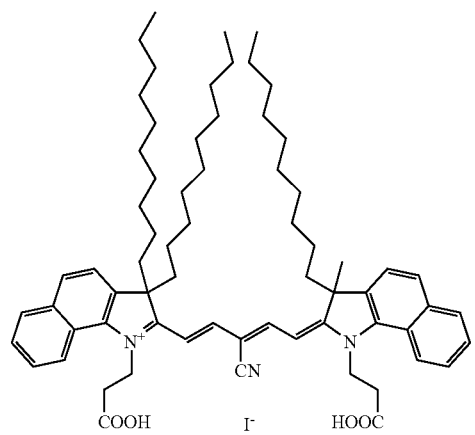
(86)
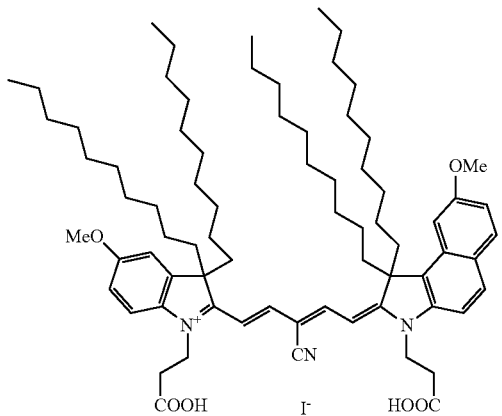
(87)
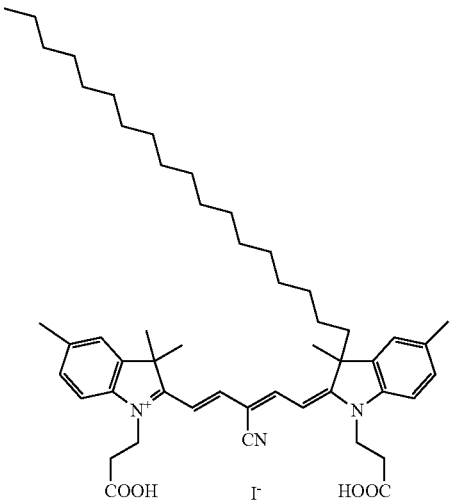

[Formula 27]
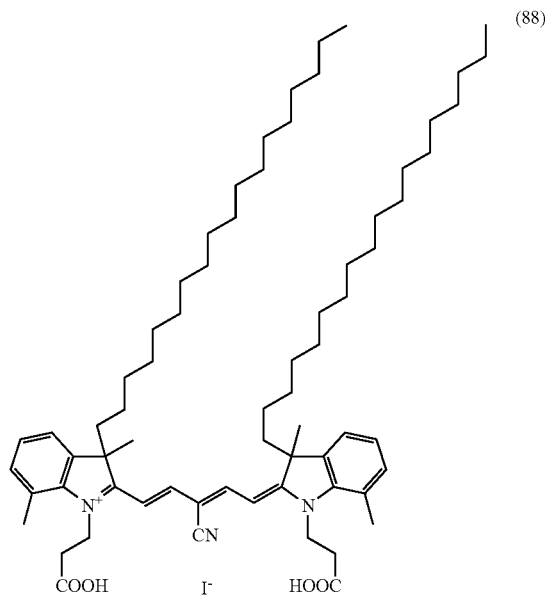
(88)
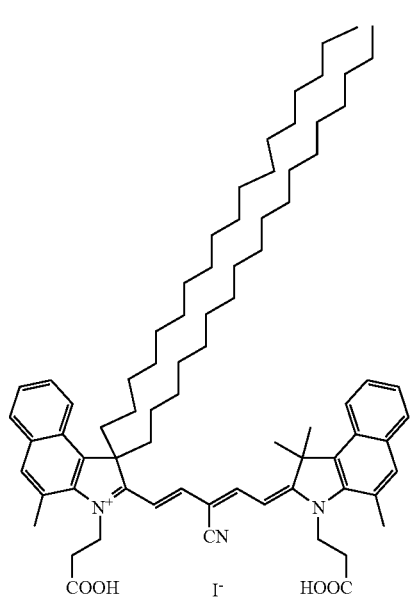
(89)
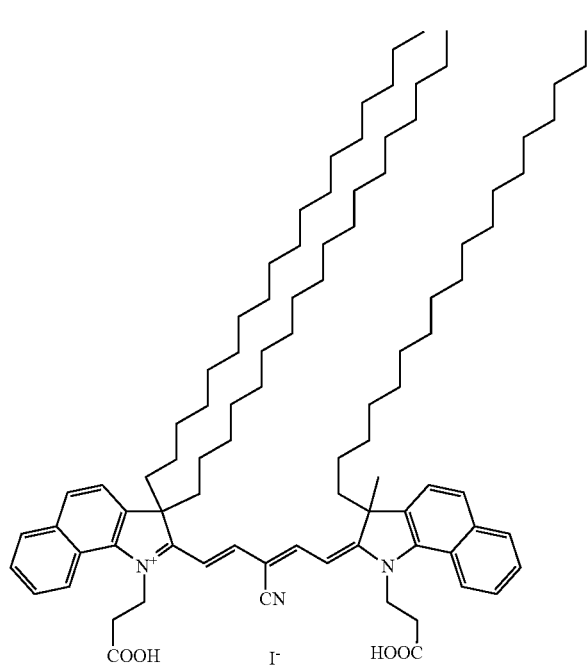
(90)

-continued
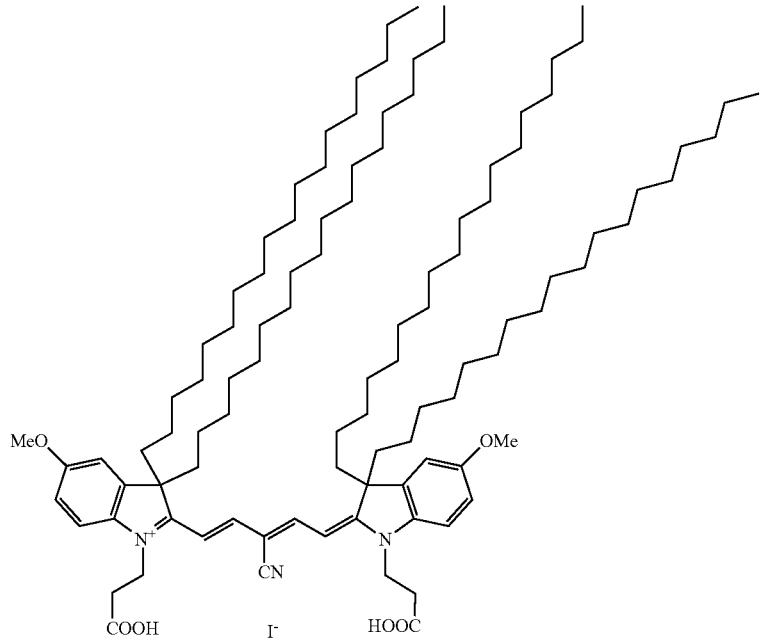
(91)
[Formula 28]
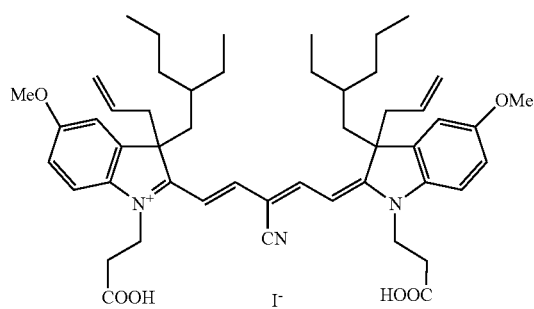
(92)
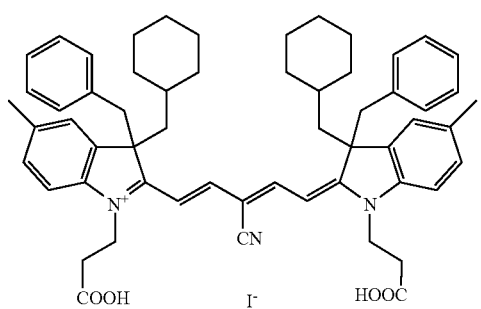
(93)
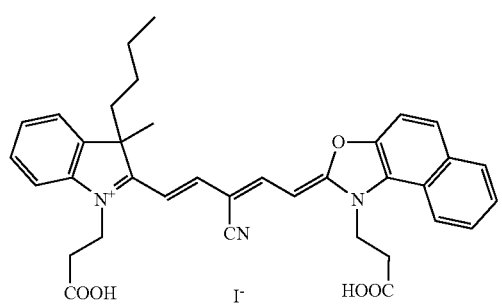
(94)
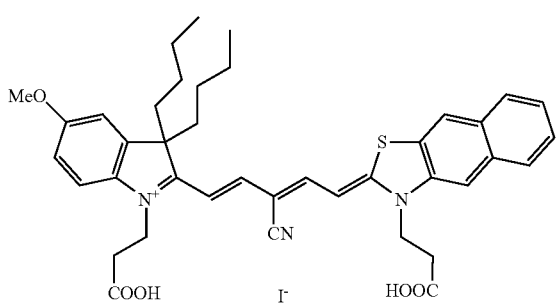
(95)

-continued
(96)
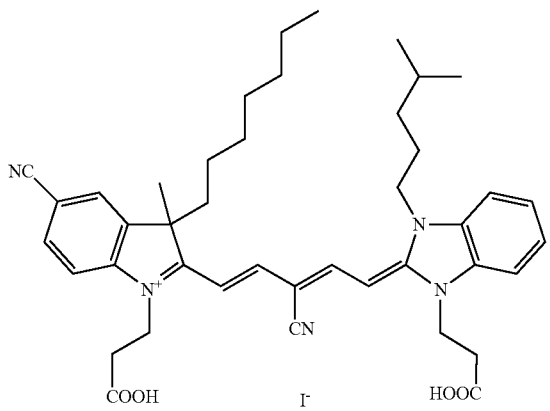
[Formula 29]
(97)
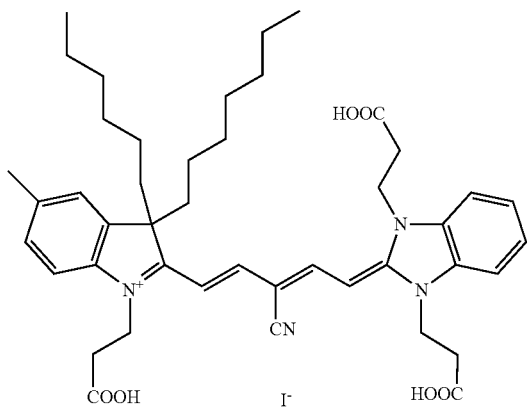
(98)
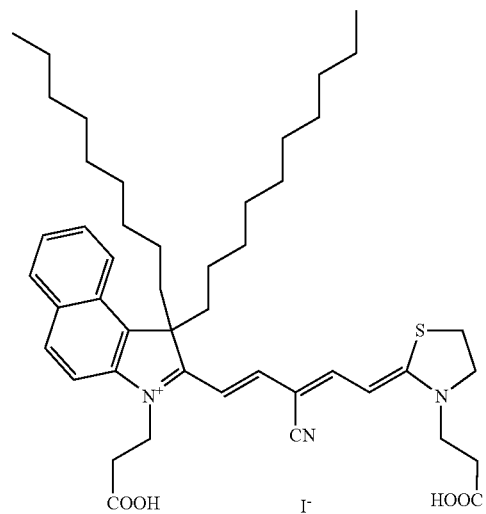
(99)
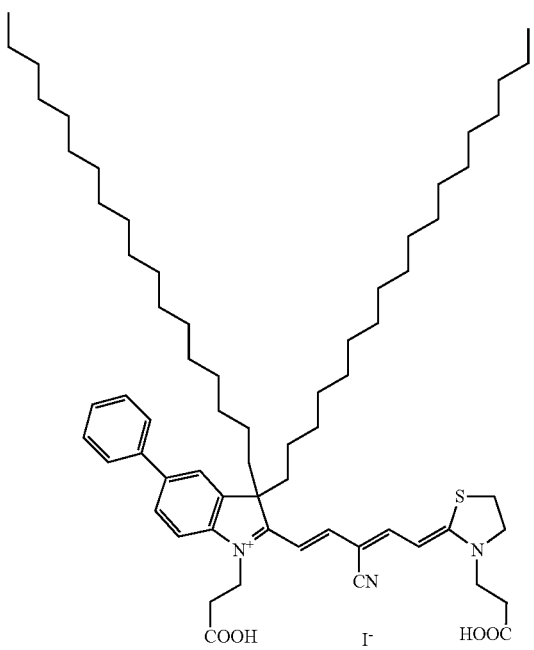
(100)
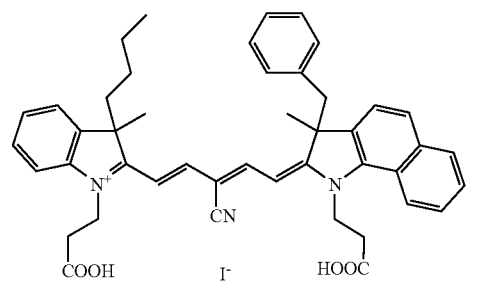

-continued
[Formula 30]
(101)
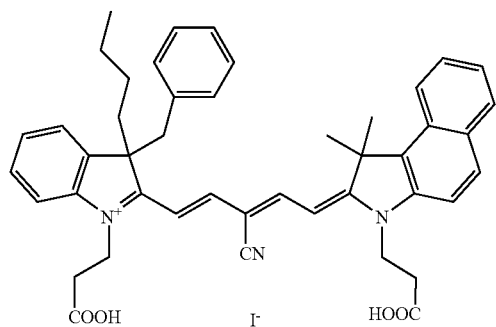
(102)
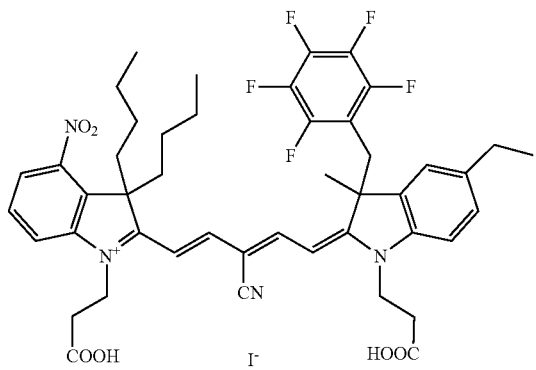
(103)
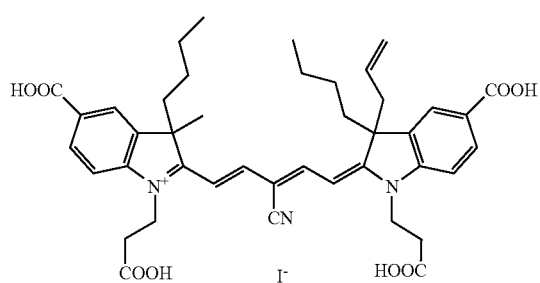
(104)
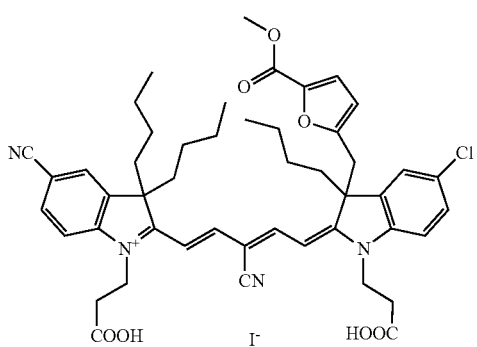
(105)
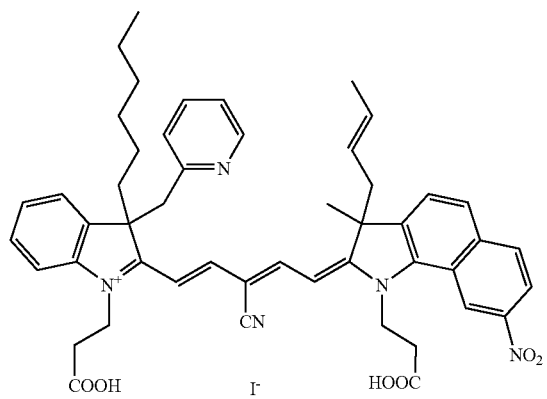
[Formula 31]
(106)
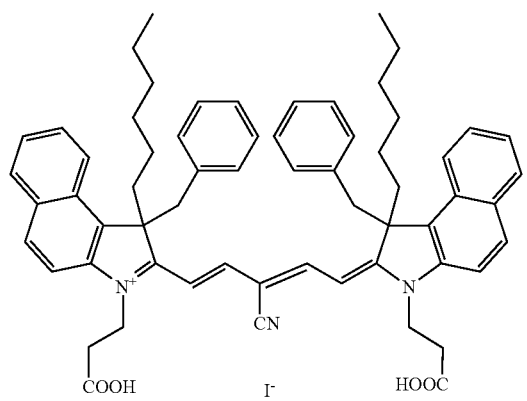
(107)
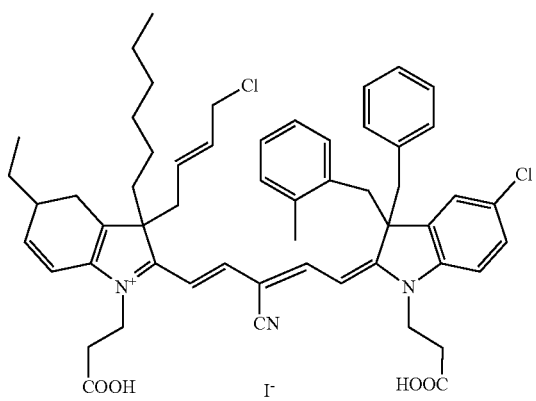

-continued
(108)
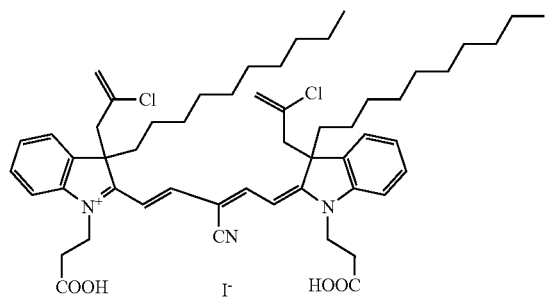
(109)
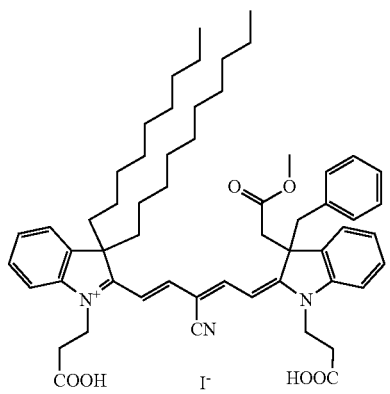
[Formula 32]
(110)
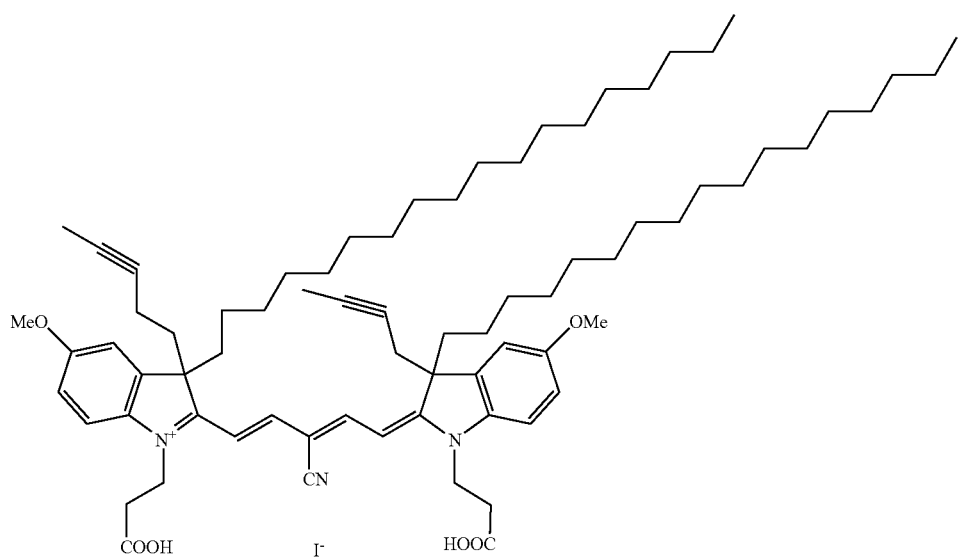
(111)
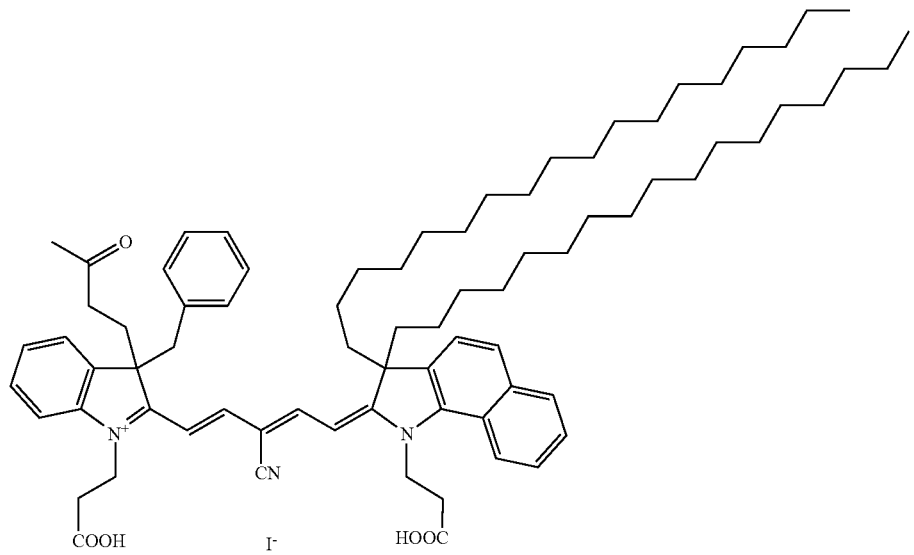

-continued
(112)
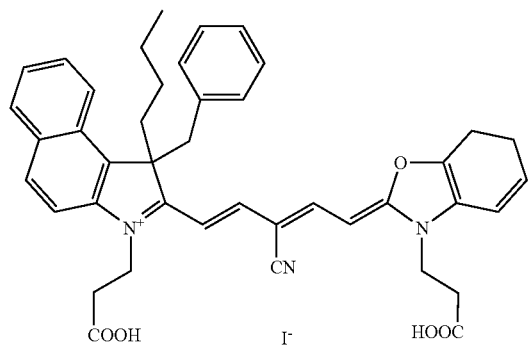
(113)
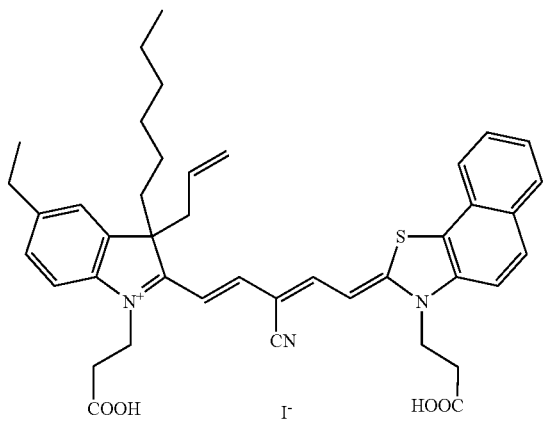
[Formula 33]
(114)
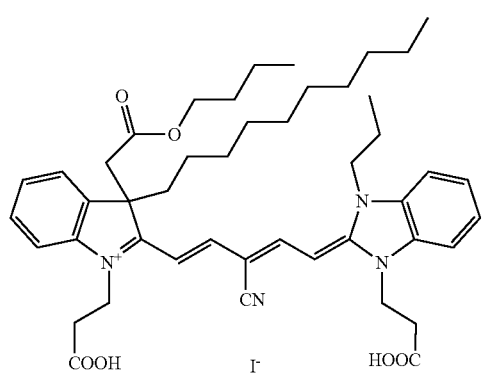
(115)
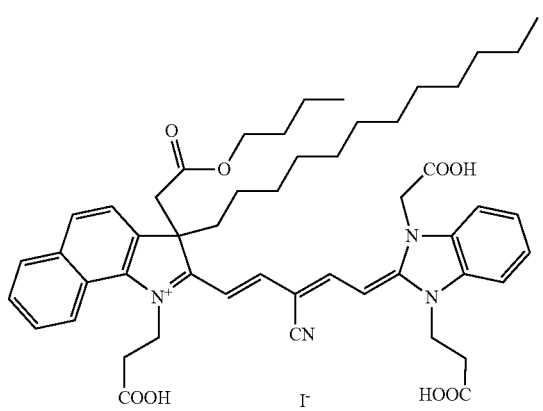
(116)
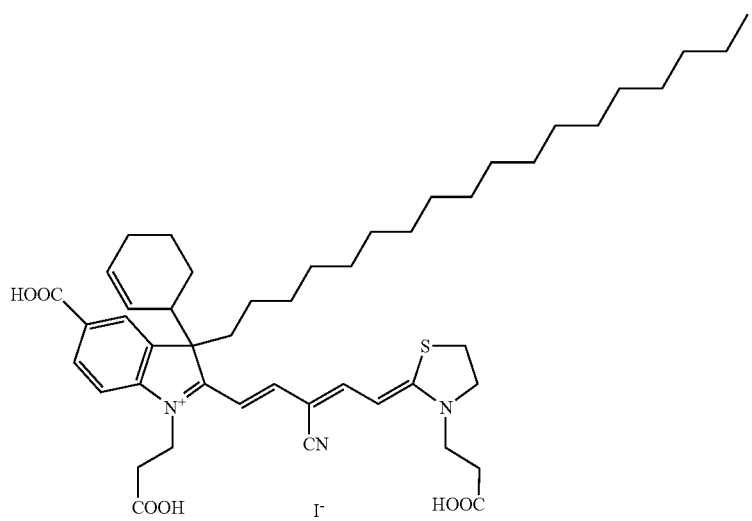

-continued
(117)
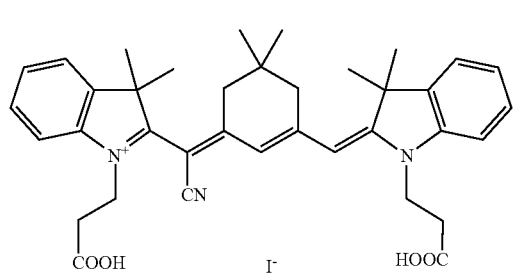
(118)
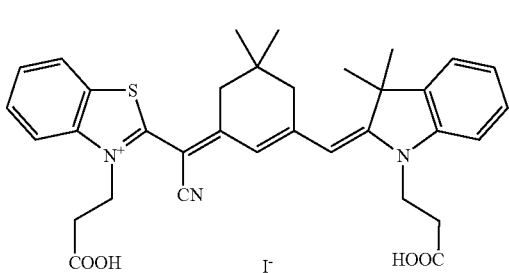
(119)
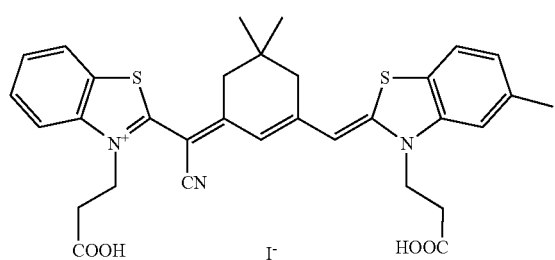
[Formula 34]
(120)
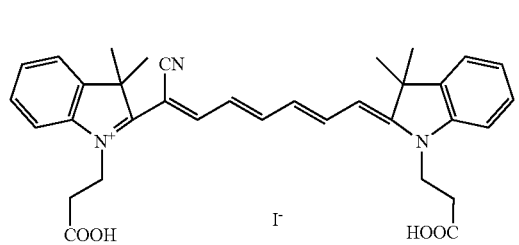
(121)
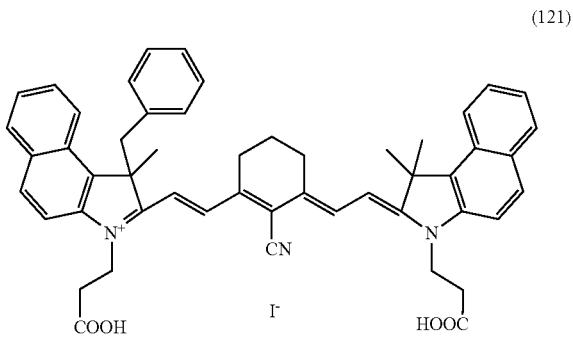
(122)
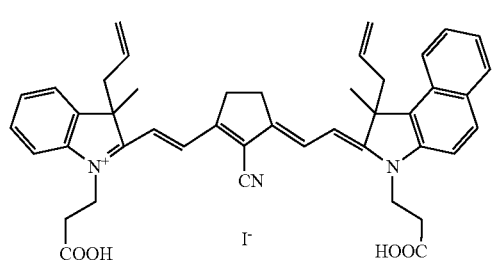
(123)
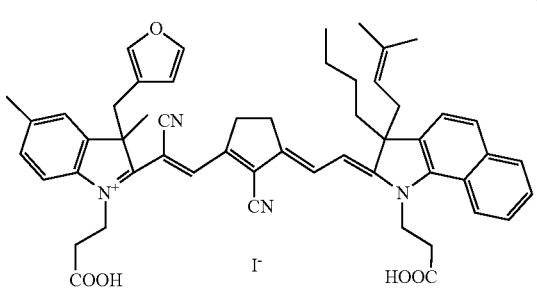

-continued
(124)
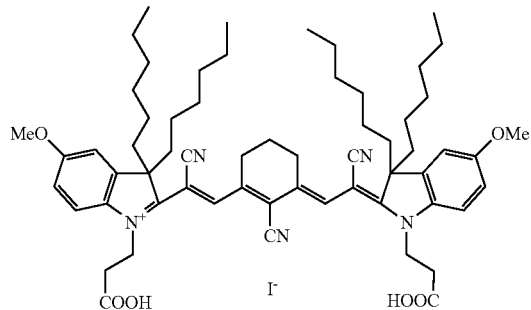
(125)
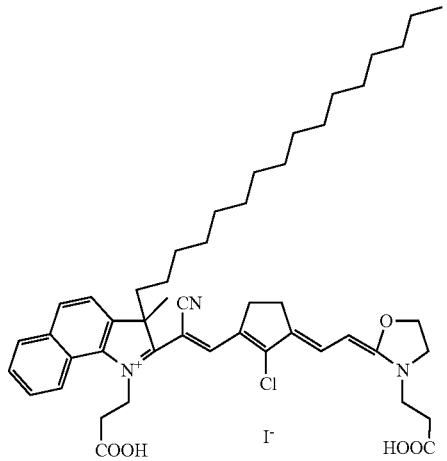
[Formula 35]
(126)
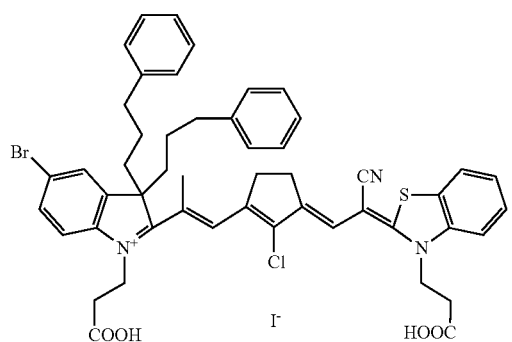
(127)
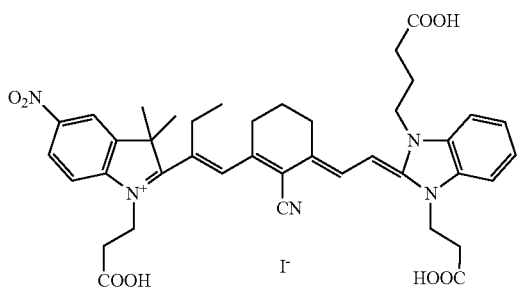
(128)
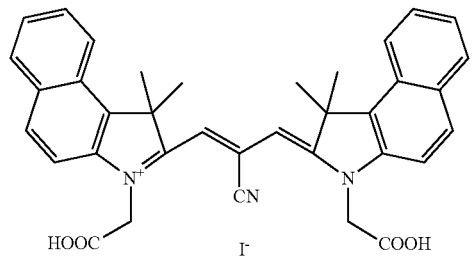
(129)
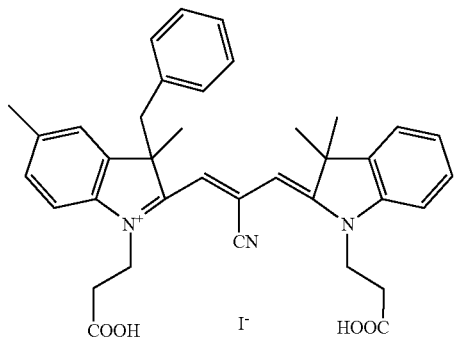
(130)
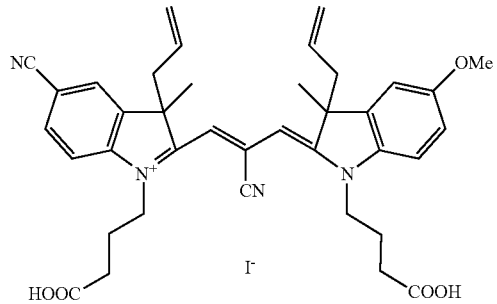
(131)
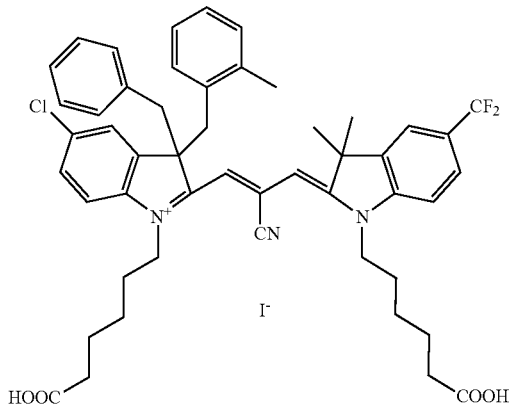

[Formula 36]
(132) 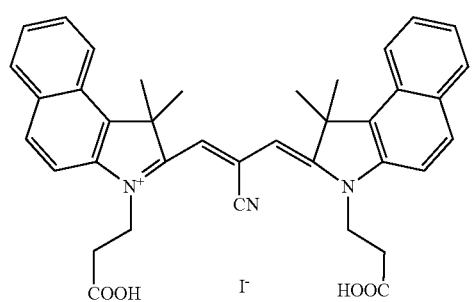
(133) 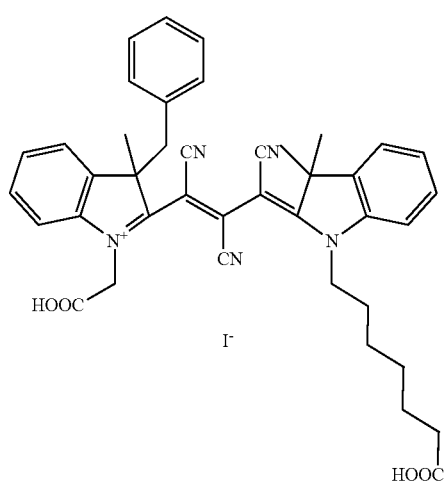
(134) 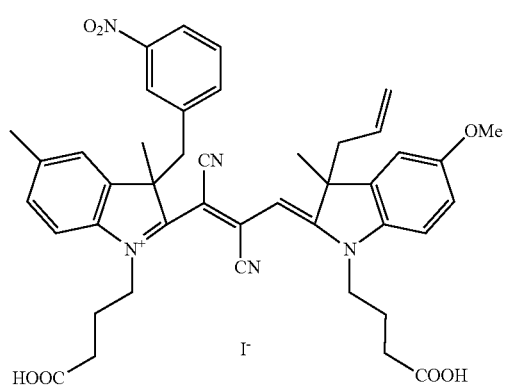
(135) 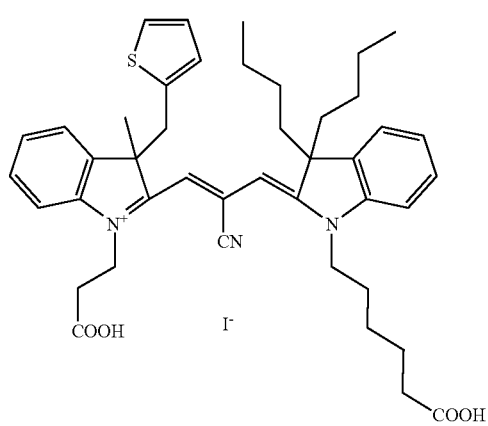
(136) 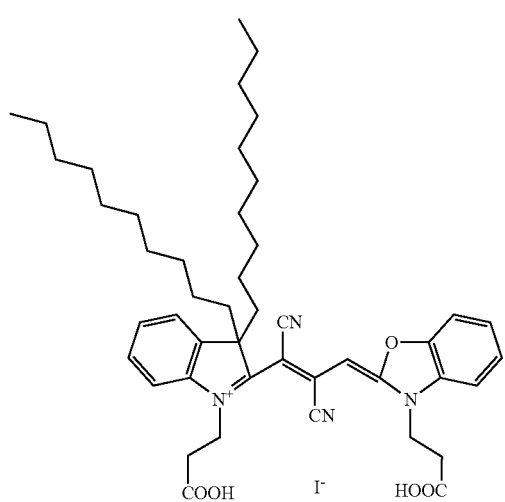
(137) 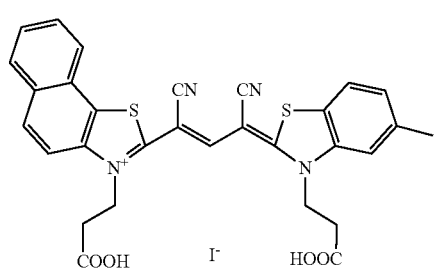

-continued
(138)
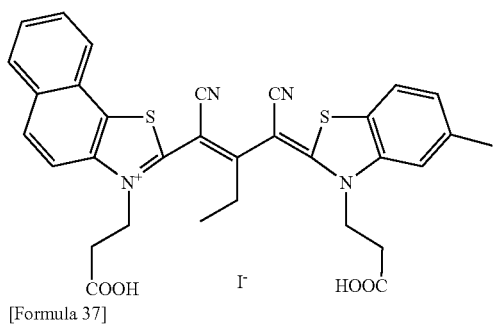
(139)
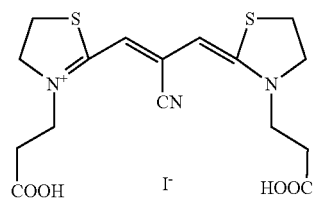
(140)
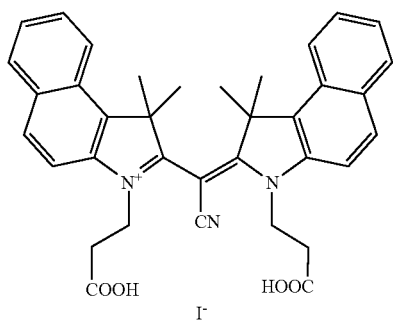
(141)
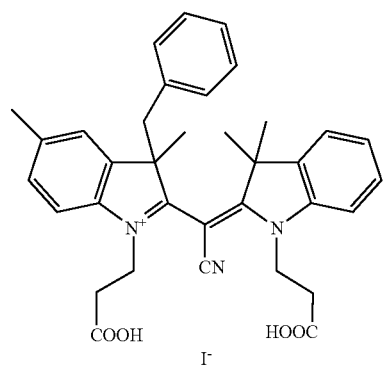
(142)
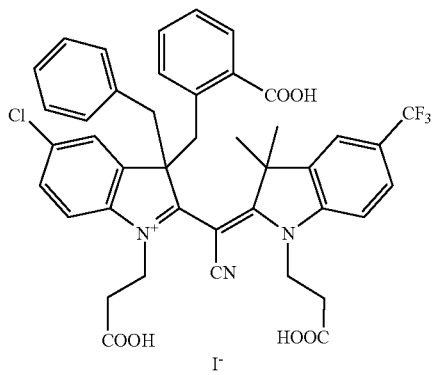
(143)
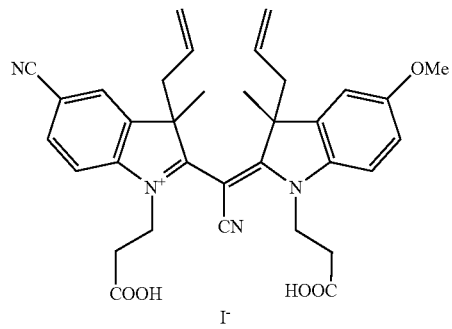
(144)
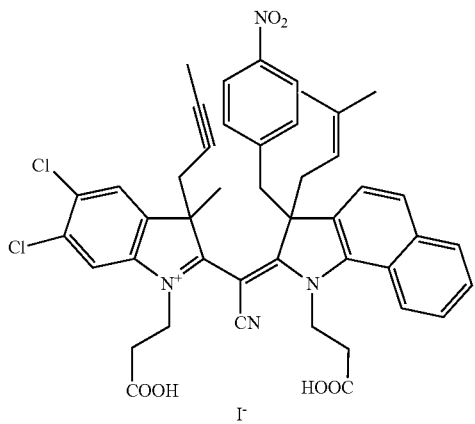
(145)
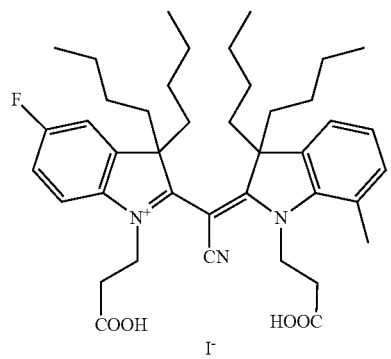
[Formula 37]

-continued
(146)
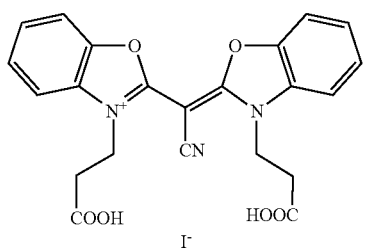
(147)
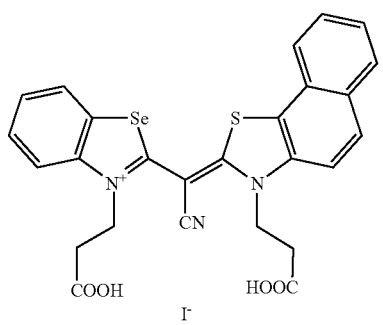
[Formula 38]
(148)
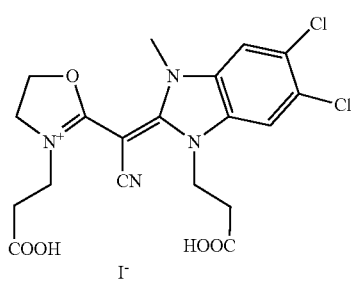
(149)
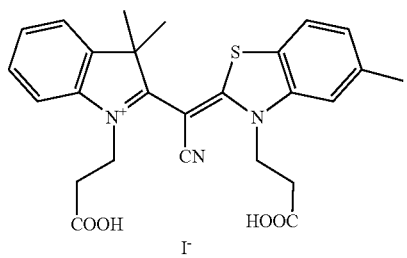
(150)
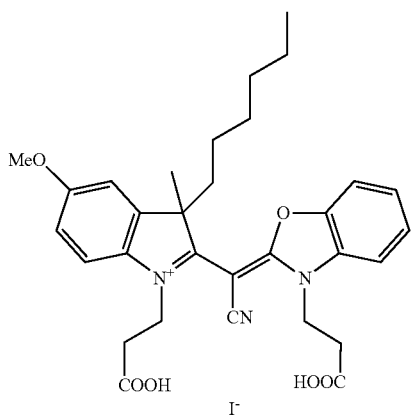
(151)
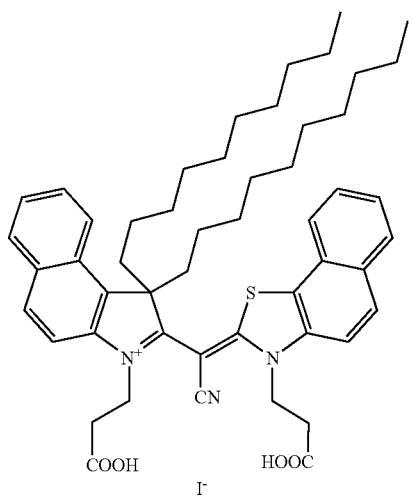
(152)
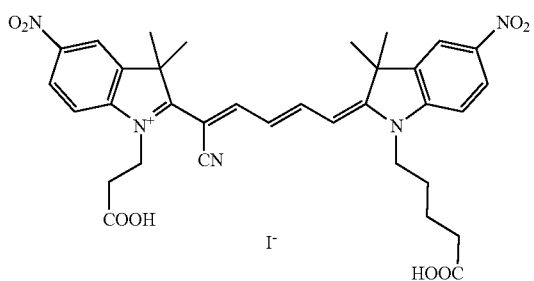
(153)
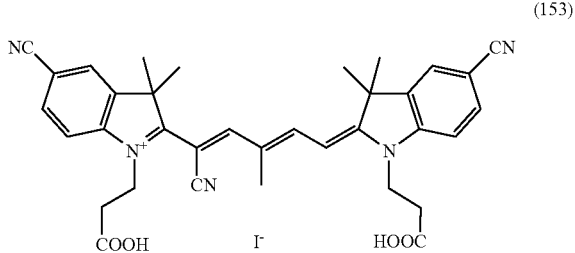

(154)
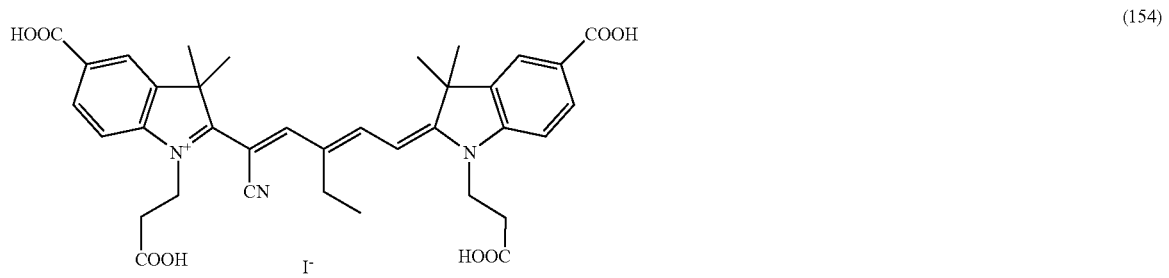
[Formula 39]
(155) (156)
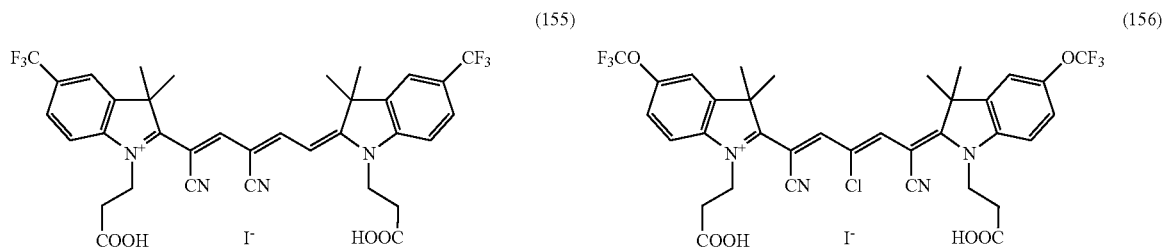
(157) (158)
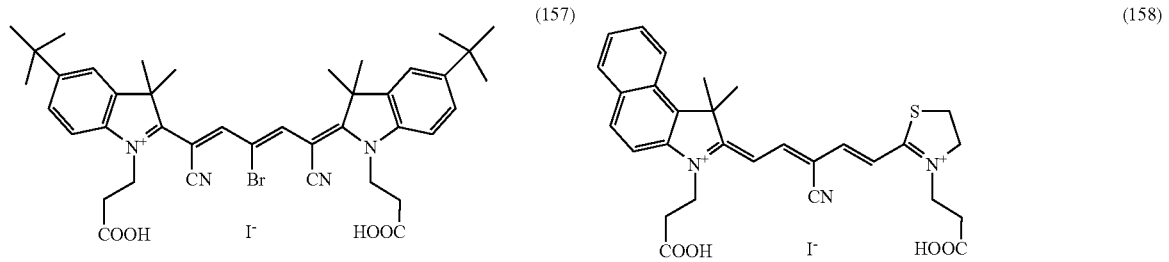
(159) (160)
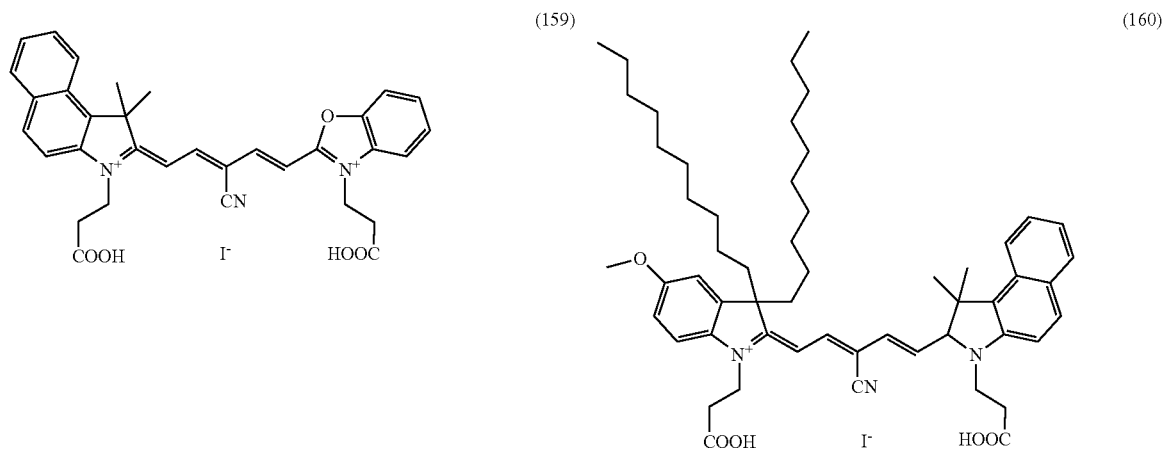

(161)

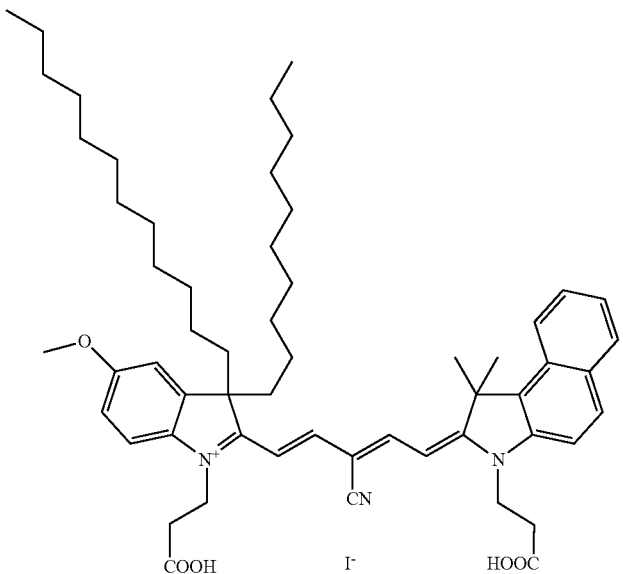

The cyanine compound shown in Chemical formula (1) is able to be synthesized, for example, as follows.

First, the anchor groups (Y1 and Y2) are introduced to the nitrogen atom of the heterocyclic skeleton in Chemical formula (1). Specifically, as expressed by Chemical reaction formula (I), the compound having a heterocyclic skeleton expressed by Chemical formula (162) and the compound expressed by Chemical formula (163) are mixed and reacted. Thereby, the quaternary ammonium salt expressed by Chemical formula (164) is synthesized. The compound having a heterocyclic skeleton expressed by Chemical formula (162) includes a skeleton section that is to be subsequently bonded with both ends of the methine chain skeleton (Q) in Chemical formula (1). Further, the compound shown in Chemical formula (163) is a section that is to be introduced to the nitrogen atom included in the heterocyclic skeleton in Chemical formula (162) so that R24 is detached and that is to be the anchor group (Y1). In Chemical reaction formula (I), one of the heterocyclic skeletons bonded with both ends of the methine chain skeleton is shown. However, the other heterocyclic skeleton section is able to be similarly synthesized.

[Formula 40]

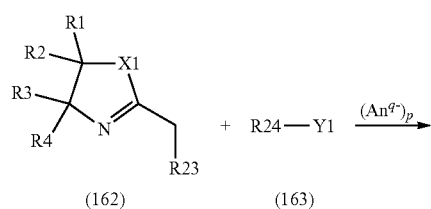

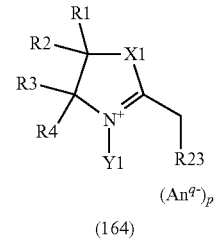

(R1 to R4 and X1 are similar to R1 to R4 and X1 explained in Chemical formula (1). R23 is a hydrogen atom, a cyano group, or a substituent group other than the cyano group, and a monovalent group to be introduced to the carbon atom of Q in Chemical formula (1). R24 is a detachment group of a halogen atom or the like. Y1 is an anchor group. $An^{q-}$ is an anion with q valency. q is 1 or 2, and p is a coefficient to maintain neutral electric charge in the compound of Chemical formula (164).)

Next, in the case where the carbon atomicity structuring the methine chain skeleton of Q in Chemical formula (1) is 1, as expressed by Chemical reaction formula (II), the quaternary ammonium salt expressed by Chemical formula (164-1) as the quaternary ammonium salt shown in Chemical formula (164) and the quaternary ammonium salt expressed by Chemical formula (165) having a detachment group are reacted under the presence of a base to obtain a cyanine compound (Chemical formula (166)) with carbon atomicity of 1 structuring the methine chain skeleton of Q in Chemical formula (1) of 1 as a final product. The quaternary ammonium salt shown in Chemical formula (165) used in this case is a compound having —S—R25 as a detachment group.

[Formula 41]

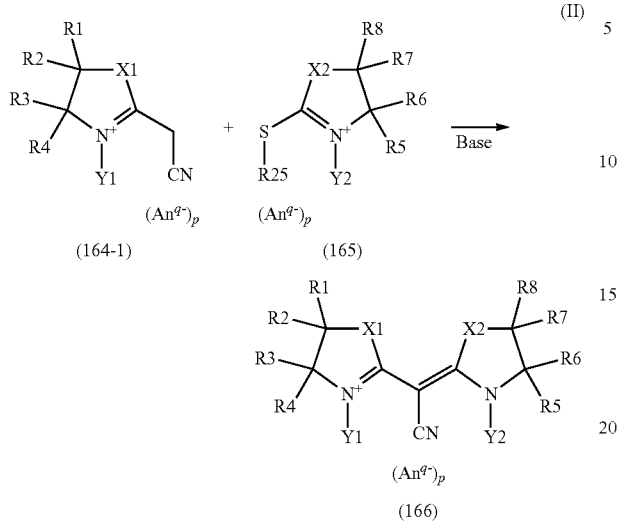

(R1 to R8 Y1, Y2, X1, and X2 are similar to R1 to R8 Y1, Y2, X1, and X2 explained in Chemical formula (1). $An^{q-}$ is an anion with q valency. q is 1 or 2, and p is a coefficient to maintain neutral electric charge in the compounds shown in Chemical formula (164-1), Chemical formula (165), and Chemical formula (166). R25 is an alkyl group such as a methyl group.)

Further, in the case where the carbon atomicity structuring the methine chain skeleton of Q in Chemical formula (1) is larger than 1, for example, reaction is made as expressed by Chemical reaction formula (III). Specifically, the quaternary ammonium salt shown in Chemical formula (164) synthesized by Chemical reaction formula (I) and Chemical formula (168) and the compound expressed by Chemical formula (167) as a bridge agent are reacted under the presence of a base and acetic anhydride ($(CH_3CO)_2O$) to obtain a cyanine compound (Chemical formula (169)) with carbon atomicity structuring the methine chain skeleton of Q in Chemical formula (1) of the number larger than 1 as a final product. Examples of the compound expressed in Chemical formula (167) used as the bridge agent in this case include the compounds expressed by Chemical formula (167-1) to Chemical formula (167-4). Examples of other bridge agents include the compounds expressed by Chemical formula (170) to Chemical formula (172).

[Formula 42]

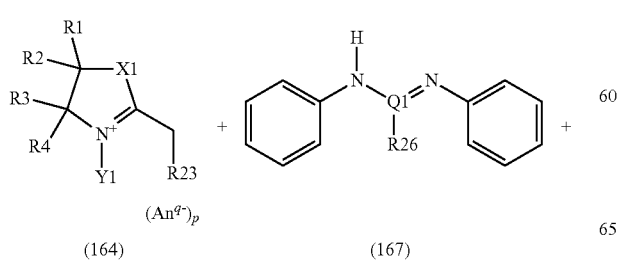

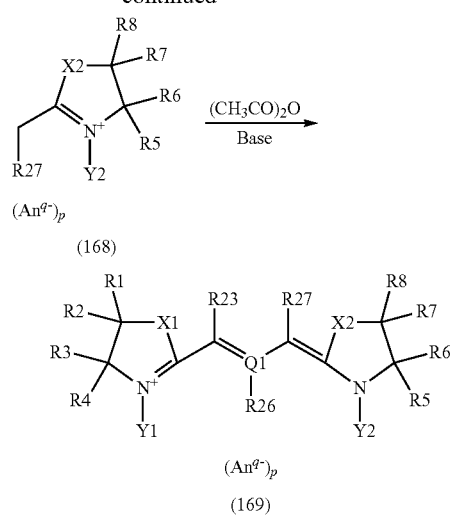

(R1 to R8, Y1, Y2, X1, and X2 are similar to R1 to R8, Y1, Y2, X1, and X2 explained in Chemical formula (1). R23, R26, and R27 are a hydrogen atom, a cyano group, or a substituent group other than the cyano group. Q1 is a linkage group that has a methine chain with carbon atomicity from 1 to 5 both inclusive as a skeleton. At least one of R23, R26, and R27 is a cyano group. $An^{q-}$ is an anion with q valency. q is 1 or 2, and p is a coefficient to maintain neutral electric charge in the compounds shown in Chemical formula (164), Chemical formula (168), and Chemical formula (169).)

[Formula 43]

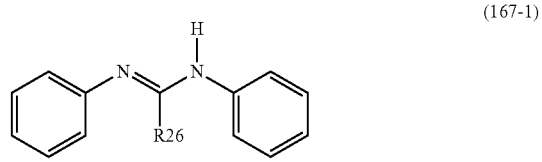

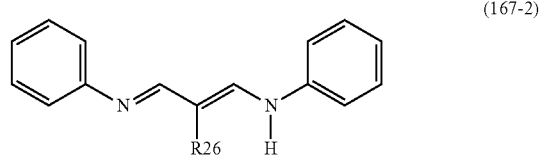

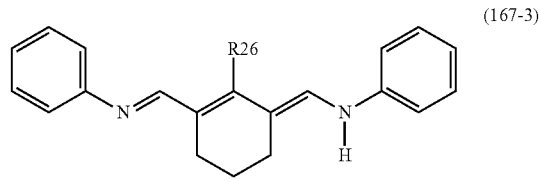

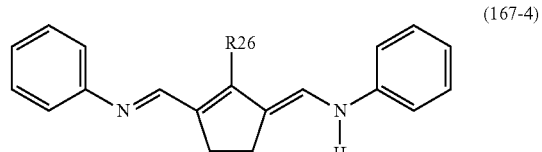

(R26 is a hydrogen atom, a cyano group, or a substituent group other than the cyano group.)

[Formula 44]

(170)

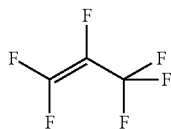

(171)

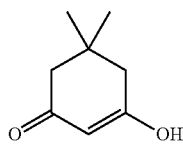

(172)

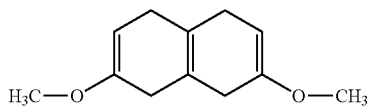

As described above, the cyanine compound shown in Chemical formula (1) is synthesized.

According to the dye of this embodiment, the cyanine structure shown in Chemical formula (1) has the anchor groups introduced to the nitrogen atom in the heterocyclic skeleton bonded with both ends of the methine chain skeleton and the cyano group introduced to the carbon atom structuring the methine chain skeleton. Thus, for example, in the case where the dye is supported by the base substance containing a metal oxide semiconductor material or the like, if light is absorbed and excitation is generated, electrons are efficiently and immediately injected into the support body. Further, if the dye is contacted with an organic solvent contained in an electrolyte or the like or moisture in a state that the dye is supported by the base substance, the dye is not easily exfoliated. Thereby, the cyanine compound shown in Chemical formula (1) is able to improve electron injection efficiency and fixation characteristics to the base substance. Thus, in the case where the dye is used for a photoelectric conversion device, electron injection amount to the support body in relation to light absorption amount is increased as the entire dye, and exfoliation from the support body is inhibited, and thus the dye is able to contribute to improving conversion efficiency.

Further, the cyanine compound shown in Chemical formula (1) may be the compound expressed by Chemical formula (3). In this case, at least one of R9 and R10 shown in Chemical formula (3) is preferably the alkyl group with carbon atomicity from 6 to 25 both inclusive. Thereby, even if the cyanine structure including the indolenine skeleton that generally easily forms an association body is included, since the sterically bulky alkyl group with carbon atomicity from 6 to 25 both inclusive is introduced as at least one of R9 and R10, the steric size of the entire molecule becomes large. Thus, the ratio of the association amount that hardly contributes to electron injection efficiency to the base substance is decreased, and therefore electron injection efficiency to the base substance is able to be more improved.

Further, the cyanine compound shown in Chemical formula (1) may be the compound expressed by Chemical formula (4). In this case, if both the ring A and the ring B shown in Chemical formula (4) are a benzene ring having a methoxy group, since the methoxy group introduced to the ring A and the ring B is an electron releasing group, electron injection efficiency to the base substance is able to be more improved. Further, in this case, at least one of R9, R10, R12, and R13 shown in Chemical formula (4) is preferably an alkyl group with carbon atomicity from 6 to 25 both inclusive. Specially, all of R9, R10, R12, and R13 are preferably the alkyl group with carbon atomicity from 6 to 25 both inclusive. Thereby, as the entire molecule, the steric size of the structure becomes large, and the ratio of the association body that hardly contributes to electron injection is decreased on the surface of the base substance. Thus, electron injection efficiency is able to be more improved.

Further, Q shown in Chemical formula (1), Chemical formula (3), or Chemical formula (4) may be a linkage group in which a methine chain with carbon atomicity of 5 is a skeleton and a cyano group is introduced to a carbon atom as a center of the methine chain. The foregoing anchor group may be a group expressed by —$CH_2$—$CH_2$—$C(=O)$—OH or a group expressed by —$CH_2$—$CH_2$—$C(=O)$—$O^-$. Thereby, the foregoing effect is able to be sufficiently demonstrated.

Next, a description will be given of a usage example of the dye according to this embodiment. In the following description, a photoelectric conversion device including an electrode having the dye is taken as an example. The dye of this embodiment is used for the photoelectric conversion device as follows.

Figure 2:
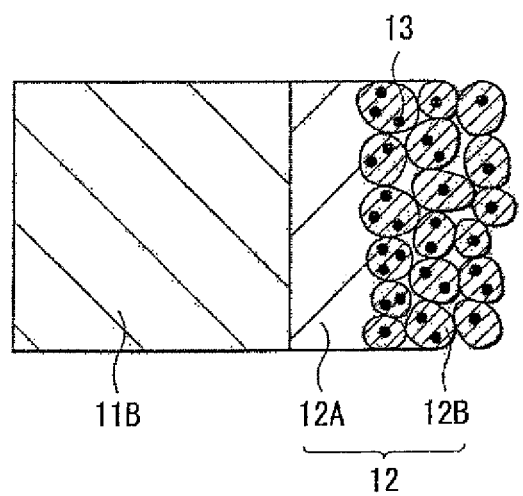
FIG. 2 is a cross sectional view illustrating an enlarged and extracted main section of the photoelectric conversion device illustrated in FIG. 1.

FIG. 1 schematically illustrates a cross sectional structure of the photoelectric conversion device. FIG. 2 illustrates an enlarged and extracted main section of the photoelectric conversion device illustrated in FIG. 1. The photoelectric conversion device illustrated in FIG. 1 and FIG. 2 is a main section of the so-called dye-sensitized solar cell. In the photoelectric conversion device, a work electrode 10 and an opposed electrode 20 are oppositely arranged with an electrolyte-containing layer 30 in between. At least one of the work electrode 10 and the opposed electrode 20 is an electrode having optical transparency.

The work electrode 10 has, for example, a conductive substrate 11, a metal oxide semiconductor layer 12 provided on one face thereof (face on the opposed electrode 20 side), and a dye 13 supported by the metal oxide semiconductor layer 12 as a support body. The work electrode 10 functions as an anode for an external circuit. For example, in the conductive substrate 11, a conductive layer 11B is provided on the surface of an insulative substrate 11A.

Examples of a material of the substrate 11A include an insulative material such as glass, plastic, and a transparent polymer film. Examples of the transparent polymer film include tetraacetyl cellulose (TAC), polyethylene terephthalate (PET), polyethylene naphthalate (PEN), syndiotactic polystyrene (SPS), polyphenylene sulfide (PPS), polycarbonate (PC), polyarylate (PAr), polysulfone (PSF), polyestersulfone (PES), polyetherimide (PEI), cyclic polyolefin, and brominated phenoxy.

Examples of the conductive layer 11B include a conductive metal oxide thin film such as indium oxide, tin oxide, indium-tin composite oxide (ITO), and a compound obtained by doping tin oxide with fluorine (FTO: F—$SnO_2$); a metal thin film such as gold (Au), silver (Ag), and platinum (Pt); and a compound composed of a conductive polymer or the like.

The conductive substrate 11 may be formed, for example, as a single layer structure made of a conducive material. In this case, examples of a material of the conductive substrate 11 include a conductive metal oxide such as indium oxide, tin oxide, indium-tin composite oxide, and a compound obtained by doping tin oxide with fluorine; a metal such as gold, silver, and platinum; and a conductive polymer.

The metal oxide semiconductor layer 12 is a support body to support the dye 13, and has, for example, a porous structure as illustrated in FIG. 2. The metal oxide semiconductor layer 12 is formed from a dense layer 12A and a porous layer 12B. In the interface with the conductive substrate 11, the dense layer 12A is formed. The dense layer 12A is preferably dense and preferably has a small number of air gaps, and is more preferably in a state of a film. In the surface contacted with the electrolyte-containing layer 30, the porous layer 12B is formed. The porous layer 12B preferably has a structure in which the number of air gaps is large and the surface area is large. In particular, the porous layer 12B preferably has a structure in which porous minute particles are adhered thereto. The metal oxide semiconductor layer 12 may be formed, for example, as a film-like single layer structure.

Examples of a material of the metal oxide semiconductor layer 12 (metal oxide semiconductor material) include titanium oxide, zinc oxide, tin oxide, niobium oxide, indium oxide, zirconium oxide, tantalum oxide, vanadium oxide, yttrium oxide, aluminum oxide, and magnesium oxide. Specially, as the metal oxide semiconductor material, at least one of titanium oxide and zinc oxide is preferable, and zinc oxide is more preferable, since thereby high conversion efficiency is able to be obtained. One of the foregoing metal oxide semiconductor materials may be used singly, or two or more thereof may be used as a composite (mixture, mixed crystal, solid dispersion or the like). For example, a combination of zinc oxide and tin oxide, a combination of titanium oxide and niobium oxide or the like may be used.

Examples of a method of forming the metal oxide semiconductor layer 12 having the porous structure include electrolytic precipitation method and sintering method. In the case where the metal oxide semiconductor layer 12 is formed by electrolytic precipitation method, in an electrolytic bath liquid containing minute particles of the metal oxide semiconductor material, the minute particles are adhered onto the conductive layer 11B of the conductive substrate 11, and the metal oxide semiconductor material is precipitated. Further, in the case where the metal oxide semiconductor layer 12 is formed by sintering method, the conductive substrate 11 is coated with a dispersion liquid (metal oxide slurry) in which the minute particles of the metal oxide semiconductor material are dispersed, and the resultant is subsequently fired. As a method of forming the metal oxide semiconductor layer 12, electrolytic precipitation method is preferable. With electrolytic precipitation method, high conversion efficiency is able to be obtained, and a plastic material or a polymer film material with low heat resistance is able to be used as the substrate 11A, and thus a highly flexible photoelectric conversion device is able to be fabricated.

The dye 13 is, for example, absorbed to the metal oxide semiconductor layer 12 as a base substance. The dye 13 includes one or more dyes capable of injecting electrons into the metal oxide semiconductor layer 12 by absorbing light and being excited. The dye 13 contains one or more compounds out of the cyanine compound shown in the foregoing Chemical formula (1) as the dye. Since the cyanine compound shown in Chemical formula (1) is contained, as the entire dye, the ratio of electron injection amount to the metal oxide semiconductor layer 12 in relation to light absorption amount is increased and exfoliation from the metal oxide semiconductor layer 12 is inhibited, and accordingly conversion efficiency is improved.

Further, the dye 13 may contain other dye in addition to the cyanine compound shown in the Chemical formula (1). As other dye, a dye having an electron withdrawing substituent group capable of being chemically bonded with the metal oxide semiconductor layer 12 is preferable. Examples of other dye include an organic dye such as eosin Y, dibromofluorescein, fluorescein, rhodamine B, pyrogallol, dichlorofluorescein, Erhthrosine B (Erhthrosine: registered trademark), fluorescin, mercurochrome, a cyanine dye, a merocyanine disazo dye, a trisazo dye, an anthraquinone dye, a polycyclic quinone dye, an indigo dye, a diphenylmethane dye, a trimethylmethane dye, a quinoline dye, a benzophenone dye, a naphthoquinone dye, a perylene dye, a fluorenone dye, a squarylium dye, an azulenium dye, a perinone dye, a quinacridone dye, a metal-free phthalocyanine dye, and a metal-free porphyrin dye or the like.

Further, examples of other dye include an organic metal complex compound. Examples thereof include an organic metal complex compound having both ionic coordinate bond formed from a nitrogen anion in an aromatic heterocycle and a metal cation and nonionic coordinate bond formed between a nitrogen atom/a chalcogen atom and a metal cation; and an organic metal complex compound having both ionic coordinate bond formed from an oxygen anion/a sulfur anion and a metal cation and nonionic coordinate bond formed between a nitrogen atom/a chalcogen atom and a metal cation. Specific examples thereof include a metal phthalocyanine dye such as copper phthalocyanine and titanyl phthalocyanine; a metal naphthalocyanine die; a metal porphyrin dye; and a ruthenium complex such as a bipyridyl ruthenium complex, a terpyridyl ruthenium complex, a phenanthrolyl ruthenium complex, a bicinchoninic acid ruthenium complex, an azo ruthenium complex, and a quinolinol ruthenium complex.

Further, the dye 13 may contain an additive in addition to the foregoing dye. Examples of the additive include an association inhibitor for inhibiting association of the dye in the dye 13. Specific examples thereof include the cholate compound expressed by Chemical formula (173). Such an additive may be used singly, or a plurality thereof may be used by mixture.

[Formula 45]

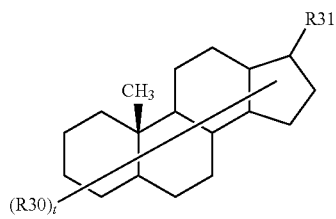

(173)

(R30 represents a group bonded with one of carbon atoms structuring the steroid skeleton in the formula, and is a hydrogen group, a halogen group, an alkyl group, an alkoxy group, an aryl group, a hetero ring group, an acyl group, an acyloxy group, an oxycarbonyl group, an oxo group, an acid group, or a derivative thereof, which may be identical or different from each other. R31 is an alkyl group having an acid group. t is an integer number out of 1 to 5. Bond between each carbon atom structuring the steroid skeleton in the formula is single bond or double bond.)

In the opposed electrode 20, for example, a conductive layer 22 is provided on a conducive substrate 21. The opposed electrode 20 functions as a cathode for an external circuit. Examples of a material of the conducive substrate 21 include a material similar to that of the conductive substrate 11 of the work electrode 10. Examples of a conductive material used for the conductive layer 22 include a metal such as platinum, gold, silver, copper (Cu), rhodium (Rh), ruthenium (Ru), aluminum (Al), magnesium (Mg), and indium (In); carbon (C); and a conductive polymer. Such a conductive material may be used singly, or a plurality thereof may be used by mixture. Further, according to needs, as a binding agent, for example, an acryl resin, a polyester resin, a phenol resin, an epoxy resin, a cellulose, a melamine resin, fluoroelastomer, a polyimide resin or the like may be used. The opposed electrode 20 may have, for example, a single layer structure of the conductive layer 22.

The electrolyte-containing layer 30 contains, for example, a redox electrolyte. Examples of the redox electrolyte include an $I^-/I_3^-$ electrolyte, a $Br^-/Br_3^-$ electrolyte, and a quinone/hydroquinone electrolyte. Specific examples thereof include a combination of a halide salt and a halogen simple body such as a combination of an iodide salt and an iodine simple body and a combination of quaternary alkyl ammonium bromide and bromine. Examples of the halide salt include cesium halide, halide quaternary alkyl ammonium, imidazolium halide, thiazolium halide, oxazolium halide, quinolinium halide, and pyridinium halide. Specific examples thereof include cesium iodide as iodide salt; tetraethyl ammonium iodide, tetrapropyl ammonium iodide, tetrabutyl ammonium iodide, tetrapentyl ammonium iodide, tetrahexyl ammonium iodide, tetraheptyl ammonium iodide, and trimethyl phenyl ammonium iodide as quaternary alkyl ammonium iodide; 3-methylimidazolium iodide and 1-propyl-2,3-dimethylimidazolium iodide as imidazolium iodide; 3-ethyl-2-methyl-2-thiazolium iodide, 3-ethyl-5-(2-hydroxyethyl)-4-methylthiazolium iodide, and 3-ethyl-2-methylbenzothiazolium iodide as thiazolium iodide; 3-ethyl-2-methylbenzooxazolium iodide as oxazolium iodide; 1-ethyl-2-methylquinolinium iodide as quinolinium iodide; and pyridinium iodide. Of the combinations of a halide salt and a halogen simple body, a combination of at least one of the foregoing iodide salts and iodine simple body is preferable.

Further, as the redox electrolyte, for example, a combination of an ionic liquid and a halogen simple body may be used. In this case, the foregoing halide salt or the like may be contained. Examples of the ionic liquid include a substance usable for a battery, a solar cell or the like. Examples thereof include substances disclosed in "Inorg. Chem.," 1996, 35, pp. 1168-1178; "Electrochemistry," 2002, 2, pp. 130-136; Japanese Unexamined Patent Application Publication No. 9-507334; Japanese Unexamined Patent Application Publication No. 8-259543 and the like. Specially, as the ionic liquid, a salt having a lower melting point than room temperature (25 deg C), or a salt that has a higher melting point than room temperature but goes into a liquid state at room temperature by being dissolved with other molten salt is preferable. Specific examples of the ionic liquid include an anion, a cation or the like described below.

Examples of ionic liquid cation include ammonium, imidazolium, oxazolium, thiazolium, oxadiazolium, triazolium, pyrrolidinium, pyridinium, piperidinium, pyrazolium, pyrimidinium, pyrazinium, triazinium, phosphonium, sulfonium, carbazolium, indolium, and a derivative thereof. Such an ionic liquid cation may be used singly, or a plurality thereof may be used by mixture. Specific examples thereof include 1-methyl-3-propylirnidazolium, 1-butyl-3-methylimidazolium, 1,2-dimethyl-3-propylimidazolium, and 1-ethyl-3-methylimidazolium.

Examples of ionic liquid anion include a metal chloride such as $AlCl_4^-$ and $Al_2Cl_7^-$; a fluorine-containing ion such as $PF_6^-$, $BF_4^-$, $CF_3SO_3^-$, $N(CF_3SO_2)_2^-$, $F(HF)_n^-$, and $CF_3COO^-$; a non-fluorine compound ion such as $NO_3^-$, $CH_3COO^-$, $C_6H_{11}COO^-$, $CH_3OSO_3^-$, $CH_3OSO_2^-$, $CH_3SO_3^-$, $CH_3SO_2^-$, $(CH_3O)_2PO_2^-$, $N(CN)_2^-$, and $SCN^-$; and a halide ion such as iodine and bromine. Such an ionic liquid anion may be used singly, or a plurality thereof may be used by mixture. Specially, as the ionic liquid anion, an iodide ion is preferable.

For the electrolyte-containing layer 30, as the foregoing redox electrolyte, a liquid electrolyte (electrolytic solution) may be used, or a solid polymer in which an electrolytic solution is held in a polymer material may be used. Further, a solidified (paste-like) electrolyte obtained by mixing an electrolytic solution and a particulate carbon material such as carbon black may be used. In the solidified electrolyte containing a carbon material, the carbon material has a function to catalyze redox reaction, and thus a halogen simple body is not necessarily contained in the electrolyte. Such a redox electrolyte may contain one or more organic solvents that dissolve the foregoing halide salt, the ionic liquid and the like. Examples of the organic solvent include an electrochemically inactive organic solvent. Examples thereof include acetonitrile, propionitrile, butyronitrile, methoxyacetonitrile, 3-methoxypropionitrile, veleronitrile, dimethylcarbonate, ethylmethylcarbonate, ethylenecarbonate, propylenecarbonate, N-methylpyrrolidone, pentanol, quinoline, N,N-dimethylformamide, γ-butyrolactone, dimethylsulfoxide, and 1,4-dioxane.

In the photoelectronic conversion device, in the case where light (sun light, or ultraviolet light or visible light equal to sun light) illuminates the dye 13 supported by the work electrode 10, the dye 13 that absorbs the light and is excited injects electrons into the metal oxide semiconductor layer 12. The electrons are moved to the conductive layer 11B, pass through an external circuit, and reach the opposed electrode 20. Meanwhile, in the electrolyte-containing layer 30, the electrolyte is oxidized so that the dye 13 oxidized associated with movement of the electrons is returned to the ground state (reduced). The oxidized electrolyte receives the foregoing electrons, and thereby reduction is made. As described above, movement of the electrons between the work electrode 10 and the opposed electrode 20 and redox reaction in the electrolyte-containing layer 30 associated therewith are repeated. Thereby, continuous movement of electrons is generated, and continual photoelectric conversion is made.

The photoelectric conversion device is able to be manufactured, for example, as follows.

First, the work electrode 10 is formed. First, the metal oxide semiconductor layer 12 having the porous structure is formed on the face where the conductive layer 11B is formed out of the conducive substrate 11 by electrolytic precipitation method or sintering method. In the case where the metal oxide semiconductor layer 12 is formed by electrolytic precipitation method, for example, temperature of an electrolytic bath liquid containing a metal salt to become the metal oxide semiconductor material is set to given temperature while bubbling with oxygen and air is made, the conductive substrate 11 is soaked in the electrolytic bath liquid, and a constant voltage is applied between the conductive substrate 11 and the opposed electrode. Thereby, the metal oxide semiconductor material is precipitated to have the porous structure on the conductive layer 11B. At this time, the opposed electrode may be moved as appropriate in the electrolytic bath liquid. Further, in the case where the metal oxide semiconductor layer 12 is formed by sintering method, the conductive substrate 11 is coated with a metal oxide slurry prepared by dispersing powder of the metal oxide semiconductor material in a dispersion medium, and the resultant is subsequently dried and fired to have a porous structure. Subsequently, a dye solution in which the dye 13 containing the cyanine compound shown in the foregoing Chemical formula (1) is dissolved in an organic solvent is prepared. The conductive substrate 11 on which the metal oxide semiconductor layer 12 is formed is soaked into the dye solution, and thereby the dye 13 is supported by the metal oxide semiconductor layer 12.

Next, the conductive layer 22 is formed on a single face of the conductive substrate 21, and thereby the opposed electrode 20 is formed. The conductive layer 22 is formed by sputtering the conductive material.

Finally, the face where the dye 13 is supported out of the work electrode 10 and the face where the conductive layer 22 is formed out of the opposed electrode 20 are bonded with a spacer (not illustrated) such as a sealing agent in between so that the foregoing faces are spaced with a given distance in between and are opposed to each other, and the entire body is sealed except for, for example, an injection inlet of the electrolyte. Subsequently, after the electrolyte is injected between the work electrode 10 and the opposed electrode 20, the injection inlet is sealed, and thereby the electrolyte-containing layer 30 is formed. Thereby, the photoelectric conversion device illustrated in FIG. 1 and FIG. 2 is completed.

In the photoelectric conversion device, since the dye 13 contains the cyanine compound shown in Chemical formula (1), electron injection efficiency from the dye 13 to the metal oxide semiconductor layer 12 is improved, and exfoliation from the metal oxide semiconductor layer 12 hardly occurs. Specifically, the cyanine compound shown in Chemical formula (1) has the anchor groups (Y1 and Y2) introduced to the heterocyclic skeleton boded with both ends of the methine chain skeleton and the cyano group introduced to the methine chain skeleton. Thereby, in the cyanine compound shown in Chemical formula (1), if the dye absorbs light and is excited, electrons are efficiently injected into the metal oxide semiconductor layer 12. In addition, if the dye is contacted with the organic solvent contained in the electrolyte-containing layer 30 or water intruding in the device, the dye is not easily exfoliated from the metal oxide semiconductor layer 12. Thus, according to the photoelectric conversion device, compared to a case that the dye 13 contains, for example, a compound not including the structure shown in Chemical formula (1) (for example, the cyanine compound in which the cyano group is not introduced to the methine chain skeleton), electron injection amount to the metal oxide semiconductor layer 12 in relation to light absorption amount is increased as the entire dye contained in the dye 13, and exfoliation amount of the dye from the metal oxide semiconductor layer 12 is decreased, and thus conversion efficiency is able to be improved.

In this case, the cyanine compound shown in Chemical formula (1) may be the compound expressed by Chemical formula (3). In the case where at least one of R9 and R10 shown in Chemical formula (3) is the alkyl group with carbon atomicity from 6 to 25 both inclusive, even if the cyanine structure including the indolenine skeleton that generally easily forms an association body is included, since the sterically bulky alkyl group with carbon atomicity from 6 to 25 both inclusive is introduced as at least one of R9 and R10, the steric size of the entire molecule becomes large. Thus, the ratio of the association body that hardly contributes to photoelectric conversion in the dye 13 is decreased on the surface of the metal oxide semiconductor layer 12, and thus conversion efficiency is able to be more improved.

Further, the cyanine compound shown in Chemical formula (1) may be the compound expressed by Chemical formula (4). In this case, if both the ring A and the ring B shown in Chemical formula (4) are a benzene ring having a methoxy group, since the methoxy group introduced to the ring A and the ring B is an electron releasing group, electron injection to the base substance becomes more effective, and higher conversion efficiency is able to be obtained. Further, in this case, at least one of R9, R10, R12, and R13 shown in Chemical formula (4) is preferably an alkyl group with carbon atomicity from 6 to 25 both inclusive. Specially, all of R9, R10, R12, and R13 are preferably the alkyl group with carbon atomicity from 6 to 25 both inclusive. Thereby, as the entire molecule, the steric size becomes large, and the ratio of the association body that hardly contributes to photoelectric conversion in the dye 13 is more decreased on the surface of the metal oxide semiconductor layer 12. Thus, high conversion efficiency is able to be obtained.

Further, Q shown in Chemical formula (1), Chemical formula (3), or Chemical formula (4) may be a linkage group in which a methine chain with carbon atomicity of 5 is a skeleton and a cyano group is introduced to a carbon atom as a center of the methine chain. The foregoing anchor group (Y1 and Y2) may be a group expressed by —$CH_2$—$CH_2$—$C(=O)$—OH or a group expressed by —$CH_2$—$CH_2$—$C(=O)$—$O^-$.

In particular, in the case where the metal oxide semiconductor layer 12 is formed by electrolytic precipitation method and contains zinc oxide (ZnO), higher conversion efficiency is able to be obtained.

Further, in this case, in the case where the cyanine compound shown in Chemical formula (1) is the compound shown in Chemical formula (4) and both the ring A and the ring B in chemical formula (4) are a benzene ring having a methoxy group, electron injection efficiency and fixation characteristics are more improved, and thus higher conversion efficiency is able to be obtained. In particular, in the case where at least one of R9, R10, R12, and R13 is an alkyl group with carbon atomicity from 6 to 25 both inclusive, and specially in the case where all of R9, R10, R12, and R13 are the alkyl group with carbon atomicity from 6 to 25 both inclusive, high fixation characteristics and higher electron injection efficiency are able to be obtained, and thus conversion efficiency is able to be more improved.

In particular, in the case where the support body is formed by electrolytic precipitation method and contains zinc oxide, higher conversion efficiency is able to be obtained.

In the foregoing photoelectric conversion device, the description has been given of the case that the redox electrolyte is contained as the electrolyte-containing layer 30. However, as the electrolyte-containing layer 30, a solid charge transfer layer made of a solid electrolyte may be provided instead of the redox electrolyte. In this case, the solid charge transfer layer has a material in which, for example, carrier transfer in the solid is related to electric conduction. As the material, an electron transport material, an electron hole transport material and the like are preferable.

As the electron hole transport material, aromatic amine, a triphenylene derivative and the like are preferable. Examples thereof include an organic conductive polymer such as an oligothiophene compound, polypyrrole, polyacetylene or a derivative thereof, poly(p-phenylene) or a derivative thereof, poly(p-phenylenevinylene) or a derivative thereof, polythenylene vinylene or a derivative thereof, polythiophene or a derivative thereof, polyaniline or a derivative thereof, and polytoluidine or a derivative thereof.

As the electron hole transport material, for example, a p-type inorganic compound semiconductor may be used. In the p-type inorganic compound semiconductor, the bandgap is preferably 2 eV or more, and is more preferably 2.5 eV or more. Further, since the ionization potential of the p-type inorganic compound semiconductor is able to reduce electron holes of a dye, the ionization potential of the p-type inorganic compound semiconductor should be smaller than ionization potential of the work electrode 10. A preferable range of the ionization potential of the p-type inorganic compound semiconductor varies according to the dye to be used, but in general, the ionization potential of the p-type inorganic compound semiconductor is preferably from 4.5 eV to 5.5 eV both inclusive, and more preferably from 4.7 eV to 5.3 eV both inclusive.

Examples of the p-type inorganic compound semiconductor include a compound semiconductor containing monovalent copper. Examples of the compound semiconductor containing monovalent copper include CuI, CuSCN, $CuInSe_2$, $Cu(In, Ga)Se_2$, $CuGaS_2$, $Cu_2O$, CuS, $CuGaS_2$, $CuInS_2$, and $CuAlSe_2$. In addition, other examples of the p-type inorganic compound semiconductor include GaP, NiO, CoO, FeO, $Bi_2O_3$, $MoO_2$, and $Cr_2O_3$.

Examples of a method of forming the solid charge transfer layer include a method of forming the solid charge transfer layer directly on the work electrode 10. After that, the opposed electrode 20 may be formed.

The electron hole transport material containing an organic conductive polymer is able to be introduced into the electrode by a method such as vacuum evaporation method, cast method, coating method, spin coating method, dipping method, electrolytic polymerization method, and photoelectrolytic polymerization method. An inorganic solid compound is also able to be introduced into the electrode by a method such as cast method, coating method, spin coating method, dipping method, and electrolytic plating method. It is preferable that part of the solid charge transfer layer formed as above (in particular, the solid charge transfer layer having the electron hole transport material) partly penetrates into a gap of the porous structure of the metal oxide semiconductor layer 12 and is directly contacted therewith.

In the photoelectric conversion device in which a solid charge transfer layer is provided instead of the electrolyte-containing layer 30, conversion efficiency is able to be improved as in the case of using the redox electrolyte. Other action and effect are similar to those of the foregoing photoelectric conversion device.

EXAMPLES

A description will be given in detail of specific examples of the present invention.

Example 1-1

As a specific example of the dye explained in the foregoing embodiment, according to the foregoing Chemical formula (I) and the foregoing Chemical reaction formula (III), the compound shown in Chemical formula (7) as the compound shown in Chemical formula (4) was synthesized.

First, as shown in Chemical reaction formula (I-1), the compound expressed by Chemical formula (162-1) as the compound shown in Chemical formula (162) and the compound expressed by Chemical formula (163-1) as the compound shown in Chemical formula (163) were mixed and reacted. Thereby, the indolenium salt expressed by Chemical formula (164-1) as the quaternary ammonium salt expressed by Chemical formula (164) was obtained.

[Formula 46]

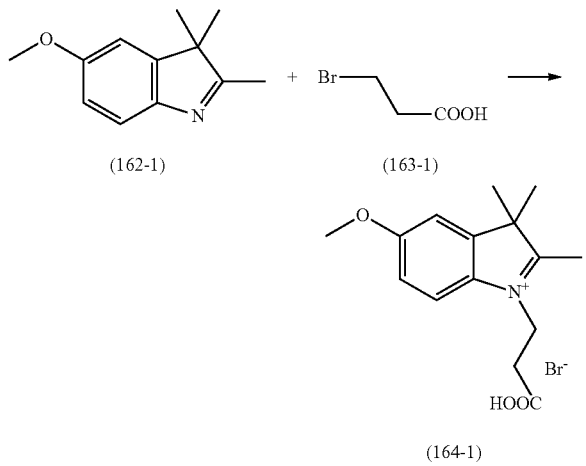

Next, as shown in Chemical reaction formula (III-1), the indolenium salt shown in Chemical formula (164-1) (10 mmol), amidine expressed by Chemical formula (167-5) as a bridge agent (5 mmol), acetic anhydride (20 mmol), triethylamine as a base (10 mmol), and acetonitrile ($CH_3CN$: 10 g) were mixed. The mixture was heated to reflux for 4 hours and was reacted. Subsequently, 10 g of chloroform and 10 g water were added to the reactant. After that, the precipitated solid was filtrated, the filtrate was dried under reduced pressure, and thereby a final product was obtained at yield of 23%.

[Formula 47]

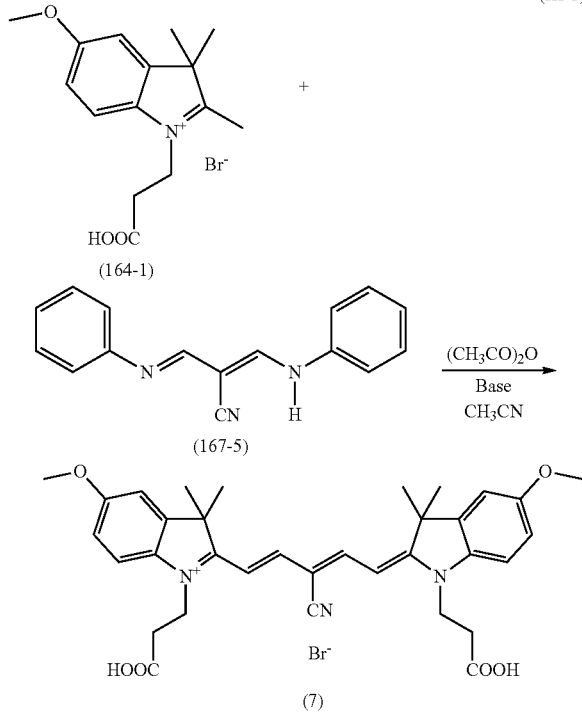

Example 1-2

The compound shown in Chemical formula (8) was synthesized. First, as shown in Chemical reaction formula (I-2), the indolenium salt expressed by Chemical formula (164-2) was obtained in the same manner as that of Example 1-1, except that the compound expressed by Chemical formula (162-2) was used instead of the compound shown in Chemical formula (162-1). Next, a final product was obtained in the same manner as that of Example 1-1, except that the indolenium salt shown in Chemical formula (164-2) was used instead of the indolenium salt shown in Chemical formula (164-1). In this case, the yield was 50%.

[Formula 48]

(I-2)

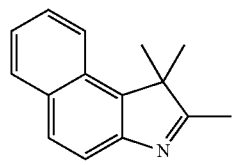

(162-2)    (163-1)

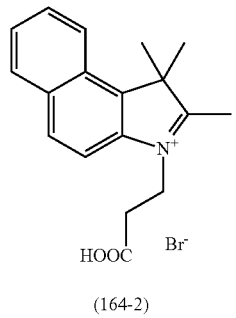

(164-2)

Example 1-3

The compound shown in Chemical formula (9) was synthesized. First, as shown in Chemical reaction formula (I-3), the indolenium salt expressed by Chemical formula (164-3) was obtained in the same manner as that of Example 1-1, except that the compound expressed by Chemical formula (162-3) was used instead of the compound shown in Chemical formula (162-1), and the compound expressed by Chemical formula (163-2) was used instead of the compound shown in Chemical formula (163-1). Next, a final product was obtained in the same manner as that of Example 1-1, except that the indolenium salt shown in Chemical formula (164-3) was used instead of the indolenium salt shown in Chemical formula (164-1). In this case, the yield was 2.3%.

[Formula 49]

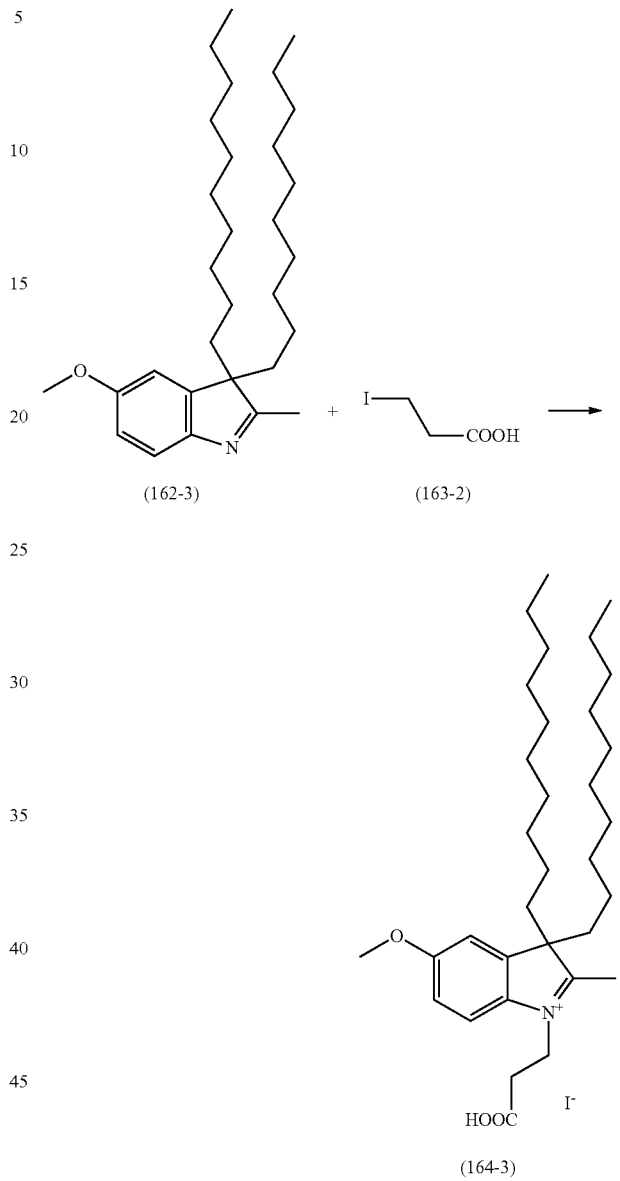

Example 1-4

The compound shown in Chemical formula (35) was synthesized. First, as shown in Chemical reaction formula (I-4), the salt (quaternary ammonium salt) expressed by Chemical formula (162-4) was obtained in the same manner as that of Example 1-3, except that the compound expressed by Chemical formula (164-4) was used instead of the compound shown in Chemical formula (162-3). Next, a final product was obtained in the same manner as that of Example 1-3, except that the compound shown in Chemical formula (164-4) was used instead of the indolenium salt shown in Chemical formula (164-3). In this case, the yield was 6.3%.

Example 1-6

The compound shown in Chemical formula (158) was synthesized. First, as shown in Chemical reaction formula (I-6), the salt expressed by Chemical formula (164-6) was obtained in the same manner as that of Example 1-1, except that the compound expressed by Chemical formula (162-6) was used instead of the compound shown in Chemical formula (162-1).

[Formula 50]

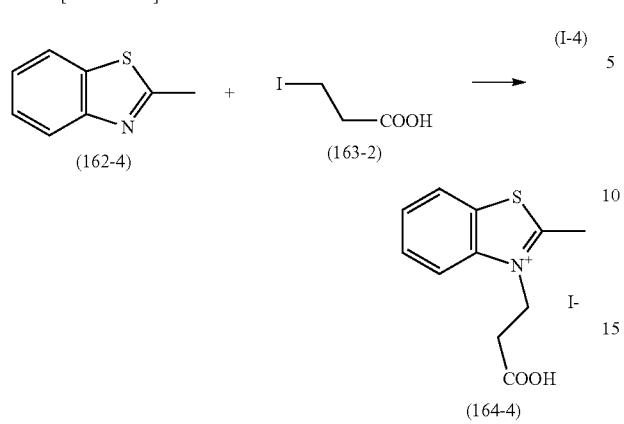

[Formula 52]

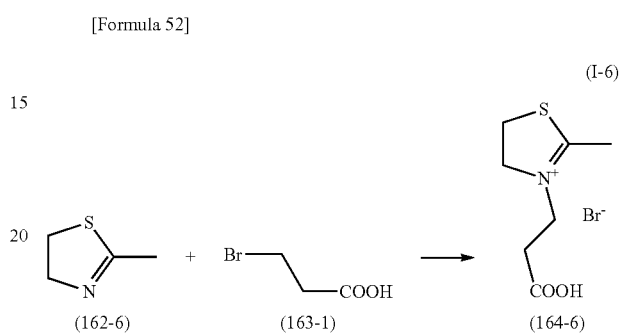

Example 1-5

The compound shown in Chemical formula (47) was synthesized. First, as shown in Chemical reaction formula (I-5), the indolenine compound expressed by Chemical formula (164-5A), the compound expressed by Chemical formula (164-5B), acetic acid, and water were mixed, and thereby the indolenium salt expressed by Chemical formula (164-5C) was obtained. Next, a final product was obtained in the same manner as that of Example 1-1, except that the indolenium salt shown in Chemical formula (164-5C) was used instead of the indolenium salt shown in Chemical formula (164-1) in Chemical reaction formula (III-1). In this case, the yield was 8.7%.

Next, the indolenium salt shown in Chemical formula (164-2) was obtained by a procedure similar to the procedure shown in Chemical reaction formula (I-2). Subsequently, as shown in Chemical reaction formula (III-2A), the indolenium salt shown in Chemical formula (164-2) (40 mmol), amidine shown in Chemical formula (167-5) (40 mmol), and N,N-dimethylformamide (DMF: 40 g) were mixed. The mixture was reacted and thereby the compound expressed by Chemical formula (174A) (intermediary body) was obtained. Subsequently, as shown in Chemical reaction formula (III-2B), 50 g of chloroform, 50 g water, and 3.2 g of sodium hydroxide were added to the reactant containing the compound shown in Chemical formula (174A). After that, the precipitated solid was filtrated, the filtrate was dried under reduced pressure, and thereby the compound expressed by Chemical formula (174B) (intermediary body) was obtained.

[Formula 51]

[Formula 53]

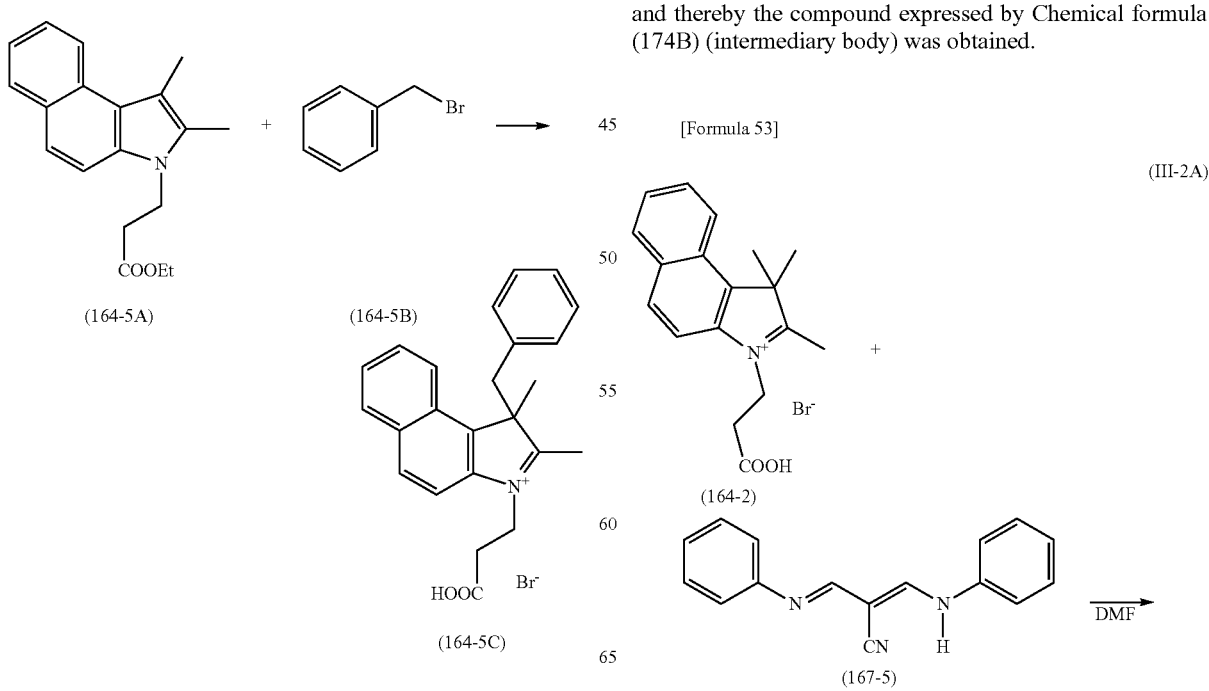

-continued

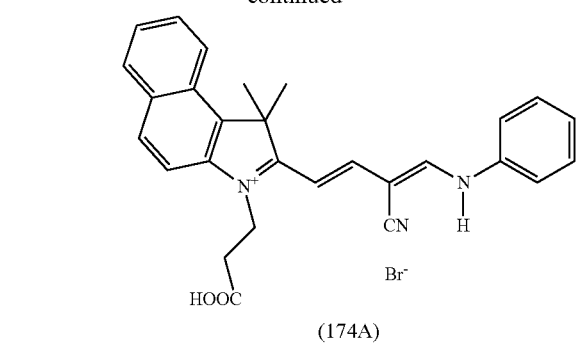

(174A)

[Formula 54]

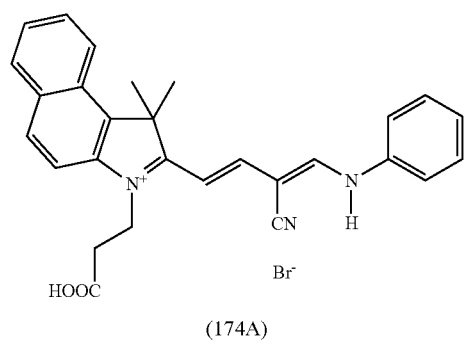

(174A)

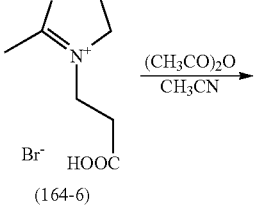

(174B)

Next, as shown in Chemical reaction formula (III-2C), the salt shown in Chemical formula (164-6) (1 mmol), the intermediary body shown in Chemical formula (174B) (1 mmol), acetic anhydride (2 mmol), and acetonitrile (5 g) were mixed. The mixture was reacted at room temperature for 4 hours. Subsequently, 5 g of chloroform, 5 g water, and 0.5 g 35% hydrochloric acid were added to the reactant, and the resultant was stirred for 1 hour. Next, after a water layer was removed from the mixture containing the reactant, 5 g of water and sodium iodide (2 mmol) were added thereto, and the resultant was stirred at 50 deg C for 1 hour. The stirred material was cooled down to room temperature to precipitate a solid. The solid was filtrated, the filtrate was dried under reduced pressure, and thereby a final product was obtained at yield of 20%.

[Formula 55]

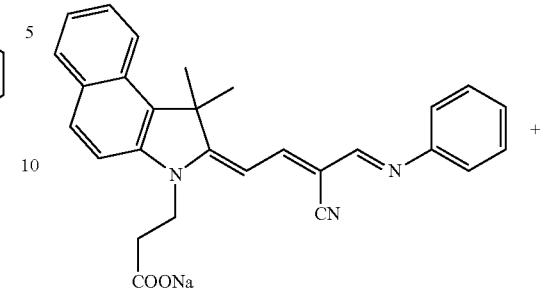

Example 1-7

The compound shown in Chemical formula (159) was synthesized. First, as shown in Chemical reaction formula (I-7), the salt expressed by Chemical formula (164-6) was obtained in the same manner as that of Example 1-3, except that the compound expressed by Chemical formula (162-6) was used instead of the compound shown in Chemical formula (162-3). Subsequently, in the same manner as that of Example 1-5, as shown in Chemical reaction formula (III-2A) and Chemical reaction formula (III-2B), the intermediary body shown in Chemical formula (174B) was obtained. Finally, a final product was obtained in the same manner as that of Example 1-5, except that the salt shown in Chemical formula (164-6) was used instead of the salt shown in Chemical formula (164-5) in Chemical reaction formula (III-2C). In this case, the yield was 25%.

[Formula 56]

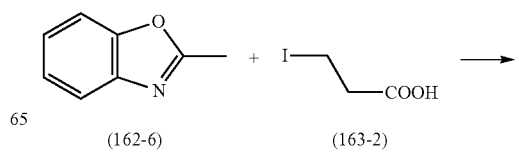

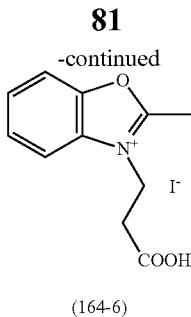

(164-6)

Example 1-8

The compound shown in Chemical formula (160) was synthesized. First, in the same manner as that of Example 1-3, the indolenium salt shown in Chemical formula (164-3) was obtained as shown in Chemical reaction formula (I-3). Subsequently, in the same manner as that of Example 1-5, as shown in Chemical reaction formula (III-2A) and Chemical reaction formula (III-2B), the intermediary body shown in Chemical formula (174B) was obtained. Finally, a final product was obtained in the same manner as that of Example 1-5, except that the indolenium salt shown in Chemical formula (164-3) was used instead of the salt shown in Chemical formula (164-5) in Chemical reaction formula (III-2C). In this case, the yield was 1.1%.

Example 1-9

The compound shown in Chemical formula (161) was synthesized. First, as shown in Chemical reaction formula (I-8), the indolenium salt expressed by Chemical formula (164-7) was obtained in the same manner as that of Example 1-3, except that the compound expressed by Chemical formula (162-7) was used instead of the compound shown in Chemical formula (162-3). Subsequently, in the same manner as that of Example 1-5, as shown in Chemical reaction formula (III-2A) and Chemical reaction formula (III-2B), the intermediary body shown in Chemical formula (174B) was obtained. Finally, a final product was obtained in the same manner as that of Example 1-5, except that the indolenium salt shown in Chemical formula (164-7) was used instead of the salt shown in Chemical formula (164-5) in Chemical reaction formula (III-2C). In this case, the yield was 22%.

[Formula 57]                                      (I-8)

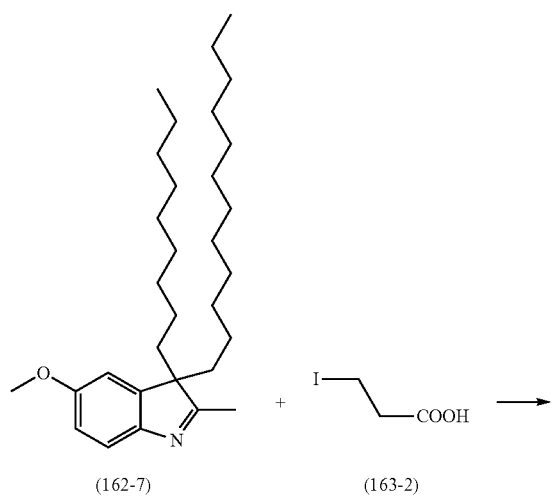

(164-7)

For the final products of Examples 1-1 to 1-9, the structures thereof were identified by nuclear magnetic resonance (NMR) and infrared (IR) absorption spectrum method. In addition, decomposition point, maximum absorption wavelength ($\lambda$max), and molar absorption coefficient (ε) were examined. The results illustrated in Table 1 and Table 2 were obtained.

In NMR measurement, as a measurement equipment, Lambda-400 made by JOEL Co. was used. In this case, a solution in which 3 to 10 mg of the final product was dissolved per 1 $cm^3$ of deuterated dimethyl sulfoxide (DMSO) as a heavy solvent was used as a measurement sample, and $^1$H-NMR spectrum was measured at room temperature. Further, in infrared spectrum measurement, FT-IR-470PLUS made by JASCO Co. was used as a measurement equipment, and the measurement was performed at room temperature by using KBr method.

In examining the decomposition point, a calorimeter TG/DTA6200 made by Shimadzu Corporation was used. In this case, measurement was performed under the conditions that the flow rate of nitrogen gas was 100 $cm^3$/min, and temperature was raised at a ratio of 10 deg C/min in the range from room temperature to 550 deg C.

In examining the maximum absorption wavelength ($\lambda$max) and the molar absorption coefficient (ε), UV spectrum measurement device (U-3010) made by Hitachi, Ltd. was used. In this case, the final product was prepared so that the absorbance became from 0.5 to 1.0 both inclusive in methanol ($CH_3OH$: solvent), which was used for the measurement. The final products of Example 1-4 showed low solubility to methanol, and thus the molar absorption coefficient thereof was not able to be measured.

TABLE 1

| | $^1$H-NMR spectrum (ppm) | Dye (yield) |
|---|---|---|
| Example 1-1 | 12.58(br s, 2H), 8.47(d, 2H), 7.49(d, 2H), 7.37(s, 2H), 7.01(d, 2H), 6.31(d, 2H), 4.40(t, 6H), 3.83(s, 6H), 2.77(t, 4H), 1.70(s, 12H) | Chemical formula (7) (23%) |
| Example 1-2 | 8.70(d, 2H), 8.30(d, 2H), 8.16-8.10(m, 4H), 7.90(d, 2H), 7.73(t, 2H), 7.58(t, 2H), 6.46(d, 2H), 4.59(t, 4H), 2.86(t, 4H), 1.99(s, 12H) | Chemical formula (8) (50%) |
| Example 1-3 | 8.49(d, 2H), 7.51(d, 2H), 7.26(s, 2H), 7.00(d, 2H), 6.35(d, 2H), 4.38(t, 2H), 3.82(s, 6H), 2.54-2.43(m, 8H), 2.17(t, 4H), 1.23-1.07(m, 56H), 0.80(t, 12H), 0.71(br s, 4H), 0.44(br s, 4H) | Chemical formula (9) (2.3%) |
| Example 1-4 | 12.63(s, 2H), 8.18-8.11(m, 4H), 7.91-7.89(d, 2H), 7.65-7.61(t, 2H), 7.52-7.49(t, 2H), 6.58-6.54(d, 2H), 4.71-4.68(t, 4H), 2.87-2.83(t, 4H) | Chemical formula (35) (6.3%) |
| Example 1-5 | 8.90(d, 2H), 8.53(d, 2H), 8.11(d, 2H), 8.05(d, 2H), 7.80(t, 2H), 7.61(t, 4H), 6.96(t, 2H), 6.88(t, 4H), 6.48(d, 2H), 6.39-6.37(m, 4H), 4.25(t, 4H), 4.05(d, 2H), 3.91(t, 2H), 2.15(d, 6H), 1.96(t, 4H) | Chemical formula (47) (8.7%) |
| Example 1-6 | 8.50-8.46(d, 1H), 8.23-8.21(d, 1H), 8.17-8.13(d, 1H), 8.080-8.040(t, 2H), 7.785-7.764(d, 1H), 7.676-7.638(t, 1H), 7.532-7.494(t, 1H), 6.379-6.344(d, 1H), 6.210-6.173(d, 1H), 4.473-4.439(t, 2H), 4.369-4.328(t, 2H), 3.997-3.963(t, 2H), 3.574-3.535(t, 1H), 2.803-2.731(m, 4H), 1.903(s, 6H) | Chemical formula (158) (20%) |
| Example 1-7 | 8.62(d, 1H), 8.56(d, 1H), 8.25(d, 1H), 8.07(t, 2H), 7.92-7.84(m, 1H), 7.84-7.78(m, 2H), 7.66(t, 1H), 7.61-7.58(m, 2H), 7.53(t, 1H), 6.44(d, 1H), 6.26(d, 1H), 4.64(t, 2H), 4.49(t, 2H), 2.91(t, 2H), 2.82(t, 2H), 1.94(s, 6H) | Chemical formula (159) (25%) |
| Example 1-8 | 8.66(d, 1H), 8.53(d, 1H), 8.25(d, 1H), 8.10(t, 1H), 7.87(d, 1H), 7.69(t, 1H), 7.55(t, 1H), 7.53(d, 1H), 7.31(d, 1H), 7.03(d, 1H), 6.49(d, 1H), 6.35(d, 1H), 4.40(t, 4H), 3.83(s, 3H), 2.74(t, 2H), 2.66(t, 2H), 2.46(t, 2H), 2.22(t, 2H), 1.94(s, 6H), 1.23(m, 30H), 0.86-0.74(m, 10H), 0.44(br s, 2H) | Chemical formula (160) (1.1%) |
| Example 1-9 | 8.62(d, 1H), 8.50(d, 1H), 8.23(d, 1H), 8.08(t, 1H), 7.85(d, 1H), 7.68(t, 1H), 7.54(t, 1H), 7.52(d, 1H), 7.28(d, 1H), 7.02(dd, 1H), 6.48(d, 1H), 6.35(d, 1H), 4.48(t, 4H), 3.83(s, 3H), 2.74(t, 2H), 2.65(t, 2H), 2.48(t, 2H), 2.21(t, 2H), 1.93(s, 6H), 1.23(m, 34H), 0.83-0.75(m, 10H), 0.44(br s, 2H) | Chemical formula (161) (22%) |

TABLE 2

| | IR absorption spectrum (cm$^{-1}$) | UV spectrum λmax | UV spectrum ϵ(×10$^5$) | Decomposition point (deg C.) |
|---|---|---|---|---|
| Example 1-1 | 3294, 2970, 2929, 2213, 1732, 1608, 1474, 1435, 1386, 1369, 1320, 1293, 1276, 1225, 1151, 1076, 1019 | 643 | 1.67 | 198 |
| Example 1-2 | 2937, 2212, 1732, 1488, 1461, 1442, 1355, 1292, 1253, 1206, 1167, 1128, 1093 | 653 | 1.79 | 218 |
| Example 1-3 | 2924, 2853, 1716, 1504, 1476, 1434, 1381, 1318, 1279, 1222, 1153, 1025 | 650 | 1.47 | 160 |
| Example 1-4 | 3433, 2206, 1722, 1541, 1475, 1459, 1371, 1317, 1245, 1180, 1153, 1077, 1019 | 614 | — | 174 |
| Example 1-5 | 3420, 2211, 1594, 1491, 1458, 1397, 1357, 1287, 1250, 1208, 1157, 1089, 1003 | 664 | 1.39 | 190 |
| Example 1-6 | 3435, 2986, 2210, 1727, 1600, 1529, 1491, 1459, 1393, 1339, 1280, 1245, 1154, 1125, 1097, 1014 | 580 | 1.32 | 213 |
| Example 1-7 | 2986, 2214, 1735, 1614, 1581, 1489, 1404, 1348, 1281, 1239, 1173, 1121, 1092, 1058, 1015 | 598 | 1.35 | 194 |
| Example 1-8 | 2925, 2852, 2214, 1604, 1498, 1480, 1362, 1284, 1256, 1165, 1131, 1092, 1014 | 651 | 1.55 | 178 |
| Example 1-9 | 3419, 2922, 2851, 1715, 1604, 1498, 1479, 1361, 1282, 1254, 1155, 1130, 1091, 1013 | 651 | 1.60 | 188 |

As illustrated in Table 1 and Table 2, it was confirmed that in Examples 1-1 to 1-9, the compounds shown in Chemical formula (7) to Chemical formula (9), Chemical formula (35), Chemical formula (47), and Chemical formula (158) to Chemical formula (161) were respectively synthesized.

Example 2

As a specific example of the photoelectric conversion device explained in the foregoing embodiment, a dye-sensitized solar cell was fabricated in the following procedure by using the compound shown in Chemical formula (7) synthesized in Example 1-1.

First, the work electrode 10 was formed. First, the conductive substrate 11 composed of a conductive glass substrate (F—SnO$_2$) being 2.0 cm long, 1.5 cm wide, and 1.1 mm thick was prepared. Subsequently, a masking tape having a thickness of 70 μm was adhered to the conductive substrate 11 so that a rectangle being 0.5 cm long and 0.5 cm wide was surrounded by the masking tape. The rectangle section was coated with 3 cm$^3$ of a metal oxide slurry with a uniform thickness, and the resultant was dried. In this case, as the metal oxide slurry, a substance prepared by suspending zinc oxide powder (surface area: 60 m$^2$/g, average primary particle diameter: 50 nm or less, FINEX-30 made by Sakai Chemical Industry Co., Ltd.) to become 10 wt % in water added with 1 drop of Triton X-100 (Triton: registered trademark) as a nonionic interfacial active agent was used. Subsequently, the masking tape on the conductive substrate 11 was exfoliated, the substrate was fired at 450 deg C in an electric furnace, and thereby the metal oxide semiconductor layer 12 having a thickness of about 5 μm was formed. Subsequently, the compound shown in Chemical formula (7) as the cyanine compound shown in Chemical formula (1) and deoxycholic acid were dissolved in dehydrated ethanol so that respective concentrations became $3*10^{-4}$ mol/dm$^3$ and $1*10^{-2}$ mol/dm$^3$ to prepare a dye solution. Subsequently, the conductive substrate 11 on which the metal oxide semiconductor layer 12 was formed was soaked in the foregoing dye solution, and the dye 13 was supported.

Next, the conductive layer 22 having a thickness of 100 nm made of platinum was formed on a single face of the conductive substrate 21 composed of a conductive glass substrate (F—SnO$_2$) being 2.0 cm long, 1.5 cm wide, and 1.1 mm thick by sputtering, and thereby the opposed electrode 20 was formed. In this case, two holes (Φ1 mm) for injecting an electrolytic solution were previously bored in the conductive substrate 21.

Next, the electrolytic solution was prepared. The electrolytic solution was prepared so that respective concentrations of dimethylhexylimidazolium iodide, lithium iodide, and iodine were 0.6 mol/dm$^3$, 0.1 mol/dm$^3$, and 0.05 mol/dm$^3$ in acetonitrile.

Next, a spacer having a thickness of 50 μm was arranged so that the metal oxide semiconductor layer 12 was surrounded by the spacer. After that, the face where the dye 13 was supported out of the work electrode 10 and the face where the conductive layer 22 was formed out of the opposed electrode 20 were opposed to each other and was bonded with each other with the spacer in between. After that, the prepared electrolytic solution was injected through the injection inlet previously bored in the opposed electrode 20, and thereby the electrolyte-containing layer 30 was formed. Finally, the entire body was sealed, and thereby the dye-sensitized solar cell was obtained.

Comparative Examples 1-1 and 1-2

A procedure similar to that of Example 2 was taken, except that the dye (Comparative example 1-1) shown in the following Chemical formula (175) or the dye (Comparative example 1-2) shown in the following Chemical formula (176) was used instead of the compound shown in Chemical formula (7).

[Formula 58]

(175)

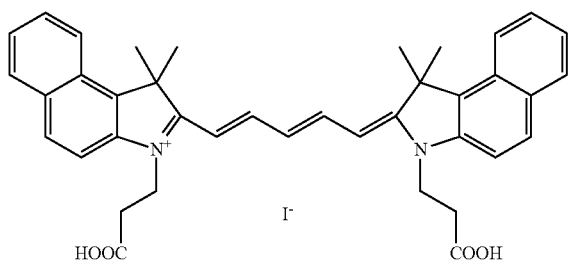

(176)

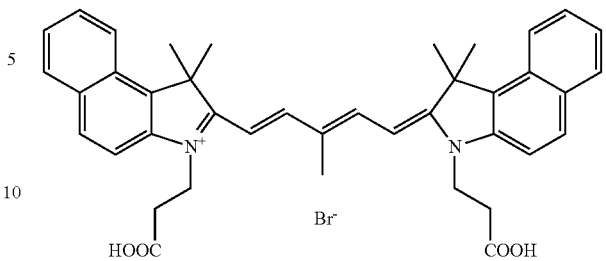

For the dye-sensitized solar cells of Example 2 and Comparative examples 1-1 and 1-2, dye exfoliation test was performed. The results illustrated in FIG. 3 were obtained.

The exfoliation test was performed by the following procedure. First, in the work electrode 10 before being bonded with the opposed electrode 20, for the surface where the dye 13 was supported out of the metal oxide semiconductor layer 12, absorption spectrum in the measurement wavelength range from 350 nm to 850 nm was measured by a UV spectrum measurement device. The absorption spectrum was regarded as initial data (FIG. 3(A)). Next, after the dye-sensitized solar cell (cell) was fabricated as described above and was decomposed. The surface of the metal oxide semiconductor layer 12 of the work electrode 10 was washed with acetonitrile, and the absorption spectrum was measured as the initial data was. Such absorption spectrum was regarded as data after cell evaluation (FIG. 3(B)). Further, the work electrode 10 after measuring the data after cell evaluation was soaked into 100 cm$^3$ of an acetonitrile mixed liquid containing water at a ratio of 10 wt % for 2 hours. After that, absorption spectrum was measured again as the initial data was. Such absorption spectrum was regarded as data after soaking in acetonitrile containing 10 wt % water for 2 hours (FIG. 3(C)). The foregoing series of absorption spectrum measurement was performed by using UV-3101 PC made by Shimadzu Corporation, in which a slit width was 5 nm.

Figure 3A:
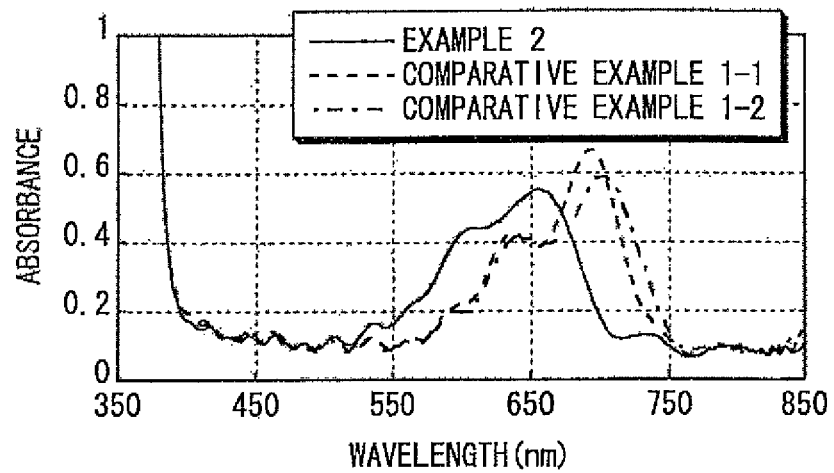
FIG. 3A is a graph illustrating initial absorbance results of dye exfoliation test in an example and comparative examples.
Figure 3B:
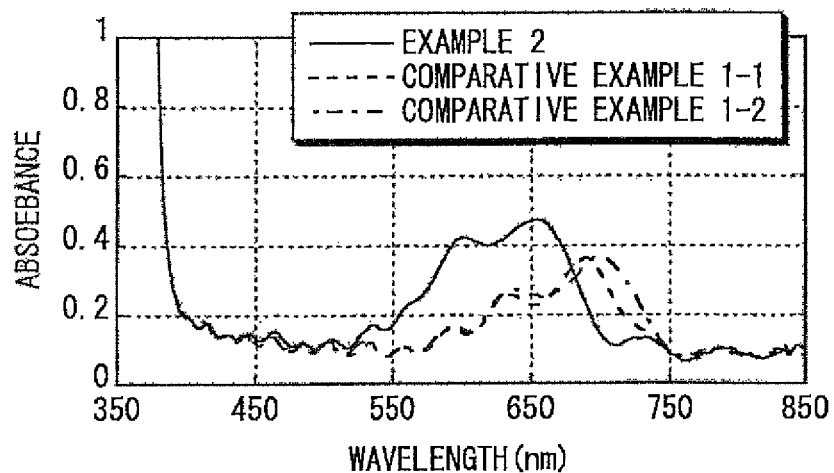
FIG. 3B is a graph illustrating absorbance results of dye exfoliation test in an example and comparative examples after cell evaluation.
Figure 3C:
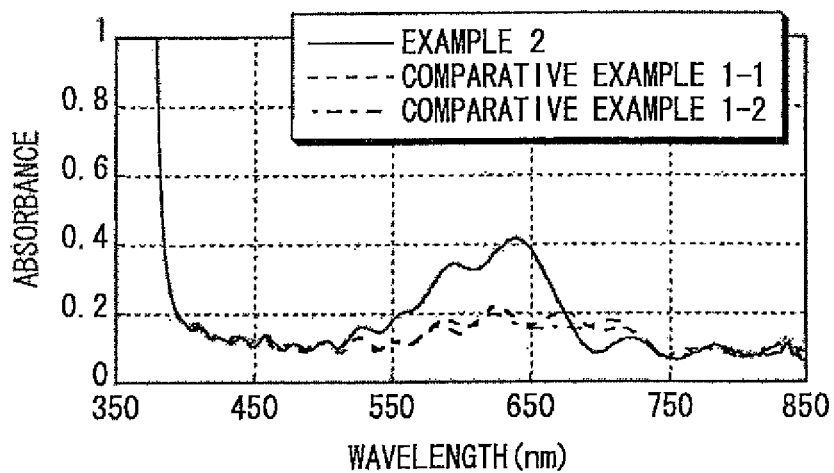
FIG. 3C is a graph illustrating initial absorbance results of dye exfoliation test in an example and comparative examples after soaking in acetonitrile containing 10 wt % water for 2 hours.

As illustrated in FIG. 3(A) to FIG. 3(C), in Example 2 in which the dye 13 contained the compound shown in Chemical formula (7), in wavelength 650 nm in the vicinity of absorption peak, the absorbance after cell evaluation was slightly lower than the absorbance of the initial data, and the absorbance after soaking in acetonitrile containing 10 wt % water for 2 hours was slightly lower than the absorbance after cell evaluation. Meanwhile, in Comparative examples 1-1 and 1-2 containing the dye in which the cyano group was not introduced to the methine chain skeleton, in wavelength 700 nm in the vicinity of absorption peak, the absorbance after cell evaluation was significantly lower than the absorbance of the initial data, and the absorbance after soaking in acetonitrile containing water for 2 hours was significantly lower than the absorbance after cell evaluation. That is, since the metal oxide semiconductor layer 12 supporting the dye was soaked into acetonitrile containing the electrolytic solution and moisture, exfoliation of the dye was significantly generated in Comparative examples 1-1 and 1-2, while exfoliation of the dye 13 was inhibited in Example 2. From the result, it is regarded that in the case where the structure shown in Chemical formula (1) has the anchor structure and the cyano group introduced to the methine chain skeleton, absorption characteristics of the dye to the metal oxide semiconductor layer 12 is improved, and thus the dye is hardly exfoliated.

Accordingly, it was confirmed that in the dye and the dye-sensitized solar cell using the same in this example, since the dye had the cyanine structure shown in Chemical formula (1), fixation characteristics to the base substance (metal oxide semiconductor layer 12) containing the metal oxide semiconductor material were able to be improved.

Examples 3-1 to 3-8

A dye-sensitized solar cell was fabricated in the same manner as that of Example 2, except that the compounds shown in Chemical formula (8), Chemical formula (9), Chemical formula (35), Chemical formula (47), and Chemical formula (158) to Chemical formula (161) synthesized in Examples 1-2 to 1-9 as illustrated in Table 3 were used instead of the compound shown in Chemical formula (7) as a dye.

Comparative Examples 2-1 to 2-7

A dye-sensitized solar cell was fabricated in the same manner as that of Example 2, except that the dyes shown in the following Chemical formula (177) to Chemical formula (183) as illustrated in Table 3 were used instead of the compound shown in Chemical formula (7) as a dye.

[Formula 59]

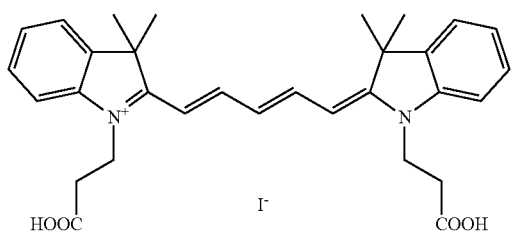

(177)

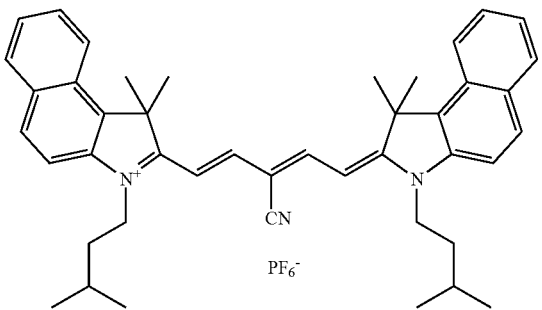

(178)

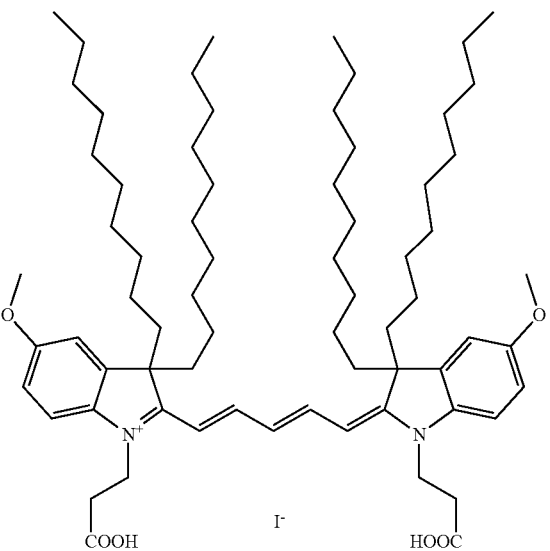

(179)

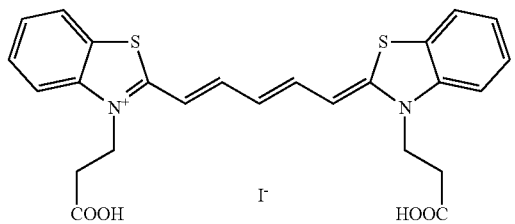

(180)

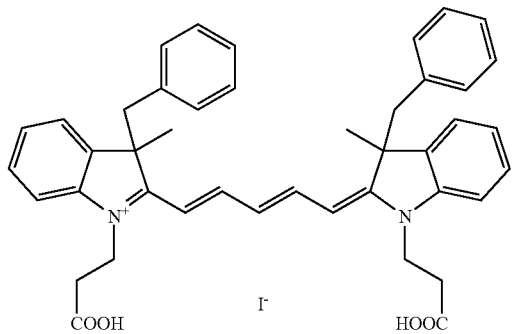

(181)

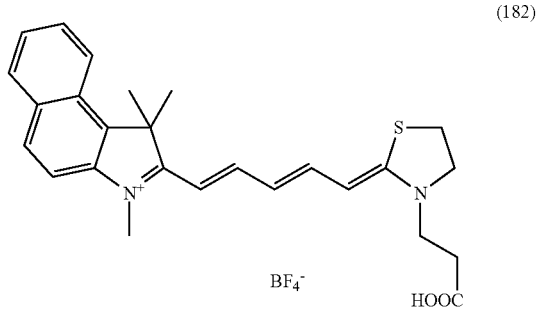

(182)

(183)

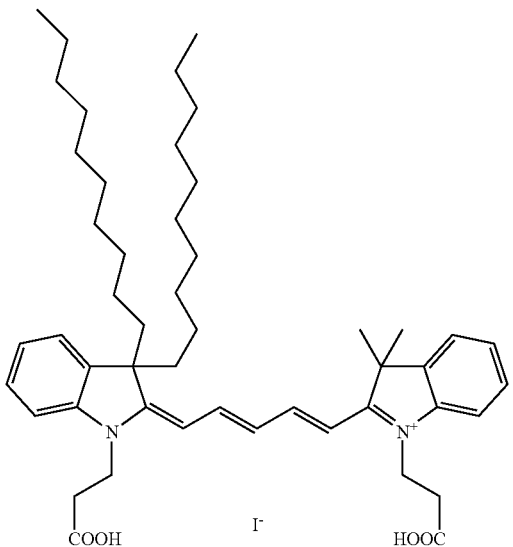

For the dye-sensitized solar cells of Examples 3-1 to 3-8, Comparative examples 2-1 to 2-7, Example 2, and Comparative example 1-1, conversion efficiency was examined, and the results illustrated in Table 3 were obtained. Further, for these examples and these comparative examples, dye residual ratio after soaking in acetonitrile containing 10 wt % water for 2 hours was examined by a procedure similar to that of the foregoing exfoliation test. The results are also illustrated in Table 3.

Correspondence relation between the respective examples and the respective comparative examples in Table 3 are as follows. Comparative examples corresponding to Examples 2 and 3-1 are Comparative examples 1-1 and 2-1. Comparative example corresponding to Example 3-2 is Comparative example 2-3. Comparative example corresponding to Example 3-3 is Comparative example 2-4. Comparative example corresponding to Example 3-4 is Comparative example 2-5. Comparative example corresponding to Examples 3-5 and 3-6 is Comparative example 2-6. Comparative example corresponding to Examples 3-7 and 3-8 is Comparative example 2-7.

The conversion efficiency was obtained with the use of AM1.5 (1000 W/m$^2$) solar simulator as a light source by the following calculation method. First, a voltage of the dye-sensitized solar cells was swept by a source measurement device to measure a response current. Thereby, a value obtained by dividing the maximum output as a product of a voltage and a current by light intensity per 1 cm$^2$ was multiplied by 100, and the resultant percent value was regarded as conversion efficiency ($\eta$: %). That is, the conversion efficiency is expressed by (maximum output/light intensity per 1 cm$^2$)*100.

In examining the dye residual ratio, the initial data and the data after soaking in acetonitrile containing 10 wt % water for 2 hours were measured by a procedure similar to that of the foregoing exfoliation test, and each dye peak intensity in each spectrum was examined. Subsequently, under the conditions that the dye peak intensity in the initial data was 100%, the dye residual ratio was calculated from a ratio of the dye peak intensity in the data after soaking in acetonitrile containing 10 wt % water for 2 hours. In this case, absorption of the metal oxide semiconductor layer 12 was canceled by difference spectrum, and the dye residual ratio was calculated from the dye peak intensity.

TABLE 3

Metal oxide semiconductor layer: ZnO (sintering method)

| | Dye | Conversion efficiency (%) | Dye residual ratio after soaking in acetonitrile containing 10 wt % water for 2 hours |
|---|---|---|---|
| Example 2 | Chemical formula (7) | 1.10 | 64 |
| Example 3-1 | Chemical formula (8) | 0.91 | 63 |
| Example 3-2 | Chemical formula (9) | 1.81 | 68 |
| Example 3-3 | Chemical formula (35) | 0.80 | 65 |
| Example 3-4 | Chemical formula (47) | 1.36 | 67 |
| Example 3-5 | Chemical formula (158) | 1.01 | 60 |
| Example 3-6 | Chemical formula (159) | 0.90 | 61 |
| Example 3-7 | Chemical formula (160) | 1.73 | 68 |
| Example 3-8 | Chemical formula (161) | 1.89 | 69 |
| Comparative example 1-1 | Chemical formula (175) | 0.70 | 18 |
| Comparative example 2-1 | Chemical formula (177) | 0.70 | 23 |
| Comparative example 2-2 | Chemical formula (178) | Incapable measurement | — |
| Comparative example 2-3 | Chemical formula (179) | 1.24 | 21 |
| Comparative example 2-4 | Chemical formula (180) | 0.13 | 15 |
| Comparative example 2-5 | Chemical formula (181) | 1.04 | 20 |
| Comparative example 2-6 | Chemical formula (182) | 0.72 | 16 |
| Comparative example 2-7 | Chemical formula (183) | 1.21 | 20 |

As illustrated in Table 3, in Examples 2 and 3-1 to 3-8 in which the dye 13 contained the compound shown in Chemical formula (7) that has the anchor group and the cyano group introduced to the methine chain skeleton and the like, the conversion efficiency and the dye residual ratio were higher than those of corresponding Comparative examples 1-1 and 2-1 to 2-7 using the dye in which the cyano group was not introduced to the methine chain skeleton. In Comparative example 2-2 using the compound shown in Chemical formula (178) that did not contain the anchor group in the structure, since the dye was not supported to the metal oxide semiconductor layer, conversion efficiency was not able to be measured. The results show that in the case where the structure shown in Chemical formula (1) has the anchor group and the cyano group introduced to the methine chain skeleton, fixation characteristics of the dye to the metal oxide semiconductor layer 12 is improved, and electron injection efficiency to the metal oxide semiconductor layer 12 is improved.

Further, in all of Examples 2, 3-1, 3-3, 3-5, and 3-6, each conversion efficiency was 0.9% or more, and each dye residual ratio was 60% or more. Of the foregoing, by comparison among Examples 3-3, 3-5, and 3-6, in Examples 3-5 and 3-6 in which one of the heterocycles bonded with both ends of the methine chain includes the indolenine skeleton, conversion efficiency was higher than that of Example 3-3 in which the indolenine skeleton was not included. The similar tendency was shown in comparison between Comparative examples 2-4 and 2-6. From the result, it is regarded that in the case where at least one of the heterocycles bonded with both ends of the methine chain includes the indolenine skeleton, planarity of the entire compound is lowered and formation of an association body is more inhibited than in a case that both heterocycles include a skeleton that more easily increases planarity of the entire compound than the indolenine skeleton such as a thiazole skeleton. Examples of the skeleton that more easily increases planarity of the entire compound than the indolenine skeleton include an imidazole skeleton, a tellurazole skeleton, and selerazole skeleton.

Further, in Example 2, the conversion efficiency was higher than that of Example 3-1. The result shows that in the case where a benzene ring having a methoxy group as an electron-donating is included as the ring A and the ring B in the structure shown in Chemical formula (4), electron injection efficiency to the metal oxide semiconductor layer 12 is more improved.

Further, in Examples 3-2, 3-4, 3-7, and 3-8, the conversion efficiency was higher than that of Examples 2 and 3-1. The result showed that in the case where a sterically bulky group such as an alkyl group with carbon atomicity from 10 to 12 both inclusive and a benzyl group was introduced as at least one of R9, R10, R12, and R13 in the structure shown in Chemical formula (4), the steric size of the entire molecule became large, and the ratio of the association body that hardly contributes to photoelectric conversion in the dye was decreased.

Accordingly, in the dye-sensitized solar cell in the examples, in the case where the metal oxide semiconductor layer 12 was formed by sintering method and contained zinc oxide, the following was confirmed. That is, in the case where the dye 13 contains the cyanine compound shown in Chemical formula (1), conversion efficiency and dye residual ratio are improved. In this case, at least one of the heterocycles bonded with both ends of the methine chain includes the indolenine skeleton as the compound shown in Chemical formula (3), conversion efficiency is more improved. Further, in the case where the ring A and the ring B in Chemical formula (4) is a benzene ring having a methoxy group, conversion efficiency is more improved. Furthermore, in the case where a sterically bulky group such as an alkyl group with carbon atomicity from 6 to 25 both inclusive and the group shown in Chemical formula (2) is introduced as one of R9 to R13 in Chemical formula (4), conversion efficiency is more improved.

Thus, it was confirmed that in the dye in the examples, since the cyanine structure shown in Chemical formula (1) was contained, fixation characteristics and electron injection efficiency to the base substance containing the metal oxide semiconductor material were able to be improved. It was confirmed that in this case, if the ring A and the ring B in Chemical formula (4) were a benzene ring having a methoxy group, higher electron injection efficiency was able to be obtained. It was also confirmed that if a sterically bulky group was introduced as R9 to R13 in Chemical formula (4), still higher electron injection efficiency was able to be obtained.

Examples 4-1 to 4-9

A procedure similar to that of Examples 2 and 3-1 to 3-8 was taken, except that the metal oxide semiconductor layer 12 was formed by electrolytic precipitation method. In this case, 40 ml of an electrolytic solution prepared so that respective concentrations of eosin Y, zinc chloride, and potassium chloride were 30 µmol/dm³, 5 mmol/dm³, and 0.09 mol/dm³ in water; an opposed electrode composed of a zinc plate; and a reference electrode composed of a silver/silver chloride electrode were prepared. Subsequently, an electrolytic bath liquid was provided with bubbling with the use of oxygen for 15 minutes. After that, a film was formed on the surface of the conductive substrate 11 by providing constant-potential electrolysis with electric potential of −1.0 V for 60 minutes at temperature of a solution in the electrolytic bath liquid of 70 deg C while providing bubbling. The substrate was not dried and soaked into a potassium hydroxide aqueous solution (pH11), and was subsequently washed with water, and thereby eosin Y was desorbed. Subsequently, the resultant was dried for 30 minutes at 150 deg C.

Comparative Examples 3-1 to 3-6

A procedure similar to that of Comparative examples 1-1 and 2-3 to 2-7 was taken, except that the metal oxide semiconductor layer 12 was formed by electrolytic precipitation method as in Examples 4-1 to 4-9.

For the dye-sensitized solar cells of Examples 4-1 to 4-9 and Comparative examples 3-1 to 3-6, conversion efficiency was examined as in Example 2, and the results illustrated in Table 4 were obtained. Correspondence relation between the respective examples and the respective comparative examples in Table 4 are as follows. Comparative example corresponding to Examples 4-1 and 4-2 is Comparative example 3-1. Comparative example corresponding to Example 4-3 is Comparative example 3-2. Comparative example corresponding to Example 4-4 is Comparative example 3-3. Comparative example corresponding to Example 4-5 is Comparative example 3-4. Comparative example corresponding to Examples 4-6 and 4-7 is Comparative example 3-5. Comparative example corresponding to Examples 4-8 and 4-9 is Comparative example 3-6.

TABLE 4

Metal oxide semiconductor layer: ZnO (electrolytic precipitation method)

| | Dye | Conversion efficiency (%) |
|---|---|---|
| Example 4-1 | Chemical formula (7) | 1.84 |
| Example 4-2 | Chemical formula (8) | 1.3 |
| Example 4-3 | Chemical formula (9) | 2.77 |
| Example 4-4 | Chemical formula (35) | 1.09 |
| Example 4-5 | Chemical formula (47) | 2.45 |
| Example 4-6 | Chemical formula (158) | 1.16 |
| Example 4-7 | Chemical formula (159) | 0.99 |
| Example 4-8 | Chemical formula (160) | 2.65 |
| Example 4-9 | Chemical formula (161) | 2.95 |
| Comparative example 3-1 | Chemical formula (175) | 0.99 |
| Comparative example 3-2 | Chemical formula (179) | 2.33 |
| Comparative example 3-3 | Chemical formula (180) | 0.52 |
| Comparative example 3-4 | Chemical formula (181) | 2.03 |
| Comparative example 3-5 | Chemical formula (182) | 0.72 |

TABLE 4-continued

Metal oxide semiconductor layer: ZnO
(electrolytic precipitation method)

| | Dye | Conversion efficiency (%) |
|---|---|---|
| Comparative example 3-6 | Chemical formula (183) | 2.27 |

As illustrated in Table 4, in the case where the metal oxide semiconductor layer 12 was formed by electrolytic precipitation method, results similar to those of Table 3 were obtained. That is, in Examples 4-1 to 4-9 in which the dye 13 contained the compound shown in Chemical formula (7) that had the anchor group and the cyano group introduced to the methine chain skeleton and the like, the conversion efficiency was higher than those of corresponding Comparative examples 3-1 to 2-6 using the dye in which the cyano group was not introduced to the methine chain skeleton. Further, in all of Examples 4-1, 4-2, 4-4, 4-6, and 4-7, each conversion efficiency was about 1% or more. Of the foregoing, by comparison among Examples 4-4, 4-6, and 4-7, in Examples 4-6 and 4-7 in which one of the heterocycles bonded with both ends of the methine chain includes the indolenine skeleton, conversion efficiency was higher than that of Example 4-4 in which the indolenine skeleton was not included. Further, in Example 4-1, the conversion efficiency was higher than that of Example 4-2. In Examples 4-3, 4-5, 4-8, and 4-9, conversion efficiency was higher than that of Examples 4-1 and 4-2.

Accordingly, in the dye-sensitized solar cell in the examples, in the case where the metal oxide semiconductor layer 12 was formed by electrolytic precipitation method and contained zinc oxide, the following was confirmed. That is, in the case where the dye 13 contains the cyanine compound shown in Chemical formula (1), conversion efficiency is improved. In this case, at least one of the heterocycles bonded with both ends of the methine chain includes the indolenine skeleton as the compound shown in Chemical formula (3), conversion efficiency is more improved. Further, in the case where the ring A and the ring B in Chemical formula (4) are a benzene ring having a methoxy group, conversion efficiency is more improved. Furthermore, in the case where a sterically bulky group such as an alkyl group with carbon atomicity from 6 to 25 both inclusive and the group shown in Chemical formula (2) is introduced as one of R9, R10, R12, and R13 in Chemical formula (4), conversion efficiency is more improved.

Thus, it was confirmed that in the dye in the examples, since the cyanine structure shown in Chemical formula (1) was contained, fixation characteristics and electron injection efficiency to the base substance containing the metal oxide semiconductor material were able to be improved. It was confirmed that in this case, if the ring A and the ring 13 in Chemical formula (4) were a benzene ring having a methoxy group, higher electron injection efficiency was able to be obtained. It was also confirmed that if a sterically bulky group was introduced as R9 to R13 in Chemical formula (4), still higher electron injection efficiency was able to be obtained.

Examples 5-1 to 5-9

A procedure similar to that of Examples 2 and 3-1 to 3-8 was taken, except that a metal oxide slurry containing titanium oxide ($TiO_2$) powder was used instead of zinc oxide powder in forming the metal oxide semiconductor layer 12 by sintering method. In this case, the metal oxide slurry containing titanium oxide powder was prepared as follows. First, 125 $cm^3$ of titanisopropoxide was added to 750 $cm^3$ of 0.1 mol/$dm^3$ nitric acid aqueous solution while being stirred, and was heavily stirred for 8 hours at 80 deg C. The obtained liquid was poured into a pressure container made of Teflon (registered trademark), and the pressure container was processed in an autoclave for 16 hours at 230 deg C. After that, a liquid (sol liquid) containing precipitate provided with autoclave process was stirred, and thereby was resuspended. Subsequently, the suspending solution was suctioned and filtrated to remove precipitate that was not resuspended, and the sol filtrate was condensed by an evaporator until the concentration of titanium oxide became 11 wt %. After that, to improve coating characteristics to the substrate, one drop of Triton X-100 was added to the concentrated liquid. Subsequently, titanium oxide powder having an average particle diameter of 30 nm (P-25 made by Aerosil Japan) was added to the sal concentrated liquid so that the content ratio of titanium oxide was 33 wt % as a whole. The resultant was provided with centrifugal stirring by using rotation and orbital motion for 1 hour, dispersed, and thereby the metal oxide slurry was prepared.

Comparative Examples 4-1 to 4-6

A procedure similar to that of Comparative examples 1-1 and 2-3 to 2-7 was taken, except that a metal oxide slurry containing titanium oxide ($TiO_2$) powder was used instead of zinc oxide powder in forming the metal oxide semiconductor layer 12 by sintering method as in Examples 5-1 to 5-9.

For the dye-sensitized solar cells of Examples 5-1 to 5-9 and Comparative examples 4-1 to 4-6, conversion efficiency was examined as in Example 2, and the results illustrated in Table 5 were obtained.

TABLE 5

Metal oxide semiconductor layer: $TiO_2$ (sintering method)

| | Dye | Conversion efficiency (%) |
|---|---|---|
| Example 5-1 | Chemical formula (7) | 0.39 |
| Example 5-2 | Chemical formula (8) | 0.39 |
| Example 5-3 | Chemical formula (9) | 0.45 |
| Example 5-4 | Chemical formula (35) | 0.3 |
| Example 5-5 | Chemical formula (47) | 0.42 |
| Example 5-6 | Chemical formula (158) | 0.3 |
| Example 5-7 | Chemical formula (159) | 0.3 |
| Example 5-8 | Chemical formula (160) | 0.44 |
| Example 5-9 | Chemical formula (161) | 0.44 |
| Comparative example 4-1 | Chemical formula (175) | 0.32 |
| Comparative example 4-2 | Chemical formula (179) | 0.41 |
| Comparative example 4-3 | Chemical formula (180) | 0.20 |
| Comparative example 4-4 | Chemical formula (181) | 0.39 |
| Comparative example 4-5 | Chemical formula (182) | 0.25 |
| Comparative example 4-6 | Chemical formula (183) | 0.41 |

As illustrated in Table 5, in the case where the metal oxide semiconductor layer 12 containing titanium oxide was formed, results similar to those of Table 3 were obtained. That is, in Examples 4-1 to 4-9 in which the dye 13 contained the compound shown in Chemical formula (7) that had the anchor group and the cyano group introduced to the methine chain skeleton and the like, the conversion efficiency was higher than those of corresponding Comparative examples 3-1 to 2-6 using the dye in which the cyano group was not introduced to the methine chain skeleton. Further, in all of Examples 4-1, 4-2, 4-4, 4-6, and 4-7, each conversion efficiency was about 1% or more. Of the foregoing, by comparison among Examples 4-4, 4-6, and 4-7, in Examples 4-6 and 4-7 in which one of the heterocycles bonded with both ends of the methine chain includes the indolenine skeleton, conversion efficiency was higher than that of Example 4-4 in which the indolenine skeleton was not included. Further, in Example 4-1, the conversion efficiency was higher than that of Example 4-2. In Examples 4-3, 4-5, 4-8, and 4-9, conversion efficiency was higher than that of Examples 4-1 and 4-2.

Accordingly, in the dye-sensitized solar cell in the examples, in the case where the metal oxide semiconductor layer 12 was formed by electrolytic precipitation method and contained zinc oxide, the following was confirmed. That is, in the case where the dye 13 contains the cyanine compound shown in Chemical formula (1), conversion efficiency is improved. In this case, at least one of the heterocycles bonded with both ends of the methine chain includes the indolenine skeleton as the compound shown in Chemical formula (3), conversion efficiency is more improved. Further, in the case where the ring A and the ring B in Chemical formula (4) are a benzene ring having a methoxy group, conversion efficiency is more improved. Furthermore, in the case where a sterically bulky group such as an alkyl group with carbon atomicity from 6 to 25 both inclusive and the group shown in Chemical formula (2) is introduced as one of R9, R10, R12, and R13 in Chemical formula (4), conversion efficiency is more improved. Thus, it was confirmed that in the dye in the examples, since the cyanine compound shown in Chemical formula (1) was contained, fixation characteristics and electron injection efficiency to the base substance containing the metal oxide semiconductor material were able to be improved. It was confirmed that in this case, if the ring A and the ring B in Chemical formula (4) were a benzene ring having a methoxy group, higher electron injection efficiency was able to be obtained. It was also confirmed that if a sterically bulky group was introduced as R9 to R13 in Chemical formula (4), still higher electron injection efficiency was able to be obtained.

Further, from the results of Table 3 to Table 5, focusing attention on the method of forming the metal oxide semiconductor layer 12 and the material thereof, in Examples 4-1 to 4-9 in which the metal oxide semiconductor layer 12 was formed by electrolytic precipitation method, conversion efficiency was more improved than in Examples 2 and 3-1 to 3-8 in which the metal oxide semiconductor layer 12 was formed by sintering method. Further, in Examples 5-1 to 5-9 in which the metal oxide semiconductor layer 12 was formed by sintering method and titanium oxide was contained, conversion efficiency was lowered than in Examples 2 and 3-1 to 3-8 in which the metal oxide semiconductor layer 12 was formed by sintering method and zinc oxide was contained. Such a tendency was similarly shown in comparison among the comparative examples. However, difference of conversion efficiency (increase ratio) between the case that the metal oxide semiconductor layer 12 was formed by sintering method and the case that the metal oxide semiconductor layer 12 was formed by electrolytic precipitation method was larger in the examples than in the comparative examples. Such increase ratio of conversion efficiency was similarly shown when comparison was made between the case that the metal oxide semiconductor layer 12 was formed by sintering method and titanium oxide was contained and the case that the metal oxide semiconductor layer 12 was formed by sintering method and zinc oxide was contained.

The present invention has been described with reference to the embodiment and the examples. However, the present invention is not limited to the aspects explained in the foregoing embodiment and the foregoing examples, and various modifications may be made. For example, usage application of the photoelectric conversion device of the present invention is not always limited to the application already explained, but other applications may be adopted. Examples of other applications include a light sensor.

The invention claimed is:
1. A photoelectric conversion device comprising:
an electrode having a dye and a support body that supports the dye, the dye containing a cyanine compound represented by Chemical formula (4):

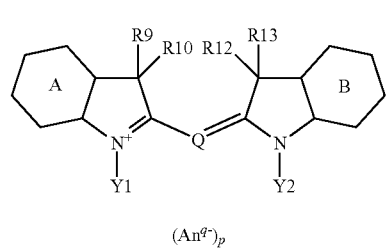

(4)

where:
R9, R10, R12, and R13 are independently a hydrogen atom, a hydroxyl group, an alkyl group, an alkoxy group, an alkyl group having one or more substituent groups, an alkoxy group having one or more substituent groups, or a group represented by Chemical formula (2);
Y1 and Y2 are each an anchor group;
Q is a linkage group that has a methine chain with carbon atomicity from 1 to 7 both inclusive as a skeleton and that has one or more cyano groups;
ring A and the ring B are independently a benzene ring, a naphthalene ring, a benzene ring having one or more substituent groups, or a naphthalene ring having one or more substituent groups;
$An^{q-}$ is an anion with q valency;
q is 1 or 2; and
p is a coefficient to maintain neutral electric charge;

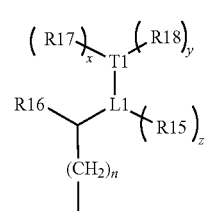

(2)

where:
the bond between L1 and T1 is a double bond or a triple bond;
L1 represents a carbon atom;
T1 represents a carbon atom, an oxygen atom, or a nitrogen atom;

x, y, and z are independently 0 or 1, x and y are 0 where T1 is an oxygen atom, and (y+z) is 0 or 1 where T1 is a nitrogen atom;

R15 to R17 are independently a hydrogen atom, a hydroxyl group, a nitro group, a cyano group, a halogen atom, an alkyl group with carbon atomicity from 1 to 4 both inclusive, or an alkyl group with carbon atomicity from 1 to 4 both inclusive substituted by one or more halogen atoms;

R18 is a hydrogen atom, a hydroxyl group, a nitro group, a cyano group, a halogen atom, an alkyl group with carbon atomicity from 1 to 4 both inclusive, an alkoxy group with carbon atomicity from 1 to 4 both inclusive, an alkyl group with carbon atomicity from 1 to 4 both inclusive substituted by one or more halogen atoms, or an alkoxy group with carbon atomicity from 1 to 4 both inclusive substituted by one or more halogen atoms;

R15 and R18/R16 and R17 may be respectively linked with each other to form ring structure; and n is an integer from 0 to 4, wherein at least one of R9, R10, R12, and R13 shown in Chemical formula (4) is an alkyl group with carbon atomicity from 6 to 25 both inclusive.

2. The photoelectric conversion device according to claim 1, wherein ring A and ring B shown in Chemical formula (4) are a benzene ring having a methoxy group.

3. The photoelectric conversion device according to claim 1, wherein all of R9, R10, R12, and R13 shown in Chemical formula (4) is the alkyl group with carbon atomicity from 6 to 25 both inclusive.

4. The photoelectric conversion device according to claim 1, wherein Q is a linkage group in which a methine chain with carbon atomicity of 5 is a skeleton and a cyano group is introduced to a carbon atom as a center of the methine chain.

5. The photoelectric conversion device according to claim 1, wherein the anchor group is a group represented by —$CH_2$—$CH_2$—C(=O)—OH or a group represented by —$CH_2$—$CH_2$—C(=O)—$O^-$.

6. The photoelectric conversion device according to claim 1, wherein the support body is formed by electrolytic precipitation and contains zinc oxide (ZnO).

* * * * *